US010662414B2

(12) United States Patent
Martin et al.

(10) Patent No.: US 10,662,414 B2
(45) **Date of Patent: *May 26, 2020**

(54) METHODS FOR TREATING OR PREVENTING HBV INFECTION OR HBV RELATED DISEASES

(71) Applicant: Transgene S.A., Illkirch Graffenstaden (FR)

(72) Inventors: Perrine Martin, Decines (FR); Nathalie Silvestre, Ergersheim (FR); Jean-Baptiste Marchand, Obernai (FR)

(73) Assignee: Transgene S.A., Illkirch Graffenstaden (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/257,784

(22) Filed: Jan. 25, 2019

(65) Prior Publication Data

US 2019/0144840 A1 May 16, 2019

Related U.S. Application Data

(60) Continuation of application No. 15/369,118, filed on Dec. 5, 2016, now Pat. No. 10,190,105, which is a division of application No. 14/232,082, filed as application No. PCT/EP2012/063640 on Jul. 12, 2012, now Pat. No. 9,512,412.

(30) Foreign Application Priority Data

Jul. 12, 2011 (EP) .................................... 11305909
Apr. 18, 2012 (EP) .................................... 12305450

(51) Int. Cl.

| | |
|---|---|
| ***C12N 9/12*** | (2006.01) |
| ***C12P 21/02*** | (2006.01) |
| ***C12N 7/00*** | (2006.01) |
| ***C07K 14/005*** | (2006.01) |
| ***A61K 39/29*** | (2006.01) |
| ***C12N 9/22*** | (2006.01) |
| *A61K 38/00* | (2006.01) |
| *A61K 39/00* | (2006.01) |

(52) U.S. Cl.

CPC .......... *C12N 9/1252* (2013.01); *A61K 39/292* (2013.01); *C07K 14/005* (2013.01); *C12N 7/00* (2013.01); *C12N 9/1276* (2013.01); *C12N 9/22* (2013.01); *C12P 21/02* (2013.01); *C12Y 207/07007* (2013.01); *C12Y 301/26004* (2013.01); *A61K 38/00* (2013.01); *A61K 2039/53* (2013.01); *C07K 2319/02* (2013.01); *C07K 2319/03* (2013.01); *C07K 2319/40* (2013.01); *C12N 2730/10122* (2013.01); *C12N 2730/10134* (2013.01); *C12N 2799/022* (2013.01); *C12N 2799/023* (2013.01)

(58) Field of Classification Search

None

See application file for complete search history.

(56) References Cited

U.S. PATENT DOCUMENTS

| | | | | |
|---|---|---|---|---|
| 9,512,412 | B2 * | 12/2016 | Martin | C12N 9/22 |
| 10,190,105 | B2 * | 1/2019 | Martin | C12N 9/22 |

FOREIGN PATENT DOCUMENTS

| | | |
|---|---|---|
| WO | WO 95/03777 | 2/1995 |
| WO | WO 2008/020656 | 2/2008 |
| WO | WO 2011/015656 | 2/2011 |

OTHER PUBLICATIONS

Accession B1ABK3 (Apr. 8, 2008).
Accession Q96846 (Feb. 1, 1997).
Accession A00703 (Mar. 17, 1987).
Accession S47406 (Nov. 23, 1994).
Accession Q67952 (Nov. 1, 1996).
Argos et al., *A model for the hepatitis B virus core protein: prediction of antigenic sites and relationship to RNA virus capsid proteins,* 7(3) The EMBO Journal 819-824 (1988).
Bartenschlager et al., *The P Gene Product of Hepatitis B Virus Is Required as a Structural Component for Genomic RNA Encapsidation,* 64(11) Journal of Virology 5324-5332 (Nov. 1990).
Bock et al., *Selection of hepatitis B virus polymerase mutants with enhanced replication by lamivudine treatment after liver transplantation,* 122(2) Gastroenterology 264-273 (Feb. 2002).
Borisova et al., *Hybrid Hepatitis B Virus Nucleocapsid Bearing an Immunodominant Region from Hepatitis B Virus Surface Antigen,* 67(6) Journal of Virology 3696-3701 (Jun. 1993).
Chang et al., *Effects of Insertional and Point Mutations on the Functions of the Duck Hepatitis B Virus Polymerase,* 64(11) Journal of Virology 5553-5558 (Nov. 1990).
Chen et al., *Amino acids essential for RNase H Activity Of Hepadnaviruses Are Also Required For Efficient Elongation Of Minus-Strand Viral DNA,* 70(9) Journal of Virology 6151-6156 (Sep. 1996).

(Continued)

*Primary Examiner* — Christian L Fronda
(74) *Attorney, Agent, or Firm* — Panitch Schwarze Belisario & Nadel LLP

(57) ABSTRACT

The present invention relates to polymerase HBV mutant polypeptides comprising a mutated polymerase domain which is functionally disrupted for polymerase activity and fusion proteins comprising such polymerase mutant polypeptide. The present invention also relates to a nucleic acid molecule and an expression vector for expressing said polymerase mutant polypeptide as well as a composition which can be used for eliciting an immune response to HBV with the goal of providing a protective or therapeutic effect against HBV infection.

26 Claims, 16 Drawing Sheets

Specification includes a Sequence Listing.

(56) References Cited

OTHER PUBLICATIONS

Choi et al., *Expression of the active human and duck hepatitis B virus polymerases in heterologous system of* Pichia methanolica, 55 Antiviral Research 279-290 (2002).
Chica et al., *Semi-rational approaches to engineering enzyme activity: combining the benefits of directed evolution and rational design,* 16 Current Opinion in Biotechnology 378-384 (2005).
Depla et al., *Rational Design of a Multiepitope Vaccine Encoding T-Lymphocyte Epitopes for Treatment of Chronic Hepatitis B Virus Infections,* 82(1) Journal of Virology 435-450 (Jan. 2008).
Desombere et al., *Characterization of the T cell recognition of hepatitis B surface antigen (HBsAg) by good and poor responders to hepatitis B vaccines,* 122 Clinical and Experimental Immunology 390-399 (2000).
Fissolo et al., *DNA vaccines prime CD8+ T cell responses to epitopes of viral antigens produced from overlapping reading frames of a single coding sequence,* 35 Eur. J. Immunol. 117-127 (2005).
Kakimi et al., *Immunogenicity and Tolerogenicity of Hepatitis B Virus Structural and Nonstructural Proteins: Implications for Immunotherapy of Persistent Viral Infections,* 76(17) Journal of Virology 8609-8620 (Sep. 2002).
Kim et al., *Increased* in vivo *immunological potency of HB-110, a novel therapeutic HBV DNA vaccine, by electroporation,* 40(6) Experimental and Molecular Medicine 669-676 (Dec. 2008).
Lee et al., *RNase H Activity of Human Hepatitis B Virus Polymerase Expressed in Escherichia coli,* 233 Biochemical and Biophysical Research Communications 401-407 (1997).
Li et al., *Discrepancy of potential antiviral resistance mutation profiles within the HBV reverse transcriptase between nucleos(t)ide analogue-untreated and -treated patients with hepatitis B in a hospital in China,* 84(2) J. Med. Virol. 207-216 (Feb. 2012).
Livingston et al., *A Rational Strategy to Design Multiepitope Immunogens Based on Multiple Th Lymphocyte Epitopes,* The Journal of Immunology 5499-5506 (2002).
Loirat et al., *Multiepitopic HLA-A*0201-Restricted Immune Response Against Hepatitis B Surface Antigen After DNA-Based Immunization,* 165 J Immunol 4748-4755 (2000).
Mancini-Bourgine et al., *Immunogenicity of a hepatitis B DNA vaccine administered to chronic HBV carriers,* 24 Vaccine 4482-4489 (2006).
Ono-Nita et al., *YMDD Motif in Hepatitis B Virus DNA Polymerase Influences on Replication and Lamivudine Resistance: A Study by* In Vitro *Full-Length viral DNA Transfection,* 29(3) Hepatology 939-945 (1999).
Pumpens et al., *Hepatitis B Virus Core Particles as Epitope Carriers,* 38 Intervirology 63-74 (1995).
Radziwill et al., *Mutational Analysis of the Hepatitis B Virus P Gene Product: Domain Structure and RNase H Activity,* 64(2) Journal of Virology 613-620 (Feb. 1990).
Rodriguez et al., *Characterization of the dynamics of hepatitis B virus resistance to adefovir by ultra-deep pyrosequencing,* 58(3) Hepatology 890-901 (Sep. 2013).
Schirmbeck et al., *The Immunodominant, $L^d$ -Restricted T Cell Response to Hepatitis B Surface Antigen (HBsAg) Efficiently Suppresses T Cell Priming to Multiple $D^d$-, $K^d$-, and $K^b$-Restricted HBsAg Epitopes,* 168 Journal of Immunology 6253-6262 (2002).
Schodel et al., *The Position of Heterologous Epitopes Inserted in Hepatitis B Virus Core Particles Determines Their Immunogenicity,* 66(1) Journal of Virology 106-114 (Jan. 1992).
Sen et al., *Developments in Directed Evolution for Improving Enzyme Functions,* 143 Appl Biochem Biotechnol 212-223 (2007).
Singh et al., *Protein Engineering Approaches in the Post-Genomic Era,* 18 Curr. Protein Pept. Sci. 1-11 (2017).
Wang et al., *Hepatitis B Virus Polymerase Blocks Pattern Recognition Receptor Signaling via Interaction with DDX3: Implications for Immune Evasion,* 6(7) PLOS Pathogens 1-11 (Jul. 2010).
Yang et al., *Correlation of antiviral T-cell responses with suppression of viral rebound in chronic hepatitis B carriers: a proof-of-concept study,* 13 Gene Therapy 1110-1117 (2006).
Yang et al., *Profile of HBV antiviral resistance mutations with distinct evolutionary pathways against nucleoside/nucleotide analogue treatment among Chinese chronic hepatitis B patients,* 15(8) Antivir Ther. 1171-1178 (2010).
Yon et al., *Stimulation of specific immune response to simian immunodeficiency virus using chimeric hepatitis B core antigen particles,* 73 Journal of General Virology 2569-2575 (1992).
Zheng et al., *Prevalence and significance of Hepatitis B reverse transcriptase mutants in different disease stages of untreated patients,* 32(10) Liver Int. 1535-1542 (Nov. 2012).
Zanetti et al., *The global impact of vaccination against hepatitis B: A historical overview,* 26 Vaccine 6266-6273 (2008).
Zoulim, *Hepatitis B virus resistance to nucleos(t)ide analogues,* 137 Gastroenterology 1593-1608 (2009).
International Search Report and Written Opinion dated Oct. 16, 2013, in PCT Application No. PCT/EP2012/063640.
Colvin et al., *Hepatitis and Liver Cancer: A National Strategy for Prevention and Control of Hepatitis B and C,* The National Academies (2010) (Book).
Kim et al., *Prevention of Hepatocellular Carcinoma in Patients with Chronic Hepatitis B Virus Infection,* 81(suppl. 1) Oncology 41-49 (2011).
Michielsen et al., *Viral hepatitis B and hepatocellular carcinoma,* LXXIV Acta Gastro-Enterologica Belgica 4-8 (Jan.-Mar. 2011).
Taylor et al., *Clinical Outcomes in Adults with Chronic Hepatitis B in Association with Patient and Viral Characteristics: A Systematic Review of Evidence,* 49(5) Hepatology 585-595 (2011).

* cited by examiner

PC2
PC1
% of IFNg+ CD8+ T cells specfic of HBV Core
10
9
8
7
6
5
4
3
2
1
0
1.1 1.3 1.2 1.5 1.6 1.8 1.7 1.4 Mean
2.4 2.6 2.8 2.2 2.5 2.3 2.1 2.7 Mean
3.3 3.2 3.8 3.4 3.5 3.1 3.6 3.7 Mean
Empty
Core-Pol
Core-Pol-Env1-Pol-Env2-Pol PC2
PC1
% of IFNg+ CD4+ T cells specific of HBV Core
0,35
0,3
0,25
0,2
0,15
0,1
0,05
0
1.8 1.1 1.2 1.5 1.4 1.6 1.3 1.7 Mean
2.6 2.8 2.4 2.2 2.1 2.5 2.7 2.3 Mean
3.8 3.2 3.3 3.4 3.5 3.1 3.6 3.7 Mean
Empty
Core-Pol
Core-Pol-Env1-Pol-Env2-Pol % of IFNg+ CD8+ T cells specific of HBV Pol
PP8
PP7
PP6
PP5
PP4
PP3
PP2
PP1
0
1
2
3
4
5
1.2 1.5 1.6 1.3 1.1 1.4 1.7 1.8 Mean
2.2 2.8 2.6 2.4 2.5 2.1 2.7 2.3 Mean
3.4 3.3 3.8 3.5 3.2 3.6 3.1 3.7 Mean
Empty
Core-Pol
Core-Pol-Env1-Pol-Env2-Pol % of IFNg+ CD4+ T cells specific of HBV Pol
PP8
PP7
PP6
PP5
PP4
PP3
PP2
PP1
0
0,05
0,1
0,15
0,2
0,25
0,3
0,35
1.8 1.5 1.6 1.3 1.2 1.4 1.7 1.1 Mean
2.6 2.8 2.4 2.2 2.1 2.7 2.5 2.3 Mean
3.4 3.3 3.8 3.2 3.1 3.6 3.7 3.5 Mean
Empty
Core-Pol
Core-Pol-Env1-Pol-Env2-Pol

SEQUENCE LISTING

```
<160> NUMBER OF SEQ ID NOS: 26

<210> SEQ ID NO 1
<211> LENGTH: 344
<212> TYPE: PRT
<213> ORGANISM: Hepatitis B virus
<220> FEATURE:
<221> NAME/KEY: misc_feature
<222> LOCATION: (7)..(7)
<223> OTHER INFORMATION: Xaa (7) can be Thr (T) or Ala (A)
<220> FEATURE:
<221> NAME/KEY: misc_feature
<222> LOCATION: (13)..(13)
<223> OTHER INFORMATION: Xaa (13) can be Asn (N), Arg (R) or His (H)
<220> FEATURE:
<221> NAME/KEY: misc_feature
<222> LOCATION: (16)..(16)
<223> OTHER INFORMATION: Xaa (16) can be Ile (I) or Thr (T)
<220> FEATURE:
<221> NAME/KEY: misc_feature
<222> LOCATION: (38)..(38)
<223> OTHER INFORMATION: Xaa (38) can be Thr (T) or Ala (A)
<220> FEATURE:
<221> NAME/KEY: misc_feature
<222> LOCATION: (53)..(53)
<223> OTHER INFORMATION: Xaa (53) can be Ser (S) or Asn (N)
<220> FEATURE:
<221> NAME/KEY: misc_feature
<222> LOCATION: (54)..(54)
<223> OTHER INFORMATION: Xaa (54) can be Thr (T) or Tyr (Y)
<220> FEATURE:
<221> NAME/KEY: misc_feature
<222> LOCATION: (55)..(55)
<223> OTHER INFORMATION: Xaa (55) can be His (H) or Arg (R)
<220> FEATURE:
<221> NAME/KEY: misc_feature
<222> LOCATION: (91)..(91)
<223> OTHER INFORMATION: Xaa (91) can be Ile (I) or Leu (L)
<220> FEATURE:
<221> NAME/KEY: misc_feature
<222> LOCATION: (109)..(109)
<223> OTHER INFORMATION: Xaa (109) can be Pro (P) or Ser (S)
<220> FEATURE:
<221> NAME/KEY: misc_feature
<222> LOCATION: (118)..(118)
<223> OTHER INFORMATION: Xaa (118) can be Thr (T) or Asn (N)
<220> FEATURE:
<221> NAME/KEY: misc_feature
<222> LOCATION: (121)..(121)
<223> OTHER INFORMATION: Xaa (121) can be Asn (N) or Ile (I)
<220> FEATURE:
<221> NAME/KEY: misc_feature
<222> LOCATION: (122)..(122)
<223> OTHER INFORMATION: Xaa (122) can be Ile (I) or Phe (F)
<220> FEATURE:
<221> NAME/KEY: misc_feature
<222> LOCATION: (124)..(124)
<223> OTHER INFORMATION: Xaa (124) can be Tyr (Y) or Asn (N)
<220> FEATURE:
<221> NAME/KEY: misc_feature
<222> LOCATION: (127)..(127)
<223> OTHER INFORMATION: Xaa (127) can be Gly (G) or Arg (R)
<220> FEATURE:
<221> NAME/KEY: misc_feature
<222> LOCATION: (131)..(131)
<223> OTHER INFORMATION: Xaa (131) can be Asp (D) or Asn (N)
<220> FEATURE:
<221> NAME/KEY: misc_feature
<222> LOCATION: (134)..(134)
<223> OTHER INFORMATION: Xaa (134) can be Asp (D) or Asn (N)
<220> FEATURE:
<221> NAME/KEY: misc_feature
<222> LOCATION: (145)..(145)
<223> OTHER INFORMATION: Xaa (145) can be Leu (L) or Met (M)
<220> FEATURE:
```

<221> NAME/KEY: misc_feature
<222> LOCATION: (149)..(149)
<223> OTHER INFORMATION: Xaa (149) can be Lys (K) or Gln (Q)
<220> FEATURE:
<221> NAME/KEY: misc_feature
<222> LOCATION: (151)..(151)
<223> OTHER INFORMATION: Xaa (151) can be Phe (F) or Tyr (Y)
<220> FEATURE:
<221> NAME/KEY: misc_feature
<222> LOCATION: (221)..(221)
<223> OTHER INFORMATION: Xaa (221) can be Phe (F) or Tyr (Y)
<220> FEATURE:
<221> NAME/KEY: misc_feature
<222> LOCATION: (222)..(222)
<223> OTHER INFORMATION: Xaa (222) can be Thr (T) or Ala (A)
<220> FEATURE:
<221> NAME/KEY: misc_feature
<222> LOCATION: (223)..(223)
<223> OTHER INFORMATION: Xaa (223) can be Ser (S) or Ala (A)
<220> FEATURE:
<221> NAME/KEY: misc_feature
<222> LOCATION: (224)..(224)
<223> OTHER INFORMATION: Xaa (224) can be Ile (I) or Val (V)
<220> FEATURE:
<221> NAME/KEY: misc_feature
<222> LOCATION: (238)..(238)
<223> OTHER INFORMATION: Xaa (238) can be Asn (N) or His (H)
<220> FEATURE:
<221> NAME/KEY: misc_feature
<222> LOCATION: (248)..(248)
<223> OTHER INFORMATION: Xaa (248) can be Asn (N) or His (H)
<220> FEATURE:
<221> NAME/KEY: misc_feature
<222> LOCATION: (256)..(256)
<223> OTHER INFORMATION: Xaa (256) can be Ser (S) or Cys (C)
<220> FEATURE:
<221> NAME/KEY: misc_feature
<222> LOCATION: (257)..(257)
<223> OTHER INFORMATION: Xaa (257) can be Trp (W) or Tyr (Y)
<220> FEATURE:
<221> NAME/KEY: misc_feature
<222> LOCATION: (259)..(259)
<223> OTHER INFORMATION: Xaa (259) can be Thr (T) or Ser (S)
<220> FEATURE:
<221> NAME/KEY: misc_feature
<222> LOCATION: (263)..(263)
<223> OTHER INFORMATION: Xaa (263) can be Glu (E) or Asp (D)
<220> FEATURE:
<221> NAME/KEY: misc_feature
<222> LOCATION: (266)..(266)
<223> OTHER INFORMATION: Xaa (266) can be Val (V) or Ile (I)
<220> FEATURE:
<221> NAME/KEY: misc_feature
<222> LOCATION: (267)..(267)
<223> OTHER INFORMATION: Xaa (267) can be Leu (L) or Gln (Q)
<220> FEATURE:
<221> NAME/KEY: misc_feature
<222> LOCATION: (271)..(271)
<223> OTHER INFORMATION: Xaa (271) can be Gln (Q), Met (M) or Glu (E)
<220> FEATURE:
<221> NAME/KEY: misc_feature
<222> LOCATION: (317)..(317)
<223> OTHER INFORMATION: Xaa (317) can be Ser (S) or Ala (A)
<220> FEATURE:
<221> NAME/KEY: misc_feature
<222> LOCATION: (332)..(332)
<223> OTHER INFORMATION: Xaa (332) can be Cys (C) or Ser (S)

<400> SEQUENCE: 1

```
Glu Asp Trp Gly Pro Cys Xaa Glu His Gly Glu His Xaa Ile Arg Xaa
1               5                   10                  15

Pro Arg Thr Pro Ala Arg Val Thr Gly Gly Val Phe Leu Val Asp Lys
            20                  25                  30

Asn Pro His Asn Thr Xaa Glu Ser Arg Leu Val Val Asp Phe Ser Gln
        35                  40                  45
```

-continued

```
Phe Ser Arg Gly Xaa Xaa Xaa Val Ser Trp Pro Lys Phe Ala Val Pro
    50                  55                  60

Asn Leu Gln Ser Leu Thr Asn Leu Leu Ser Ser Asn Leu Ser Trp Leu
65                  70                  75                  80

Ser Leu Asp Val Ser Ala Ala Phe Tyr His Xaa Pro Leu His Pro Ala
                85                  90                  95

Ala Met Pro His Leu Leu Val Gly Ser Ser Gly Leu Xaa Arg Tyr Val
            100                 105                 110

Ala Arg Leu Ser Ser Xaa Ser Arg Xaa Xaa Asn Xaa Gln His Xaa Thr
        115                 120                 125

Met Gln Xaa Leu His Xaa Ser Cys Ser Arg Asn Leu Tyr Val Ser Leu
    130                 135                 140

Xaa Leu Leu Tyr Xaa Thr Xaa Gly Arg Lys Leu His Leu Tyr Ser His
145                 150                 155                 160

Pro Ile Ile Leu Gly Phe Arg Lys Ile Pro Met Gly Val Gly Leu Ser
                165                 170                 175

Pro Phe Leu Leu Ala Gln Phe Thr Ser Ala Ile Cys Ser Val Val Arg
            180                 185                 190

Arg Ala Phe Pro His Cys Leu Ala Phe Ser Tyr Met Asp Asp Val Val
        195                 200                 205

Leu Gly Ala Lys Ser Val Gln His Leu Glu Ser Leu Xaa Xaa Xaa Xaa
    210                 215                 220

Thr Asn Phe Leu Leu Ser Leu Gly Ile His Leu Asn Pro Xaa Lys Thr
225                 230                 235                 240

Lys Arg Trp Gly Tyr Ser Leu Xaa Phe Met Gly Tyr Val Ile Gly Xaa
                245                 250                 255

Xaa Gly Xaa Leu Pro Gln Xaa His Ile Xaa Xaa Lys Ile Lys Xaa Cys
            260                 265                 270

Phe Arg Lys Leu Pro Val Asn Arg Pro Ile Asp Trp Lys Val Cys Gln
        275                 280                 285

Arg Ile Val Gly Leu Leu Gly Phe Ala Ala Pro Phe Thr Gln Cys Gly
    290                 295                 300

Tyr Pro Ala Leu Met Pro Leu Tyr Ala Cys Ile Gln Xaa Lys Gln Ala
305                 310                 315                 320

Phe Thr Phe Ser Pro Thr Tyr Lys Ala Phe Leu Xaa Lys Gln Tyr Leu
                325                 330                 335

Asn Leu Tyr Pro Val Ala Arg Gln
            340
```

<210> SEQ ID NO 2
<211> LENGTH: 337
<212> TYPE: PRT
<213> ORGANISM: artificial sequence
<220> FEATURE:
<223> OTHER INFORMATION: mutated Y07587 polymerase domain (del YMDDVVL)

<400> SEQUENCE: 2

```
Glu Asp Trp Gly Pro Cys Ala Glu His Gly Glu His His Ile Arg Ile
1               5                   10                  15

Pro Arg Thr Pro Ala Arg Val Thr Gly Gly Val Phe Leu Val Asp Lys
            20                  25                  30

Asn Pro His Asn Thr Ala Glu Ser Arg Leu Val Val Asp Phe Ser Gln
        35                  40                  45

Phe Ser Arg Gly Asn Tyr Arg Val Ser Trp Pro Lys Phe Ala Val Pro
    50                  55                  60
```

Asn Leu Gln Ser Leu Thr Asn Leu Leu Ser Ser Asn Leu Ser Trp Leu
65 70 75 80

Ser Leu Asp Val Ser Ala Ala Phe Tyr His Leu Pro Leu His Pro Ala
85 90 95

Ala Met Pro His Leu Leu Val Gly Ser Ser Gly Leu Ser Arg Tyr Val
100 105 110

Ala Arg Leu Ser Ser Asn Ser Arg Ile Phe Asn Tyr Gln His Gly Thr
115 120 125

Met Gln Asn Leu His Asp Ser Cys Ser Arg Asn Leu Tyr Val Ser Leu
130 135 140

Leu Leu Leu Tyr Gln Thr Phe Gly Arg Lys Leu His Leu Tyr Ser His
145 150 155 160

Pro Ile Ile Leu Gly Phe Arg Lys Ile Pro Met Gly Val Gly Leu Ser
165 170 175

Pro Phe Leu Leu Ala Gln Phe Thr Ser Ala Ile Cys Ser Val Val Arg
180 185 190

Arg Ala Phe Pro His Cys Leu Ala Phe Ser Gly Ala Lys Ser Val Gln
195 200 205

His Leu Glu Ser Leu Phe Thr Ala Val Thr Asn Phe Leu Leu Ser Leu
210 215 220

Gly Ile His Leu Asn Pro Asn Lys Thr Lys Arg Trp Gly Tyr Ser Leu
225 230 235 240

His Phe Met Gly Tyr Val Ile Gly Cys Tyr Gly Ser Leu Pro Gln Asp
245 250 255

His Ile Ile Gln Lys Ile Lys Glu Cys Phe Arg Lys Leu Pro Val Asn
260 265 270

Arg Pro Ile Asp Trp Lys Val Cys Gln Arg Ile Val Gly Leu Leu Gly
275 280 285

Phe Ala Ala Pro Phe Thr Gln Cys Gly Tyr Pro Ala Leu Met Pro Leu
290 295 300

Tyr Ala Cys Ile Gln Ser Lys Gln Ala Phe Thr Phe Ser Pro Thr Tyr
305 310 315 320

Lys Ala Phe Leu Cys Lys Gln Tyr Leu Asn Leu Tyr Pro Val Ala Arg
325 330 335

Gln

<210> SEQ ID NO 3
<211> LENGTH: 153
<212> TYPE: PRT
<213> ORGANISM: Hepatitis B virus
<220> FEATURE:
<221> NAME/KEY: misc_feature
<222> LOCATION: (2)..(2)
<223> OTHER INFORMATION: Xaa (2) can be Ser (S) or Pro (P)
<220> FEATURE:
<221> NAME/KEY: misc_feature
<222> LOCATION: (19)..(19)
<223> OTHER INFORMATION: Xaa (19) can be Ala (A) or Val (V)
<220> FEATURE:
<221> NAME/KEY: misc_feature
<222> LOCATION: (20)..(20)
<223> OTHER INFORMATION: Xaa (20) can be Ile (I) or Met (M)
<220> FEATURE:
<221> NAME/KEY: misc_feature
<222> LOCATION: (30)..(30)
<223> OTHER INFORMATION: Xaa (30) can be Val (V) or Leu (L)
<220> FEATURE:
<221> NAME/KEY: misc_feature
<222> LOCATION: (31)..(31)
<223> OTHER INFORMATION: Xaa (31) can be Ala (A) or Ser (S)
<220> FEATURE:

<221> NAME/KEY: misc_feature
<222> LOCATION: (53)..(53)
<223> OTHER INFORMATION: Xaa (53) can be Lys (K) or Asn (N)
<220> FEATURE:
<221> NAME/KEY: misc_feature
<222> LOCATION: (54)..(54)
<223> OTHER INFORMATION: Xaa (54) can be Leu (L) or Ile (I)
<220> FEATURE:
<221> NAME/KEY: misc_feature
<222> LOCATION: (55)..(55)
<223> OTHER INFORMATION: Xaa (55) can be Leu (L) or Ile (I)
<220> FEATURE:
<221> NAME/KEY: misc_feature
<222> LOCATION: (97)..(97)
<223> OTHER INFORMATION: Xaa (97) can be Ala (A) or Thr (T)
<220> FEATURE:
<221> NAME/KEY: misc_feature
<222> LOCATION: (108)..(108)
<223> OTHER INFORMATION: Xaa (108) can be Tyr (Y) or Ser (S)
<220> FEATURE:
<221> NAME/KEY: misc_feature
<222> LOCATION: (115)..(115)
<223> OTHER INFORMATION: Xaa (115) can be Pro (P) or Leu (L)
<220> FEATURE:
<221> NAME/KEY: misc_feature
<222> LOCATION: (116)..(116)
<223> OTHER INFORMATION: Xaa (116) can be Phe (F) or Tyr (Y)
<220> FEATURE:
<221> NAME/KEY: misc_feature
<222> LOCATION: (128)..(128)
<223> OTHER INFORMATION: Xaa (128) can be Val (V) or Asp (D)

<400> SEQUENCE: 3

```
Arg Xaa Gly Leu Cys Gln Val Phe Ala Asp Ala Thr Pro Thr Gly Trp
1               5                   10                  15

Gly Leu Xaa Xaa Gly His Gln Arg Met Arg Gly Thr Phe Xaa Xaa Pro
            20                  25                  30

Leu Pro Ile His Thr Ala Glu Leu Leu Ala Ala Cys Phe Ala Arg Ser
        35                  40                  45

Arg Ser Gly Ala Xaa Xaa Xaa Gly Thr Asp Asn Ser Val Val Leu Ser
    50                  55                  60

Arg Lys Tyr Thr Ser Phe Pro Trp Leu Leu Gly Cys Ala Ala Asn Trp
65                  70                  75                  80

Ile Leu Arg Gly Thr Ser Phe Val Tyr Val Pro Ser Ala Leu Asn Pro
                85                  90                  95

Xaa Asp Asp Pro Ser Arg Gly Arg Leu Gly Leu Xaa Arg Pro Leu Leu
            100                 105                 110

Arg Leu Xaa Xaa Arg Pro Thr Thr Gly Arg Thr Ser Leu Tyr Ala Xaa
        115                 120                 125

Ser Pro Ser Val Pro Ser His Leu Pro Asp Arg Val His Phe Ala Ser
    130                 135                 140

Pro Leu His Val Ala Trp Arg Pro Pro
145                 150
```

<210> SEQ ID NO 4
<211> LENGTH: 120
<212> TYPE: PRT
<213> ORGANISM: artificial sequence
<220> FEATURE:
<223> OTHER INFORMATION: mutated Y07587 RNaseH domain (deletion 710-742 ; substitution D689H V769Y T776Y D777H)

<400> SEQUENCE: 4

```
Arg Pro Gly Leu Cys Gln Val Phe Ala His Ala Thr Pro Thr Gly Trp
1               5                   10                  15

Gly Leu Val Met Gly His Gln Arg Met Arg Gly Thr Phe Leu Ser Arg
```

```
            20                  25                  30

Lys Tyr Thr Ser Phe Pro Trp Leu Leu Gly Cys Ala Ala Asn Trp Ile
        35                  40                  45

Leu Arg Gly Thr Ser Phe Val Tyr Tyr Pro Ser Ala Leu Asn Pro Tyr
    50                  55                  60

His Asp Pro Ser Arg Gly Arg Leu Gly Leu Ser Arg Pro Leu Leu Arg
65                  70                  75                  80

Leu Pro Phe Arg Pro Thr Thr Gly Arg Thr Ser Leu Tyr Ala Asp Ser
                85                  90                  95

Pro Ser Val Pro Ser His Leu Pro Asp Arg Val His Phe Ala Ser Pro
            100                 105                 110

Leu His Val Ala Trp Arg Pro Pro
        115                 120


<210> SEQ ID NO 5
<211> LENGTH: 792
<212> TYPE: PRT
<213> ORGANISM: artificial sequence
<220> FEATURE:
<223> OTHER INFORMATION: Y07587 polymerase with mutated polymerase and
      RNaseH domains

<400> SEQUENCE: 5

Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Lys Leu Gln His Gly Ala Glu Ser Phe His Gln Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Ile His Pro Thr Ala
225                 230                 235                 240

Arg Arg Ser Phe Gly Val Glu Pro Ser Gly Ser Gly His Ser Thr Asn
                245                 250                 255
```

-continued

```
Leu Ala Ser Lys Ser Ala Ser Cys Leu Tyr Gln Ser Pro Val Arg Lys
            260                 265                 270

Ala Ala Tyr Pro Ala Val Ser Thr Phe Glu Lys His Ser Ser Ser Gly
        275                 280                 285

His Ala Val Glu Leu His Asn Leu Pro Pro Asn Ser Ala Arg Ser Gln
    290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser His Ile Val Asn Leu Leu Glu
                325                 330                 335

Asp Trp Gly Pro Cys Ala Glu His Gly Glu His His Ile Arg Ile Pro
            340                 345                 350

Arg Thr Pro Ala Arg Val Thr Gly Gly Val Phe Leu Val Asp Lys Asn
        355                 360                 365

Pro His Asn Thr Ala Glu Ser Arg Leu Val Val Asp Phe Ser Gln Phe
    370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415

Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
        435                 440                 445

Arg Leu Ser Ser Asn Ser Arg Ile Phe Asn Tyr Gln His Gly Thr Met
    450                 455                 460

Gln Asn Leu His Asp Ser Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                485                 490                 495

Ile Ile Leu Gly Phe Arg Lys Ile Pro Met Gly Val Gly Leu Ser Pro
            500                 505                 510

Phe Leu Leu Ala Gln Phe Thr Ser Ala Ile Cys Ser Val Val Arg Arg
        515                 520                 525

Ala Phe Pro His Cys Leu Ala Phe Ser Gly Ala Lys Ser Val Gln His
    530                 535                 540

Leu Glu Ser Leu Phe Thr Ala Val Thr Asn Phe Leu Leu Ser Leu Gly
545                 550                 555                 560

Ile His Leu Asn Pro Asn Lys Thr Lys Arg Trp Gly Tyr Ser Leu His
                565                 570                 575

Phe Met Gly Tyr Val Ile Gly Cys Tyr Gly Ser Leu Pro Gln Asp His
            580                 585                 590

Ile Ile Gln Lys Ile Lys Glu Cys Phe Arg Lys Leu Pro Val Asn Arg
        595                 600                 605

Pro Ile Asp Trp Lys Val Cys Gln Arg Ile Val Gly Leu Leu Gly Phe
    610                 615                 620

Ala Ala Pro Phe Thr Gln Cys Gly Tyr Pro Ala Leu Met Pro Leu Tyr
625                 630                 635                 640

Ala Cys Ile Gln Ser Lys Gln Ala Phe Thr Phe Ser Pro Thr Tyr Lys
                645                 650                 655

Ala Phe Leu Cys Lys Gln Tyr Leu Asn Leu Tyr Pro Val Ala Arg Gln
            660                 665                 670

Arg Pro Gly Leu Cys Gln Val Phe Ala His Ala Thr Pro Thr Gly Trp
```

```
        675                 680                 685

Gly Leu Val Met Gly His Gln Arg Met Arg Gly Thr Phe Leu Ser Arg
    690                 695                 700

Lys Tyr Thr Ser Phe Pro Trp Leu Leu Gly Cys Ala Ala Asn Trp Ile
705                 710                 715                 720

Leu Arg Gly Thr Ser Phe Val Tyr Tyr Pro Ser Ala Leu Asn Pro Tyr
                725                 730                 735

His Asp Pro Ser Arg Gly Arg Leu Gly Leu Ser Arg Pro Leu Leu Arg
            740                 745                 750

Leu Pro Phe Arg Pro Thr Thr Gly Arg Thr Ser Leu Tyr Ala Asp Ser
        755                 760                 765

Pro Ser Val Pro Ser His Leu Pro Asp Arg Val His Phe Ala Ser Pro
    770                 775                 780

Leu His Val Ala Trp Arg Pro Pro
785                 790


<210> SEQ ID NO 6
<211> LENGTH: 939
<212> TYPE: PRT
<213> ORGANISM: artificial sequence
<220> FEATURE:
<223> OTHER INFORMATION: fusion between a truncated version of HBc
      (1-148) and the mutated Y07587 polymerase

<400> SEQUENCE: 6

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Pro Leu Ser Tyr Gln His Phe Arg Arg Leu Leu Leu
145                 150                 155                 160

Leu Asp Asp Glu Ala Gly Pro Leu Glu Glu Glu Leu Pro Arg Leu Ala
                165                 170                 175

Asp Glu Gly Leu Asn Arg Arg Val Ala Glu Asp Leu Asn Leu Gly Asn
            180                 185                 190

Leu Asn Val Ser Ile Pro Trp Thr His Lys Val Gly Asn Phe Thr Gly
        195                 200                 205

Leu Tyr Ser Ser Thr Val Pro Val Phe Asn Pro His Trp Lys Thr Pro
    210                 215                 220

Ser Phe Pro Asn Ile His Leu His Gln Asp Ile Ile Lys Lys Cys Glu
225                 230                 235                 240
```

-continued

```
Gln Phe Val Gly Pro Leu Thr Val Asn Glu Lys Arg Arg Leu Gln Leu
                245                 250                 255

Ile Met Pro Ala Arg Phe Tyr Pro Asn Val Thr Lys Tyr Leu Pro Leu
            260                 265                 270

Asp Lys Gly Ile Lys Pro Tyr Tyr Pro Glu His Leu Val Asn His Tyr
        275                 280                 285

Phe Gln Thr Arg His Tyr Leu His Thr Leu Trp Lys Ala Gly Ile Leu
    290                 295                 300

Tyr Lys Arg Glu Thr Thr His Ser Ala Ser Phe Cys Gly Ser Pro Tyr
305                 310                 315                 320

Ser Trp Glu Gln Lys Leu Gln His Gly Ala Glu Ser Phe His Gln Gln
                325                 330                 335

Ser Ser Gly Ile Leu Ser Arg Pro Pro Val Gly Ser Ser Leu Gln Ser
            340                 345                 350

Lys His Arg Lys Ser Arg Leu Gly Leu Gln Ser Gln Gln Gly His Leu
        355                 360                 365

Ala Arg Arg Gln Gln Gly Arg Ser Trp Ser Ile Arg Ala Gly Ile His
    370                 375                 380

Pro Thr Ala Arg Arg Ser Phe Gly Val Glu Pro Ser Gly Ser Gly His
385                 390                 395                 400

Ser Thr Asn Leu Ala Ser Lys Ser Ala Ser Cys Leu Tyr Gln Ser Pro
                405                 410                 415

Val Arg Lys Ala Ala Tyr Pro Ala Val Ser Thr Phe Glu Lys His Ser
            420                 425                 430

Ser Ser Gly His Ala Val Glu Leu His Asn Leu Pro Pro Asn Ser Ala
        435                 440                 445

Arg Ser Gln Ser Glu Arg Pro Val Phe Pro Cys Trp Trp Leu Gln Phe
    450                 455                 460

Arg Asn Ser Lys Pro Cys Ser Asp Tyr Cys Leu Ser His Ile Val Asn
465                 470                 475                 480

Leu Leu Glu Asp Trp Gly Pro Cys Ala Glu His Gly Glu His His Ile
                485                 490                 495

Arg Ile Pro Arg Thr Pro Ala Arg Val Thr Gly Gly Val Phe Leu Val
            500                 505                 510

Asp Lys Asn Pro His Asn Thr Ala Glu Ser Arg Leu Val Val Asp Phe
        515                 520                 525

Ser Gln Phe Ser Arg Gly Asn Tyr Arg Val Ser Trp Pro Lys Phe Ala
    530                 535                 540

Val Pro Asn Leu Gln Ser Leu Thr Asn Leu Leu Ser Ser Asn Leu Ser
545                 550                 555                 560

Trp Leu Ser Leu Asp Val Ser Ala Ala Phe Tyr His Leu Pro Leu His
                565                 570                 575

Pro Ala Ala Met Pro His Leu Leu Val Gly Ser Ser Gly Leu Ser Arg
            580                 585                 590

Tyr Val Ala Arg Leu Ser Ser Asn Ser Arg Ile Phe Asn Tyr Gln His
        595                 600                 605

Gly Thr Met Gln Asn Leu His Asp Ser Cys Ser Arg Asn Leu Tyr Val
    610                 615                 620

Ser Leu Leu Leu Leu Tyr Gln Thr Phe Gly Arg Lys Leu His Leu Tyr
625                 630                 635                 640

Ser His Pro Ile Ile Leu Gly Phe Arg Lys Ile Pro Met Gly Val Gly
                645                 650                 655

Leu Ser Pro Phe Leu Leu Ala Gln Phe Thr Ser Ala Ile Cys Ser Val
```

```
            660                 665                 670

Val Arg Arg Ala Phe Pro His Cys Leu Ala Phe Ser Gly Ala Lys Ser
        675                 680                 685

Val Gln His Leu Glu Ser Leu Phe Thr Ala Val Thr Asn Phe Leu Leu
    690                 695                 700

Ser Leu Gly Ile His Leu Asn Pro Asn Lys Thr Lys Arg Trp Gly Tyr
705                 710                 715                 720

Ser Leu His Phe Met Gly Tyr Val Ile Gly Cys Tyr Gly Ser Leu Pro
                725                 730                 735

Gln Asp His Ile Ile Gln Lys Ile Lys Glu Cys Phe Arg Lys Leu Pro
            740                 745                 750

Val Asn Arg Pro Ile Asp Trp Lys Val Cys Gln Arg Ile Val Gly Leu
        755                 760                 765

Leu Gly Phe Ala Ala Pro Phe Thr Gln Cys Gly Tyr Pro Ala Leu Met
    770                 775                 780

Pro Leu Tyr Ala Cys Ile Gln Ser Lys Gln Ala Phe Thr Phe Ser Pro
785                 790                 795                 800

Thr Tyr Lys Ala Phe Leu Cys Lys Gln Tyr Leu Asn Leu Tyr Pro Val
                805                 810                 815

Ala Arg Gln Arg Pro Gly Leu Cys Gln Val Phe Ala His Ala Thr Pro
            820                 825                 830

Thr Gly Trp Gly Leu Val Met Gly His Gln Arg Met Arg Gly Thr Phe
        835                 840                 845

Leu Ser Arg Lys Tyr Thr Ser Phe Pro Trp Leu Leu Gly Cys Ala Ala
    850                 855                 860

Asn Trp Ile Leu Arg Gly Thr Ser Phe Val Tyr Tyr Pro Ser Ala Leu
865                 870                 875                 880

Asn Pro Tyr His Asp Pro Ser Arg Gly Arg Leu Gly Leu Ser Arg Pro
                885                 890                 895

Leu Leu Arg Leu Pro Phe Arg Pro Thr Thr Gly Arg Thr Ser Leu Tyr
            900                 905                 910

Ala Asp Ser Pro Ser Val Pro Ser His Leu Pro Asp Arg Val His Phe
        915                 920                 925

Ala Ser Pro Leu His Val Ala Trp Arg Pro Pro
    930                 935


<210> SEQ ID NO 7
<211> LENGTH: 860
<212> TYPE: PRT
<213> ORGANISM: artificial sequence
<220> FEATURE:
<223> OTHER INFORMATION: fusion mutated Y07587 polymerase with env1 and
      env2 immunogenic domains

<400> SEQUENCE: 7

Met Pro Leu Ser Tyr Gln His Phe Arg Arg Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80
```

-continued

```
Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
            100                 105                 110

Ala Arg Phe Tyr Pro Asn Val Thr Lys Tyr Leu Pro Leu Asp Lys Gly
        115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr His Ser Ala Ser Phe Cys Gly Ser Pro Tyr Ser Trp Glu
                165                 170                 175

Gln Lys Leu Gln His Gly Ala Glu Ser Phe His Gln Gln Ser Ser Gly
            180                 185                 190

Ile Leu Ser Arg Pro Pro Val Gly Ser Ser Leu Gln Ser Lys His Arg
        195                 200                 205

Lys Ser Arg Leu Gly Leu Gln Ser Gln Gln Gly His Leu Ala Arg Arg
    210                 215                 220

Gln Gln Gly Arg Ser Trp Ser Ile Arg Ala Gly Ile His Pro Thr Ala
225                 230                 235                 240

Arg Arg Ser Phe Gly Val Glu Pro Ser Gly Ser Gly His Ser Thr Asn
                245                 250                 255

Leu Ala Ser Lys Ser Ala Ser Cys Leu Tyr Gln Ser Pro Val Arg Lys
            260                 265                 270

Ala Ala Tyr Pro Ala Val Ser Thr Phe Glu Lys His Ser Ser Ser Gly
        275                 280                 285

His Ala Val Glu Leu His Asn Leu Pro Pro Asn Ser Ala Arg Ser Gln
    290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser His Ile Val Asn Leu Leu Glu
                325                 330                 335

Asp Trp Gly Pro Cys Ala Glu His Gly Glu His His Ile Arg Ile Pro
            340                 345                 350

Arg Thr Pro Ala Arg Val Thr Gly Gly Val Phe Leu Val Asp Lys Asn
        355                 360                 365

Pro His Asn Thr Ala Glu Ser Arg Leu Val Val Asp Phe Ser Gln Phe
    370                 375                 380

Ser Arg Gly Asn Tyr Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415

Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
        435                 440                 445

Arg Leu Ser Ser Asn Ser Arg Ile Phe Asn Tyr Gln His Gly Thr Met
    450                 455                 460

Gln Asn Leu His Asp Ser Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                485                 490                 495

Ile Ile Leu Gly Phe Arg Lys Ile Pro Met Gly Val Gly Leu Ser Pro
```

```
            500                 505                 510

Phe Leu Leu Ala Gln Phe Thr Ser Ala Ile Cys Ser Val Val Arg Arg
        515                 520                 525

Ala Phe Pro His Cys Leu Ala Phe Ser Val Leu Gln Ala Gly Phe Phe
    530                 535                 540

Leu Leu Thr Arg Ile Leu Thr Ile Pro Gln Ser Leu Asp Ser Trp Trp
545                 550                 555                 560

Thr Ser Leu Asn Phe Leu Gly Gly Thr Thr Val Cys Leu Gly Gln Gly
                565                 570                 575

Ala Lys Ser Val Gln His Leu Glu Ser Leu Phe Thr Ala Val Thr Asn
            580                 585                 590

Phe Leu Leu Ser Leu Gly Ile His Leu Asn Pro Asn Lys Thr Lys Arg
        595                 600                 605

Trp Gly Tyr Ser Leu His Phe Met Gly Tyr Val Ile Gly Cys Tyr Gly
    610                 615                 620

Ser Leu Pro Gln Asp His Ile Ile Gln Lys Ile Lys Glu Cys Phe Arg
625                 630                 635                 640

Lys Leu Pro Val Asn Arg Pro Ile Asp Trp Lys Val Cys Gln Arg Ile
                645                 650                 655

Val Gly Leu Leu Gly Phe Ala Ala Pro Phe Thr Gln Cys Gly Tyr Pro
            660                 665                 670

Ala Leu Met Pro Leu Tyr Ala Cys Ile Gln Ser Lys Gln Ala Phe Thr
        675                 680                 685

Phe Ser Pro Thr Tyr Lys Ala Phe Leu Cys Lys Gln Tyr Leu Asn Leu
    690                 695                 700

Tyr Pro Val Ala Arg Gln Arg Pro Gly Leu Cys Gln Val Phe Ala His
705                 710                 715                 720

Ala Thr Pro Thr Gly Trp Gly Leu Val Met Gly His Gln Arg Met Arg
                725                 730                 735

Gly Thr Phe Leu Trp Ala Ser Ala Arg Phe Ser Trp Leu Ser Leu Leu
            740                 745                 750

Val Pro Phe Val Gln Trp Phe Val Gly Leu Ser Pro Thr Val Trp Leu
        755                 760                 765

Ser Val Ser Arg Lys Tyr Thr Ser Phe Pro Trp Leu Leu Gly Cys Ala
    770                 775                 780

Ala Asn Trp Ile Leu Arg Gly Thr Ser Phe Val Tyr Tyr Pro Ser Ala
785                 790                 795                 800

Leu Asn Pro Tyr His Asp Pro Ser Arg Gly Arg Leu Gly Leu Ser Arg
                805                 810                 815

Pro Leu Leu Arg Leu Pro Phe Arg Pro Thr Thr Gly Arg Thr Ser Leu
            820                 825                 830

Tyr Ala Asp Ser Pro Ser Val Pro Ser His Leu Pro Asp Arg Val His
        835                 840                 845

Phe Ala Ser Pro Leu His Val Ala Trp Arg Pro Pro
    850                 855                 860


<210> SEQ ID NO 8
<211> LENGTH: 1007
<212> TYPE: PRT
<213> ORGANISM: artificial sequence
<220> FEATURE:
<223> OTHER INFORMATION: fusion between truncated core (1-148)- mutated
      Y07587 polymerase - env1 and env2

<400> SEQUENCE: 8
```

-continued

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Pro Leu Ser Tyr Gln His Phe Arg Arg Leu Leu Leu
145                 150                 155                 160

Leu Asp Asp Glu Ala Gly Pro Leu Glu Glu Glu Leu Pro Arg Leu Ala
                165                 170                 175

Asp Glu Gly Leu Asn Arg Arg Val Ala Glu Asp Leu Asn Leu Gly Asn
            180                 185                 190

Leu Asn Val Ser Ile Pro Trp Thr His Lys Val Gly Asn Phe Thr Gly
        195                 200                 205

Leu Tyr Ser Ser Thr Val Pro Val Phe Asn Pro His Trp Lys Thr Pro
    210                 215                 220

Ser Phe Pro Asn Ile His Leu His Gln Asp Ile Ile Lys Lys Cys Glu
225                 230                 235                 240

Gln Phe Val Gly Pro Leu Thr Val Asn Glu Lys Arg Arg Leu Gln Leu
                245                 250                 255

Ile Met Pro Ala Arg Phe Tyr Pro Asn Val Thr Lys Tyr Leu Pro Leu
            260                 265                 270

Asp Lys Gly Ile Lys Pro Tyr Tyr Pro Glu His Leu Val Asn His Tyr
        275                 280                 285

Phe Gln Thr Arg His Tyr Leu His Thr Leu Trp Lys Ala Gly Ile Leu
    290                 295                 300

Tyr Lys Arg Glu Thr Thr His Ser Ala Ser Phe Cys Gly Ser Pro Tyr
305                 310                 315                 320

Ser Trp Glu Gln Lys Leu Gln His Gly Ala Glu Ser Phe His Gln Gln
                325                 330                 335

Ser Ser Gly Ile Leu Ser Arg Pro Pro Val Gly Ser Ser Leu Gln Ser
            340                 345                 350

Lys His Arg Lys Ser Arg Leu Gly Leu Gln Ser Gln Gln Gly His Leu
        355                 360                 365

Ala Arg Arg Gln Gln Gly Arg Ser Trp Ser Ile Arg Ala Gly Ile His
    370                 375                 380

Pro Thr Ala Arg Arg Ser Phe Gly Val Glu Pro Ser Gly Ser Gly His
385                 390                 395                 400

Ser Thr Asn Leu Ala Ser Lys Ser Ala Ser Cys Leu Tyr Gln Ser Pro
                405                 410                 415

Val Arg Lys Ala Ala Tyr Pro Ala Val Ser Thr Phe Glu Lys His Ser
```

-continued

```
            420                 425                 430

Ser Ser Gly His Ala Val Glu Leu His Asn Leu Pro Pro Asn Ser Ala
        435                 440                 445

Arg Ser Gln Ser Glu Arg Pro Val Phe Pro Cys Trp Trp Leu Gln Phe
    450                 455                 460

Arg Asn Ser Lys Pro Cys Ser Asp Tyr Cys Leu Ser His Ile Val Asn
465                 470                 475                 480

Leu Leu Glu Asp Trp Gly Pro Cys Ala Glu His Gly Glu His His Ile
                485                 490                 495

Arg Ile Pro Arg Thr Pro Ala Arg Val Thr Gly Gly Val Phe Leu Val
            500                 505                 510

Asp Lys Asn Pro His Asn Thr Ala Glu Ser Arg Leu Val Val Asp Phe
        515                 520                 525

Ser Gln Phe Ser Arg Gly Asn Tyr Arg Val Ser Trp Pro Lys Phe Ala
    530                 535                 540

Val Pro Asn Leu Gln Ser Leu Thr Asn Leu Leu Ser Ser Asn Leu Ser
545                 550                 555                 560

Trp Leu Ser Leu Asp Val Ser Ala Ala Phe Tyr His Leu Pro Leu His
                565                 570                 575

Pro Ala Ala Met Pro His Leu Leu Val Gly Ser Ser Gly Leu Ser Arg
            580                 585                 590

Tyr Val Ala Arg Leu Ser Ser Asn Ser Arg Ile Phe Asn Tyr Gln His
        595                 600                 605

Gly Thr Met Gln Asn Leu His Asp Ser Cys Ser Arg Asn Leu Tyr Val
    610                 615                 620

Ser Leu Leu Leu Leu Tyr Gln Thr Phe Gly Arg Lys Leu His Leu Tyr
625                 630                 635                 640

Ser His Pro Ile Ile Leu Gly Phe Arg Lys Ile Pro Met Gly Val Gly
                645                 650                 655

Leu Ser Pro Phe Leu Leu Ala Gln Phe Thr Ser Ala Ile Cys Ser Val
            660                 665                 670

Val Arg Arg Ala Phe Pro His Cys Leu Ala Phe Ser Val Leu Gln Ala
        675                 680                 685

Gly Phe Phe Leu Leu Thr Arg Ile Leu Thr Ile Pro Gln Ser Leu Asp
    690                 695                 700

Ser Trp Trp Thr Ser Leu Asn Phe Leu Gly Gly Thr Thr Val Cys Leu
705                 710                 715                 720

Gly Gln Gly Ala Lys Ser Val Gln His Leu Glu Ser Leu Phe Thr Ala
                725                 730                 735

Val Thr Asn Phe Leu Leu Ser Leu Gly Ile His Leu Asn Pro Asn Lys
            740                 745                 750

Thr Lys Arg Trp Gly Tyr Ser Leu His Phe Met Gly Tyr Val Ile Gly
        755                 760                 765

Cys Tyr Gly Ser Leu Pro Gln Asp His Ile Ile Gln Lys Ile Lys Glu
    770                 775                 780

Cys Phe Arg Lys Leu Pro Val Asn Arg Pro Ile Asp Trp Lys Val Cys
785                 790                 795                 800

Gln Arg Ile Val Gly Leu Leu Gly Phe Ala Ala Pro Phe Thr Gln Cys
                805                 810                 815

Gly Tyr Pro Ala Leu Met Pro Leu Tyr Ala Cys Ile Gln Ser Lys Gln
            820                 825                 830

Ala Phe Thr Phe Ser Pro Thr Tyr Lys Ala Phe Leu Cys Lys Gln Tyr
        835                 840                 845
```

```
Leu Asn Leu Tyr Pro Val Ala Arg Gln Arg Pro Gly Leu Cys Gln Val
    850                 855                 860

Phe Ala His Ala Thr Pro Thr Gly Trp Gly Leu Val Met Gly His Gln
865                 870                 875                 880

Arg Met Arg Gly Thr Phe Leu Trp Ala Ser Ala Arg Phe Ser Trp Leu
                885                 890                 895

Ser Leu Leu Val Pro Phe Val Gln Trp Phe Val Gly Leu Ser Pro Thr
            900                 905                 910

Val Trp Leu Ser Val Ser Arg Lys Tyr Thr Ser Phe Pro Trp Leu Leu
        915                 920                 925

Gly Cys Ala Ala Asn Trp Ile Leu Arg Gly Thr Ser Phe Val Tyr Tyr
    930                 935                 940

Pro Ser Ala Leu Asn Pro Tyr His Asp Pro Ser Arg Gly Arg Leu Gly
945                 950                 955                 960

Leu Ser Arg Pro Leu Leu Arg Leu Pro Phe Arg Pro Thr Thr Gly Arg
                965                 970                 975

Thr Ser Leu Tyr Ala Asp Ser Pro Ser Val Pro Ser His Leu Pro Asp
            980                 985                 990

Arg Val His Phe Ala Ser Pro Leu  His Val Ala Trp Arg  Pro Pro
        995                 1000                1005


<210> SEQ ID NO 9
<211> LENGTH: 1042
<212> TYPE: PRT
<213> ORGANISM: artificial sequence
<220> FEATURE:
<223> OTHER INFORMATION: fusion between native core (1-183) - mutated
      Y07587 polymerase - env1 and env2

<400> SEQUENCE: 9

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Gly Asn Leu Glu Asp Pro Ile
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys Pro Leu Ser Tyr Gln His Phe Arg Arg
            180                 185                 190

Leu Leu Leu Leu Asp Asp Glu Ala Gly Pro Leu Glu Glu Glu Leu Pro
```

```
        195                 200                 205

Arg Leu Ala Asp Glu Gly Leu Asn Arg Arg Val Ala Glu Asp Leu Asn
    210                 215                 220

Leu Gly Asn Leu Asn Val Ser Ile Pro Trp Thr His Lys Val Gly Asn
225                 230                 235                 240

Phe Thr Gly Leu Tyr Ser Ser Thr Val Pro Val Phe Asn Pro His Trp
                245                 250                 255

Lys Thr Pro Ser Phe Pro Asn Ile His Leu His Gln Asp Ile Ile Lys
            260                 265                 270

Lys Cys Glu Gln Phe Val Gly Pro Leu Thr Val Asn Glu Lys Arg Arg
        275                 280                 285

Leu Gln Leu Ile Met Pro Ala Arg Phe Tyr Pro Asn Val Thr Lys Tyr
    290                 295                 300

Leu Pro Leu Asp Lys Gly Ile Lys Pro Tyr Tyr Pro Glu His Leu Val
305                 310                 315                 320

Asn His Tyr Phe Gln Thr Arg His Tyr Leu His Thr Leu Trp Lys Ala
                325                 330                 335

Gly Ile Leu Tyr Lys Arg Glu Thr Thr His Ser Ala Ser Phe Cys Gly
            340                 345                 350

Ser Pro Tyr Ser Trp Glu Gln Lys Leu Gln His Gly Ala Glu Ser Phe
        355                 360                 365

His Gln Gln Ser Ser Gly Ile Leu Ser Arg Pro Pro Val Gly Ser Ser
    370                 375                 380

Leu Gln Ser Lys His Arg Lys Ser Arg Leu Gly Leu Gln Ser Gln Gln
385                 390                 395                 400

Gly His Leu Ala Arg Arg Gln Gln Gly Arg Ser Trp Ser Ile Arg Ala
                405                 410                 415

Gly Ile His Pro Thr Ala Arg Arg Ser Phe Gly Val Glu Pro Ser Gly
            420                 425                 430

Ser Gly His Ser Thr Asn Leu Ala Ser Lys Ser Ala Ser Cys Leu Tyr
        435                 440                 445

Gln Ser Pro Val Arg Lys Ala Ala Tyr Pro Ala Val Ser Thr Phe Glu
    450                 455                 460

Lys His Ser Ser Ser Gly His Ala Val Glu Leu His Asn Leu Pro Pro
465                 470                 475                 480

Asn Ser Ala Arg Ser Gln Ser Glu Arg Pro Val Phe Pro Cys Trp Trp
                485                 490                 495

Leu Gln Phe Arg Asn Ser Lys Pro Cys Ser Asp Tyr Cys Leu Ser His
            500                 505                 510

Ile Val Asn Leu Leu Glu Asp Trp Gly Pro Cys Ala Glu His Gly Glu
        515                 520                 525

His His Ile Arg Ile Pro Arg Thr Pro Ala Arg Val Thr Gly Gly Val
    530                 535                 540

Phe Leu Val Asp Lys Asn Pro His Asn Thr Ala Glu Ser Arg Leu Val
545                 550                 555                 560

Val Asp Phe Ser Gln Phe Ser Arg Gly Asn Tyr Arg Val Ser Trp Pro
                565                 570                 575

Lys Phe Ala Val Pro Asn Leu Gln Ser Leu Thr Asn Leu Leu Ser Ser
            580                 585                 590

Asn Leu Ser Trp Leu Ser Leu Asp Val Ser Ala Ala Phe Tyr His Leu
        595                 600                 605

Pro Leu His Pro Ala Ala Met Pro His Leu Leu Val Gly Ser Ser Gly
    610                 615                 620
```

-continued

```
Leu Ser Arg Tyr Val Ala Arg Leu Ser Ser Asn Ser Arg Ile Phe Asn
625                 630                 635                 640

Tyr Gln His Gly Thr Met Gln Asn Leu His Asp Ser Cys Ser Arg Asn
                645                 650                 655

Leu Tyr Val Ser Leu Leu Leu Leu Tyr Gln Thr Phe Gly Arg Lys Leu
            660                 665                 670

His Leu Tyr Ser His Pro Ile Ile Leu Gly Phe Arg Lys Ile Pro Met
        675                 680                 685

Gly Val Gly Leu Ser Pro Phe Leu Leu Ala Gln Phe Thr Ser Ala Ile
    690                 695                 700

Cys Ser Val Val Arg Arg Ala Phe Pro His Cys Leu Ala Phe Ser Val
705                 710                 715                 720

Leu Gln Ala Gly Phe Phe Leu Leu Thr Arg Ile Leu Thr Ile Pro Gln
                725                 730                 735

Ser Leu Asp Ser Trp Trp Thr Ser Leu Asn Phe Leu Gly Gly Thr Thr
            740                 745                 750

Val Cys Leu Gly Gln Gly Ala Lys Ser Val Gln His Leu Glu Ser Leu
        755                 760                 765

Phe Thr Ala Val Thr Asn Phe Leu Leu Ser Leu Gly Ile His Leu Asn
    770                 775                 780

Pro Asn Lys Thr Lys Arg Trp Gly Tyr Ser Leu His Phe Met Gly Tyr
785                 790                 795                 800

Val Ile Gly Cys Tyr Gly Ser Leu Pro Gln Asp His Ile Ile Gln Lys
                805                 810                 815

Ile Lys Glu Cys Phe Arg Lys Leu Pro Val Asn Arg Pro Ile Asp Trp
            820                 825                 830

Lys Val Cys Gln Arg Ile Val Gly Leu Leu Gly Phe Ala Ala Pro Phe
        835                 840                 845

Thr Gln Cys Gly Tyr Pro Ala Leu Met Pro Leu Tyr Ala Cys Ile Gln
    850                 855                 860

Ser Lys Gln Ala Phe Thr Phe Ser Pro Thr Tyr Lys Ala Phe Leu Cys
865                 870                 875                 880

Lys Gln Tyr Leu Asn Leu Tyr Pro Val Ala Arg Gln Arg Pro Gly Leu
                885                 890                 895

Cys Gln Val Phe Ala His Ala Thr Pro Thr Gly Trp Gly Leu Val Met
            900                 905                 910

Gly His Gln Arg Met Arg Gly Thr Phe Leu Trp Ala Ser Ala Arg Phe
        915                 920                 925

Ser Trp Leu Ser Leu Leu Val Pro Phe Val Gln Trp Phe Val Gly Leu
    930                 935                 940

Ser Pro Thr Val Trp Leu Ser Val Ser Arg Lys Tyr Thr Ser Phe Pro
945                 950                 955                 960

Trp Leu Leu Gly Cys Ala Ala Asn Trp Ile Leu Arg Gly Thr Ser Phe
                965                 970                 975

Val Tyr Tyr Pro Ser Ala Leu Asn Pro Tyr His Asp Pro Ser Arg Gly
            980                 985                 990

Arg Leu Gly Leu Ser Arg Pro Leu  Leu Arg Leu Pro Phe  Arg Pro Thr
        995                 1000                1005

Thr Gly  Arg Thr Ser Leu Tyr  Ala Asp Ser Pro Ser  Val Pro Ser
    1010                 1015                 1020

His Leu  Pro Asp Arg Val His  Phe Ala Ser Pro Leu  His Val Ala
    1025                 1030                 1035
```

Trp Arg Pro Pro
1040

<210> SEQ ID NO 10
<211> LENGTH: 880
<212> TYPE: PRT
<213> ORGANISM: artificial sequence
<220> FEATURE:
<223> OTHER INFORMATION: fusion between signal sequence -mutated Y07587 polymerase and transmembrane sequence

<400> SEQUENCE: 10

Met Val Pro Gln Ala Leu Leu Phe Val Pro Leu Leu Val Phe Pro Leu
1 5 10 15

Cys Phe Gly Lys Phe Pro Ile Pro Leu Ser Tyr Gln His Phe Arg Arg
20 25 30

Leu Leu Leu Leu Asp Asp Glu Ala Gly Pro Leu Glu Glu Glu Leu Pro
35 40 45

Arg Leu Ala Asp Glu Gly Leu Asn Arg Arg Val Ala Glu Asp Leu Asn
50 55 60

Leu Gly Asn Leu Asn Val Ser Ile Pro Trp Thr His Lys Val Gly Asn
65 70 75 80

Phe Thr Gly Leu Tyr Ser Ser Thr Val Pro Val Phe Asn Pro His Trp
85 90 95

Lys Thr Pro Ser Phe Pro Asn Ile His Leu His Gln Asp Ile Ile Lys
100 105 110

Lys Cys Glu Gln Phe Val Gly Pro Leu Thr Val Asn Glu Lys Arg Arg
115 120 125

Leu Gln Leu Ile Met Pro Ala Arg Phe Tyr Pro Asn Val Thr Lys Tyr
130 135 140

Leu Pro Leu Asp Lys Gly Ile Lys Pro Tyr Tyr Pro Glu His Leu Val
145 150 155 160

Asn His Tyr Phe Gln Thr Arg His Tyr Leu His Thr Leu Trp Lys Ala
165 170 175

Gly Ile Leu Tyr Lys Arg Glu Thr Thr His Ser Ala Ser Phe Cys Gly
180 185 190

Ser Pro Tyr Ser Trp Glu Gln Lys Leu Gln His Gly Ala Glu Ser Phe
195 200 205

His Gln Gln Ser Ser Gly Ile Leu Ser Arg Pro Pro Val Gly Ser Ser
210 215 220

Leu Gln Ser Lys His Arg Lys Ser Arg Leu Gly Leu Gln Ser Gln Gln
225 230 235 240

Gly His Leu Ala Arg Arg Gln Gln Gly Arg Ser Trp Ser Ile Arg Ala
245 250 255

Gly Ile His Pro Thr Ala Arg Arg Ser Phe Gly Val Glu Pro Ser Gly
260 265 270

Ser Gly His Ser Thr Asn Leu Ala Ser Lys Ser Ala Ser Cys Leu Tyr
275 280 285

Gln Ser Pro Val Arg Lys Ala Ala Tyr Pro Ala Val Ser Thr Phe Glu
290 295 300

Lys His Ser Ser Ser Gly His Ala Val Glu Leu His Asn Leu Pro Pro
305 310 315 320

Asn Ser Ala Arg Ser Gln Ser Glu Arg Pro Val Phe Pro Cys Trp Trp
325 330 335

Leu Gln Phe Arg Asn Ser Lys Pro Cys Ser Asp Tyr Cys Leu Ser His
340 345 350

```
Ile Val Asn Leu Leu Glu Asp Trp Gly Pro Cys Ala Glu His Gly Glu
        355                 360                 365

His His Ile Arg Ile Pro Arg Thr Pro Ala Arg Val Thr Gly Gly Val
    370                 375                 380

Phe Leu Val Asp Lys Asn Pro His Asn Thr Ala Glu Ser Arg Leu Val
385                 390                 395                 400

Val Asp Phe Ser Gln Phe Ser Arg Gly Asn Tyr Arg Val Ser Trp Pro
                405                 410                 415

Lys Phe Ala Val Pro Asn Leu Gln Ser Leu Thr Asn Leu Leu Ser Ser
            420                 425                 430

Asn Leu Ser Trp Leu Ser Leu Asp Val Ser Ala Ala Phe Tyr His Leu
        435                 440                 445

Pro Leu His Pro Ala Ala Met Pro His Leu Leu Val Gly Ser Ser Gly
    450                 455                 460

Leu Ser Arg Tyr Val Ala Arg Leu Ser Ser Asn Ser Arg Ile Phe Asn
465                 470                 475                 480

Tyr Gln His Gly Thr Met Gln Asn Leu His Asp Ser Cys Ser Arg Asn
                485                 490                 495

Leu Tyr Val Ser Leu Leu Leu Leu Tyr Gln Thr Phe Gly Arg Lys Leu
            500                 505                 510

His Leu Tyr Ser His Pro Ile Ile Leu Gly Phe Arg Lys Ile Pro Met
        515                 520                 525

Gly Val Gly Leu Ser Pro Phe Leu Leu Ala Gln Phe Thr Ser Ala Ile
    530                 535                 540

Cys Ser Val Val Arg Arg Ala Phe Pro His Cys Leu Ala Phe Ser Gly
545                 550                 555                 560

Ala Lys Ser Val Gln His Leu Glu Ser Leu Phe Thr Ala Val Thr Asn
                565                 570                 575

Phe Leu Leu Ser Leu Gly Ile His Leu Asn Pro Asn Lys Thr Lys Arg
            580                 585                 590

Trp Gly Tyr Ser Leu His Phe Met Gly Tyr Val Ile Gly Cys Tyr Gly
        595                 600                 605

Ser Leu Pro Gln Asp His Ile Ile Gln Lys Ile Lys Glu Cys Phe Arg
    610                 615                 620

Lys Leu Pro Val Asn Arg Pro Ile Asp Trp Lys Val Cys Gln Arg Ile
625                 630                 635                 640

Val Gly Leu Leu Gly Phe Ala Ala Pro Phe Thr Gln Cys Gly Tyr Pro
                645                 650                 655

Ala Leu Met Pro Leu Tyr Ala Cys Ile Gln Ser Lys Gln Ala Phe Thr
            660                 665                 670

Phe Ser Pro Thr Tyr Lys Ala Phe Leu Cys Lys Gln Tyr Leu Asn Leu
        675                 680                 685

Tyr Pro Val Ala Arg Gln Arg Pro Gly Leu Cys Gln Val Phe Ala His
    690                 695                 700

Ala Thr Pro Thr Gly Trp Gly Leu Val Met Gly His Gln Arg Met Arg
705                 710                 715                 720

Gly Thr Phe Leu Ser Arg Lys Tyr Thr Ser Phe Pro Trp Leu Leu Gly
                725                 730                 735

Cys Ala Ala Asn Trp Ile Leu Arg Gly Thr Ser Phe Val Tyr Tyr Pro
            740                 745                 750

Ser Ala Leu Asn Pro Tyr His Asp Pro Ser Arg Gly Arg Leu Gly Leu
        755                 760                 765
```

```
Ser Arg Pro Leu Leu Arg Leu Pro Phe Arg Pro Thr Thr Gly Arg Thr
    770                 775                 780

Ser Leu Tyr Ala Asp Ser Pro Ser Val Pro Ser His Leu Pro Asp Arg
785                 790                 795                 800

Val His Phe Ala Ser Pro Leu His Val Ala Trp Arg Pro Pro Tyr Val
                805                 810                 815

Leu Leu Ser Ala Gly Ala Leu Thr Ala Leu Met Leu Ile Ile Phe Leu
            820                 825                 830

Met Thr Cys Cys Arg Arg Val Asn Arg Ser Glu Pro Thr Gln His Asn
        835                 840                 845

Leu Arg Gly Thr Gly Arg Glu Val Ser Val Thr Pro Gln Ser Gly Lys
    850                 855                 860

Ile Ile Ser Ser Trp Glu Ser His Lys Ser Gly Gly Glu Thr Arg Leu
865                 870                 875                 880


<210> SEQ ID NO 11
<211> LENGTH: 1027
<212> TYPE: PRT
<213> ORGANISM: artificial sequence
<220> FEATURE:
<223> OTHER INFORMATION: fusion between sequence signal - truncated core
      (1-148) -mutated Y07587 polymerase - sequence TM

<400> SEQUENCE: 11

Met Val Pro Gln Ala Leu Leu Phe Val Pro Leu Leu Val Phe Pro Leu
1               5                   10                  15

Cys Phe Gly Lys Phe Pro Ile Asp Ile Asp Pro Tyr Lys Glu Phe Gly
            20                  25                  30

Ala Thr Val Glu Leu Leu Ser Phe Leu Pro Ser Asp Phe Phe Pro Ser
        35                  40                  45

Val Arg Asp Leu Leu Asp Thr Ala Ser Ala Leu Tyr Arg Glu Ala Leu
    50                  55                  60

Glu Ser Pro Glu His Cys Ser Pro His His Thr Ala Leu Arg Gln Ala
65                  70                  75                  80

Ile Leu Cys Trp Gly Glu Leu Met Thr Leu Ala Thr Trp Val Gly Gly
                85                  90                  95

Asn Leu Glu Asp Pro Ile Ser Arg Asp Leu Val Val Ser Tyr Val Asn
            100                 105                 110

Thr Asn Met Gly Leu Lys Phe Arg Gln Leu Leu Trp Phe His Ile Ser
        115                 120                 125

Cys Leu Thr Phe Gly Arg Glu Thr Val Ile Glu Tyr Leu Val Ser Phe
    130                 135                 140

Gly Val Trp Ile Arg Thr Pro Pro Ala Tyr Arg Pro Pro Asn Ala Pro
145                 150                 155                 160

Ile Leu Ser Thr Leu Pro Glu Thr Thr Val Pro Leu Ser Tyr Gln His
                165                 170                 175

Phe Arg Arg Leu Leu Leu Leu Asp Asp Glu Ala Gly Pro Leu Glu Glu
            180                 185                 190

Glu Leu Pro Arg Leu Ala Asp Glu Gly Leu Asn Arg Arg Val Ala Glu
        195                 200                 205

Asp Leu Asn Leu Gly Asn Leu Asn Val Ser Ile Pro Trp Thr His Lys
    210                 215                 220

Val Gly Asn Phe Thr Gly Leu Tyr Ser Ser Thr Val Pro Val Phe Asn
225                 230                 235                 240

Pro His Trp Lys Thr Pro Ser Phe Pro Asn Ile His Leu His Gln Asp
                245                 250                 255
```

-continued

```
Ile Ile Lys Lys Cys Glu Gln Phe Val Gly Pro Leu Thr Val Asn Glu
            260                 265                 270

Lys Arg Arg Leu Gln Leu Ile Met Pro Ala Arg Phe Tyr Pro Asn Val
        275                 280                 285

Thr Lys Tyr Leu Pro Leu Asp Lys Gly Ile Lys Pro Tyr Tyr Pro Glu
    290                 295                 300

His Leu Val Asn His Tyr Phe Gln Thr Arg His Tyr Leu His Thr Leu
305                 310                 315                 320

Trp Lys Ala Gly Ile Leu Tyr Lys Arg Glu Thr Thr His Ser Ala Ser
                325                 330                 335

Phe Cys Gly Ser Pro Tyr Ser Trp Glu Gln Lys Leu Gln His Gly Ala
            340                 345                 350

Glu Ser Phe His Gln Gln Ser Ser Gly Ile Leu Ser Arg Pro Pro Val
        355                 360                 365

Gly Ser Ser Leu Gln Ser Lys His Arg Lys Ser Arg Leu Gly Leu Gln
    370                 375                 380

Ser Gln Gln Gly His Leu Ala Arg Arg Gln Gln Gly Arg Ser Trp Ser
385                 390                 395                 400

Ile Arg Ala Gly Ile His Pro Thr Ala Arg Arg Ser Phe Gly Val Glu
                405                 410                 415

Pro Ser Gly Ser Gly His Ser Thr Asn Leu Ala Ser Lys Ser Ala Ser
            420                 425                 430

Cys Leu Tyr Gln Ser Pro Val Arg Lys Ala Ala Tyr Pro Ala Val Ser
        435                 440                 445

Thr Phe Glu Lys His Ser Ser Ser Gly His Ala Val Glu Leu His Asn
    450                 455                 460

Leu Pro Pro Asn Ser Ala Arg Ser Gln Ser Glu Arg Pro Val Phe Pro
465                 470                 475                 480

Cys Trp Trp Leu Gln Phe Arg Asn Ser Lys Pro Cys Ser Asp Tyr Cys
                485                 490                 495

Leu Ser His Ile Val Asn Leu Leu Glu Asp Trp Gly Pro Cys Ala Glu
            500                 505                 510

His Gly Glu His His Ile Arg Ile Pro Arg Thr Pro Ala Arg Val Thr
        515                 520                 525

Gly Gly Val Phe Leu Val Asp Lys Asn Pro His Asn Thr Ala Glu Ser
    530                 535                 540

Arg Leu Val Val Asp Phe Ser Gln Phe Ser Arg Gly Asn Tyr Arg Val
545                 550                 555                 560

Ser Trp Pro Lys Phe Ala Val Pro Asn Leu Gln Ser Leu Thr Asn Leu
                565                 570                 575

Leu Ser Ser Asn Leu Ser Trp Leu Ser Leu Asp Val Ser Ala Ala Phe
            580                 585                 590

Tyr His Leu Pro Leu His Pro Ala Ala Met Pro His Leu Leu Val Gly
        595                 600                 605

Ser Ser Gly Leu Ser Arg Tyr Val Ala Arg Leu Ser Ser Asn Ser Arg
    610                 615                 620

Ile Phe Asn Tyr Gln His Gly Thr Met Gln Asn Leu His Asp Ser Cys
625                 630                 635                 640

Ser Arg Asn Leu Tyr Val Ser Leu Leu Leu Leu Tyr Gln Thr Phe Gly
                645                 650                 655

Arg Lys Leu His Leu Tyr Ser His Pro Ile Ile Leu Gly Phe Arg Lys
            660                 665                 670
```

```
Ile Pro Met Gly Val Gly Leu Ser Pro Phe Leu Leu Ala Gln Phe Thr
        675                 680                 685

Ser Ala Ile Cys Ser Val Val Arg Arg Ala Phe Pro His Cys Leu Ala
    690                 695                 700

Phe Ser Gly Ala Lys Ser Val Gln His Leu Glu Ser Leu Phe Thr Ala
705                 710                 715                 720

Val Thr Asn Phe Leu Leu Ser Leu Gly Ile His Leu Asn Pro Asn Lys
                725                 730                 735

Thr Lys Arg Trp Gly Tyr Ser Leu His Phe Met Gly Tyr Val Ile Gly
            740                 745                 750

Cys Tyr Gly Ser Leu Pro Gln Asp His Ile Ile Gln Lys Ile Lys Glu
        755                 760                 765

Cys Phe Arg Lys Leu Pro Val Asn Arg Pro Ile Asp Trp Lys Val Cys
    770                 775                 780

Gln Arg Ile Val Gly Leu Leu Gly Phe Ala Ala Pro Phe Thr Gln Cys
785                 790                 795                 800

Gly Tyr Pro Ala Leu Met Pro Leu Tyr Ala Cys Ile Gln Ser Lys Gln
                805                 810                 815

Ala Phe Thr Phe Ser Pro Thr Tyr Lys Ala Phe Leu Cys Lys Gln Tyr
            820                 825                 830

Leu Asn Leu Tyr Pro Val Ala Arg Gln Arg Pro Gly Leu Cys Gln Val
        835                 840                 845

Phe Ala His Ala Thr Pro Thr Gly Trp Gly Leu Val Met Gly His Gln
    850                 855                 860

Arg Met Arg Gly Thr Phe Leu Ser Arg Lys Tyr Thr Ser Phe Pro Trp
865                 870                 875                 880

Leu Leu Gly Cys Ala Ala Asn Trp Ile Leu Arg Gly Thr Ser Phe Val
                885                 890                 895

Tyr Tyr Pro Ser Ala Leu Asn Pro Tyr His Asp Pro Ser Arg Gly Arg
            900                 905                 910

Leu Gly Leu Ser Arg Pro Leu Leu Arg Leu Pro Phe Arg Pro Thr Thr
        915                 920                 925

Gly Arg Thr Ser Leu Tyr Ala Asp Ser Pro Ser Val Pro Ser His Leu
    930                 935                 940

Pro Asp Arg Val His Phe Ala Ser Pro Leu His Val Ala Trp Arg Pro
945                 950                 955                 960

Pro Tyr Val Leu Leu Ser Ala Gly Ala Leu Thr Ala Leu Met Leu Ile
                965                 970                 975

Ile Phe Leu Met Thr Cys Cys Arg Arg Val Asn Arg Ser Glu Pro Thr
            980                 985                 990

Gln His Asn Leu Arg Gly Thr Gly  Arg Glu Val Ser Val  Thr Pro Gln
        995                 1000                1005

Ser Gly  Lys Ile Ile Ser Ser  Trp Glu Ser His Lys  Ser Gly Gly
    1010                1015                1020

Glu Thr  Arg Leu
    1025
```

<210> SEQ ID NO 12
<211> LENGTH: 1095
<212> TYPE: PRT
<213> ORGANISM: artificial sequence
<220> FEATURE:
<223> OTHER INFORMATION: fusion between signal sequence -core (1'148)-
mutated Y07587 polymerase -env1-env2 and TM sequence

<400> SEQUENCE: 12

-continued

```
Met Val Pro Gln Ala Leu Leu Phe Val Pro Leu Leu Val Phe Pro Leu
1               5                   10                  15

Cys Phe Gly Lys Phe Pro Ile Asp Ile Asp Pro Tyr Lys Glu Phe Gly
            20                  25                  30

Ala Thr Val Glu Leu Leu Ser Phe Leu Pro Ser Asp Phe Phe Pro Ser
        35                  40                  45

Val Arg Asp Leu Leu Asp Thr Ala Ser Ala Leu Tyr Arg Glu Ala Leu
    50                  55                  60

Glu Ser Pro Glu His Cys Ser Pro His His Thr Ala Leu Arg Gln Ala
65                  70                  75                  80

Ile Leu Cys Trp Gly Glu Leu Met Thr Leu Ala Thr Trp Val Gly Gly
                85                  90                  95

Asn Leu Glu Asp Pro Ile Ser Arg Asp Leu Val Val Ser Tyr Val Asn
            100                 105                 110

Thr Asn Met Gly Leu Lys Phe Arg Gln Leu Leu Trp Phe His Ile Ser
        115                 120                 125

Cys Leu Thr Phe Gly Arg Glu Thr Val Ile Glu Tyr Leu Val Ser Phe
    130                 135                 140

Gly Val Trp Ile Arg Thr Pro Pro Ala Tyr Arg Pro Pro Asn Ala Pro
145                 150                 155                 160

Ile Leu Ser Thr Leu Pro Glu Thr Thr Val Pro Leu Ser Tyr Gln His
                165                 170                 175

Phe Arg Arg Leu Leu Leu Leu Asp Asp Glu Ala Gly Pro Leu Glu Glu
            180                 185                 190

Glu Leu Pro Arg Leu Ala Asp Glu Gly Leu Asn Arg Arg Val Ala Glu
        195                 200                 205

Asp Leu Asn Leu Gly Asn Leu Asn Val Ser Ile Pro Trp Thr His Lys
    210                 215                 220

Val Gly Asn Phe Thr Gly Leu Tyr Ser Ser Thr Val Pro Val Phe Asn
225                 230                 235                 240

Pro His Trp Lys Thr Pro Ser Phe Pro Asn Ile His Leu His Gln Asp
                245                 250                 255

Ile Ile Lys Lys Cys Glu Gln Phe Val Gly Pro Leu Thr Val Asn Glu
            260                 265                 270

Lys Arg Arg Leu Gln Leu Ile Met Pro Ala Arg Phe Tyr Pro Asn Val
        275                 280                 285

Thr Lys Tyr Leu Pro Leu Asp Lys Gly Ile Lys Pro Tyr Tyr Pro Glu
    290                 295                 300

His Leu Val Asn His Tyr Phe Gln Thr Arg His Tyr Leu His Thr Leu
305                 310                 315                 320

Trp Lys Ala Gly Ile Leu Tyr Lys Arg Glu Thr Thr His Ser Ala Ser
                325                 330                 335

Phe Cys Gly Ser Pro Tyr Ser Trp Glu Gln Lys Leu Gln His Gly Ala
            340                 345                 350

Glu Ser Phe His Gln Gln Ser Ser Gly Ile Leu Ser Arg Pro Pro Val
        355                 360                 365

Gly Ser Ser Leu Gln Ser Lys His Arg Lys Ser Arg Leu Gly Leu Gln
    370                 375                 380

Ser Gln Gln Gly His Leu Ala Arg Arg Gln Gln Gly Arg Ser Trp Ser
385                 390                 395                 400

Ile Arg Ala Gly Ile His Pro Thr Ala Arg Arg Ser Phe Gly Val Glu
                405                 410                 415
```

-continued

```
Pro Ser Gly Ser Gly His Ser Thr Asn Leu Ala Ser Lys Ser Ala Ser
            420                 425                 430

Cys Leu Tyr Gln Ser Pro Val Arg Lys Ala Ala Tyr Pro Ala Val Ser
        435                 440                 445

Thr Phe Glu Lys His Ser Ser Ser Gly His Ala Val Glu Leu His Asn
    450                 455                 460

Leu Pro Pro Asn Ser Ala Arg Ser Gln Ser Glu Arg Pro Val Phe Pro
465                 470                 475                 480

Cys Trp Trp Leu Gln Phe Arg Asn Ser Lys Pro Cys Ser Asp Tyr Cys
                485                 490                 495

Leu Ser His Ile Val Asn Leu Leu Glu Asp Trp Gly Pro Cys Ala Glu
            500                 505                 510

His Gly Glu His His Ile Arg Ile Pro Arg Thr Pro Ala Arg Val Thr
        515                 520                 525

Gly Gly Val Phe Leu Val Asp Lys Asn Pro His Asn Thr Ala Glu Ser
    530                 535                 540

Arg Leu Val Val Asp Phe Ser Gln Phe Ser Arg Gly Asn Tyr Arg Val
545                 550                 555                 560

Ser Trp Pro Lys Phe Ala Val Pro Asn Leu Gln Ser Leu Thr Asn Leu
                565                 570                 575

Leu Ser Ser Asn Leu Ser Trp Leu Ser Leu Asp Val Ser Ala Ala Phe
            580                 585                 590

Tyr His Leu Pro Leu His Pro Ala Ala Met Pro His Leu Leu Val Gly
        595                 600                 605

Ser Ser Gly Leu Ser Arg Tyr Val Ala Arg Leu Ser Ser Asn Ser Arg
    610                 615                 620

Ile Phe Asn Tyr Gln His Gly Thr Met Gln Asn Leu His Asp Ser Cys
625                 630                 635                 640

Ser Arg Asn Leu Tyr Val Ser Leu Leu Leu Leu Tyr Gln Thr Phe Gly
                645                 650                 655

Arg Lys Leu His Leu Tyr Ser His Pro Ile Ile Leu Gly Phe Arg Lys
            660                 665                 670

Ile Pro Met Gly Val Gly Leu Ser Pro Phe Leu Leu Ala Gln Phe Thr
        675                 680                 685

Ser Ala Ile Cys Ser Val Val Arg Arg Ala Phe Pro His Cys Leu Ala
    690                 695                 700

Phe Ser Val Leu Gln Ala Gly Phe Phe Leu Leu Thr Arg Ile Leu Thr
705                 710                 715                 720

Ile Pro Gln Ser Leu Asp Ser Trp Trp Thr Ser Leu Asn Phe Leu Gly
                725                 730                 735

Gly Thr Thr Val Cys Leu Gly Gln Gly Ala Lys Ser Val Gln His Leu
            740                 745                 750

Glu Ser Leu Phe Thr Ala Val Thr Asn Phe Leu Leu Ser Leu Gly Ile
        755                 760                 765

His Leu Asn Pro Asn Lys Thr Lys Arg Trp Gly Tyr Ser Leu His Phe
    770                 775                 780

Met Gly Tyr Val Ile Gly Cys Tyr Gly Ser Leu Pro Gln Asp His Ile
785                 790                 795                 800

Ile Gln Lys Ile Lys Glu Cys Phe Arg Lys Leu Pro Val Asn Arg Pro
                805                 810                 815

Ile Asp Trp Lys Val Cys Gln Arg Ile Val Gly Leu Leu Gly Phe Ala
            820                 825                 830

Ala Pro Phe Thr Gln Cys Gly Tyr Pro Ala Leu Met Pro Leu Tyr Ala
```

```
        835                 840                 845

Cys Ile Gln Ser Lys Gln Ala Phe Thr Phe Ser Pro Thr Tyr Lys Ala
    850                 855                 860

Phe Leu Cys Lys Gln Tyr Leu Asn Leu Tyr Pro Val Ala Arg Gln Arg
865                 870                 875                 880

Pro Gly Leu Cys Gln Val Phe Ala His Ala Thr Pro Thr Gly Trp Gly
                885                 890                 895

Leu Val Met Gly His Gln Arg Met Arg Gly Thr Phe Leu Trp Ala Ser
            900                 905                 910

Ala Arg Phe Ser Trp Leu Ser Leu Leu Val Pro Phe Val Gln Trp Phe
        915                 920                 925

Val Gly Leu Ser Pro Thr Val Trp Leu Ser Val Ser Arg Lys Tyr Thr
    930                 935                 940

Ser Phe Pro Trp Leu Leu Gly Cys Ala Ala Asn Trp Ile Leu Arg Gly
945                 950                 955                 960

Thr Ser Phe Val Tyr Tyr Pro Ser Ala Leu Asn Pro Tyr His Asp Pro
                965                 970                 975

Ser Arg Gly Arg Leu Gly Leu Ser Arg Pro Leu Leu Arg Leu Pro Phe
            980                 985                 990

Arg Pro Thr Thr Gly Arg Thr Ser  Leu Tyr Ala Asp Ser  Pro Ser Val
        995                 1000                1005

Pro Ser  His Leu Pro Asp Arg  Val His Phe Ala Ser  Pro Leu His
    1010                1015                1020

Val Ala  Trp Arg Pro Pro Tyr  Val Leu Leu Ser Ala  Gly Ala Leu
    1025                1030                1035

Thr Ala  Leu Met Leu Ile Ile  Phe Leu Met Thr Cys  Cys Arg Arg
    1040                1045                1050

Val Asn  Arg Ser Glu Pro Thr  Gln His Asn Leu Arg  Gly Thr Gly
    1055                1060                1065

Arg Glu  Val Ser Val Thr Pro  Gln Ser Gly Lys Ile  Ile Ser Ser
    1070                1075                1080

Trp Glu  Ser His Lys Ser Gly  Gly Glu Thr Arg Leu
    1085                1090                1095


<210> SEQ ID NO 13
<211> LENGTH: 2379
<212> TYPE: DNA
<213> ORGANISM: artificial sequence
<220> FEATURE:
<223> OTHER INFORMATION: nucleotide sequence encoding the mutated Y07587
      polymerase

<400> SEQUENCE: 13

atgccactga gctaccagca ctttcgcagg ctgttactgc tggatgatga agctggaccg      60

ctggaggagg agctgccacg tctggctgat gagggactga accgtcgtgt ggctgaggac     120

ctgaacctgg gcaacctgaa cgtgagcatt ccttggactc ataaggtggg aaactttacg     180

ggactttatt cttctactgt acctgtcttt aaccctcatt ggaaaacacc ctcttttcct     240

aatatacatt tacaccaaga cattatcaag aaatgtgaac aatttgtagg accactcaca     300

gtcaatgaga aaagaagact gcaattgatt atgcctgcta ggttttatcc aaatgttacc     360

aaatatttgc cattggataa gggtattaaa ccttattatc cagaacatct agttaatcat     420

tacttccaaa ccagacatta tttacacact ctatggaagg caggtatatt atataagaga     480

gaaacaacac atagtgcctc attttgtggg tcaccatatt cttgggaaca aaagctacag     540
```

```
catggagcag aatctttcca ccagcaatcc tctgggattc tttcccgacc accagttgga    600

tccagccttc agagcaaaca ccgcaaatcc agattgggac ttcaatccca acaaggacac    660

ctggccagac gccaacaagg taggagctgg agcattcgag ctgggattca ccccaccgca    720

cggaggtctt ttggggtgga gccctcaggc tcagggcatt ctacaaacct tgccagcaaa    780

tcagcctcct gcctctacca atcgccagtc aggaaggcag cctaccctgc tgtctccacc    840

tttgagaaac actcatcctc aggccatgca gtggaactcc acaaccttcc accaaactct    900

gcaagatccc agagtgagag gcctgtattt ccctgctggt ggctccagtt caggaacagt    960

aaaccctgtt ccgactactg tctctcccat atcgtcaatc ttctcgagga ttggggaccc   1020

tgcgctgaac acggtgagca ccatattcgc atcccgagaa cgccagcacg cgtgaccggt   1080

ggcgtgttcc tggtggataa gaacccacat aacacggctg aaagccgtct ggttgttgac   1140

tttagccagt tcagccgtgg caattatcgc gttagctggc ctaagtttgc ggtgccgaat   1200

ctgcagagcc tgacgaatct gttaagcagc aatttaagct ggctgagctt agacgttagc   1260

gcagccttct accacctgcc actgcaccca gcagcgatgc cacacctgct ggtgggcagc   1320

agcggtctga gccgttacgt ggcacgcctg agcagcaaca gccgtatatt taattatcaa   1380

catggcacga tgcaaaattt acatgatagc tgtagccgta atctgtacgt gagcctgtta   1440

ctgttatatc agacgtttgg tcgcaagctg catttataca gccacccgat tattttaggg   1500

ttccgcaaga tcccgatggg tgttggtctg tctccattcc tgttagcgca attcaccagc   1560

gcaatctgca gcgttgtgcg cagagcgttt ccgcattgcc tggcgtttag cggtgcgaaa   1620

agcgtgcaac acctggaaag cctgttcacg gcagtgacga acttcctgct gagcctgggc   1680

attcacctga accctaacaa aacaaagaga tggggttact ctttacattt catgggctat   1740

gtcattggat gttatgggtc attgccacaa gatcacatca tacaaaagat caaagaatgt   1800

tttcgaaaac ttcctgttaa cagacctatt gattggaaag tctgtcaacg tattgtgggt   1860

cttttgggtt ttgctgctcc ttttacacaa tgtggttatc ctgctttaat gcctttgtat   1920

gcatgtattc agtcgaagca ggcttttact ttctcgccaa cttacaaggc ctttctgtgt   1980

aaacaatacc tgaaccttta ccctgttgct cggcaaagac caggtctgtg ccaagtgttt   2040

gctcacgcaa cccctactgg ctggggattg gtcatgggac atcagcgcat gcgtggaacc   2100

tttctgtcca gaaaatatac atcgtttcca tggctgctag gctgtgctgc caactggata   2160

ctgagaggca ccagcttcgt gtattatccc agcgctctca acccttacca tgatccttct   2220

cgaggtagac tgggcctgag cagacctctg ctgagactcc ccttccgacc cacaaccgga   2280

agaacaagcc tgtatgccga tagccctagc gtccccagcc acctccctga tagagtccat   2340

tttgccagcc cactccatgt ggcctggagg cctccctaa                          2379
```

<210> SEQ ID NO 14
<211> LENGTH: 2820
<212> TYPE: DNA
<213> ORGANISM: artificial sequence
<220> FEATURE:
<223> OTHER INFORMATION: nucleotide sequence encoding the fusion between truncated core (1-148) and mutated Y07587 polymerase

<400> SEQUENCE: 14

```
atggatatcg atccctacaa ggagttcggt gccaccgtcg aactgctgag cttcctgccc     60

agcgatttct tcccaagcgt acgtgacctt ctagatacag cctcagctct gtatcgggaa    120

gccttagagt ctcctgagca ttgttcacct caccatactg ctctcaggca agcaattctg    180
```

-continued

```
tgctggggag aactaatgac tctagctacc tgggtgggtg gtaatttgga agatccaata    240
tccagggacc tagtagtcag ttatgtcaac actaatatgg gactaaagtt ccgacaacta    300
ttgtggtttc acatttcttg tctcactttt ggaagagaaa cagttataga atatttggtg    360
tctttcggag tgtggattcg cactcctcca gcttatagac caccaaacgc accgatactg    420
agcaccctgc cagaaaccac cgtgccactg agctaccagc actttcgcag gctgttactg    480
ctggatgatg aagctggacc gctggaggag gagctgccac gtctggctga tgagggactg    540
aaccgtcgtg tggctgagga cctgaacctg ggcaacctga acgtgagcat tccttggact    600
cataaggtgg gaaactttac gggactttat tcttctactg tacctgtctt taaccctcat    660
tggaaaacac cctcttttcc taatatacat ttacaccaag acattatcaa gaaatgtgaa    720
caatttgtag gaccactcac agtcaatgag aaaagaagac tgcaattgat tatgcctgct    780
aggttttatc caaatgttac caaatatttg ccattggata agggtattaa accttattat    840
ccagaacatc tagttaatca ttacttccaa accagacatt atttacacac tctatggaag    900
gcaggtatat tatataagag agaaacaaca catagtgcct cattttgtgg gtcaccatat    960
tcttgggaac aaaagctaca gcatggagca gaatctttcc accagcaatc ctctgggatt   1020
ctttcccgac caccagttgg atccagcctt cagagcaaac accgcaaatc cagattggga   1080
cttcaatccc aacaaggaca cctggccaga cgccaacaag gtaggagctg gagcattcga   1140
gctgggattc accccaccgc acggaggtct tttggggtgg agccctcagg ctcagggcat   1200
tctacaaacc ttgccagcaa atcagcctcc tgcctctacc aatcgccagt caggaaggca   1260
gcctaccctg ctgtctccac ctttgagaaa cactcatcct caggccatgc agtggaactc   1320
cacaaccttc caccaaactc tgcaagatcc cagagtgaga ggcctgtatt tccctgctgg   1380
tggctccagt tcaggaacag taaaccctgt tccgactact gtctctccca tatcgtcaat   1440
cttctcgagg attggggacc ctgcgctgaa cacggtgagc accatattcg catcccgaga   1500
acgccagcac gcgtgaccgg tggcgtgttc ctggtggata agaacccaca taacacggct   1560
gaaagccgtc tggttgttga ctttagccag ttcagccgtg gcaattatcg cgttagctgg   1620
cctaagtttg cggtgccgaa tctgcagagc ctgacgaatc tgttaagcag caatttaagc   1680
tggctgagct tagacgttag cgcagccttc taccacctgc cactgcaccc agcagcgatg   1740
ccacacctgc tggtgggcag cagcggtctg agccgttacg tggcacgcct gagcagcaac   1800
agccgtatat ttaattatca acatggcacg atgcaaaatt tacatgatag ctgtagccgt   1860
aatctgtacg tgagcctgtt actgttatat cagacgtttg gtcgcaagct gcatttatac   1920
agccacccga ttattttagg gttccgcaag atcccgatgg gtgttggtct gtctccattc   1980
ctgttagcgc aattcaccag cgcaatctgc agcgttgtgc gcagagcgtt tccgcattgc   2040
ctggcgttta gcggtgcgaa aagcgtgcaa cacctggaaa gcctgttcac ggcagtgacg   2100
aacttcctgc tgagcctggg cattcacctg aaccctaaca aaacaaagag atggggttac   2160
tctttacatt tcatgggcta tgtcattgga tgttatgggt cattgccaca agatcacatc   2220
atacaaaaga tcaaagaatg ttttcgaaaa cttcctgtta acagacctat tgattggaaa   2280
gtctgtcaac gtattgtggg tcttttgggt tttgctgctc cttttacaca atgtggttat   2340
cctgctttaa tgcctttgta tgcatgtatt cagtcgaagc aggcttttac tttctcgcca   2400
acttacaagg cctttctgtg taaacaatac ctgaaccttt accctgttgc tcggcaaaga   2460
ccaggtctgt gccaagtgtt tgctcacgca acccctactg gctggggatt ggtcatggga   2520
catcagcgca tgcgtggaac ctttctgtcc agaaaatata catcgtttcc atggctgcta   2580
```

ggctgtgctg ccaactggat actgagaggc accagcttcg tgtattatcc cagcgctctc 2640
aacccttacc atgatccttc tcgaggtaga ctgggcctga gcagacctct gctgagactc 2700
cccttccgac ccacaaccgg aagaacaagc ctgtatgccg atagccctag cgtccccagc 2760
cacctccctg atagagtcca ttttgccagc ccactccatg tggcctggag gcctccctaa 2820

<210> SEQ ID NO 15
<211> LENGTH: 3024
<212> TYPE: DNA
<213> ORGANISM: artificial sequence
<220> FEATURE:
<223> OTHER INFORMATION: nucleotide sequence encoding the fusion between truncated core (1-148)-mutated Y07587 polymerase-env1 and env2

<400> SEQUENCE: 15
atggatatcg atccctacaa ggagttcggt gccaccgtcg aactgctgag cttcctgccc 60
agcgatttct tcccaagcgt acgtgacctt ctagatacag cctcagctct gtatcgggaa 120
gccttagagt ctcctgagca ttgttcacct caccatactg ctctcaggca agcaattctg 180
tgctggggag aactaatgac tctagctacc tgggtgggtg gtaatttgga agatccaata 240
tccagggacc tagtagtcag ttatgtcaac actaatatgg gactaaagtt ccgacaacta 300
ttgtggtttc acatttcttg tctcactttt ggaagagaaa cagttataga atatttggtg 360
tctttcggag tgtggattcg cactcctcca gcttatagac caccaaacgc accgatactg 420
agcaccctgc cagaaaccac cgtgccactg agctaccagc actttcgcag gctgttactg 480
ctggatgatg aagctggacc gctggaggag gagctgccac gtctggctga tgagggactg 540
aaccgtcgtg tggctgagga cctgaacctg ggcaacctga acgtgagcat tccttggact 600
cataaggtgg gaaactttac gggactttat tcttctactg tacctgtctt taaccctcat 660
tggaaaacac cctcttttcc taatatacat ttacaccaag acattatcaa gaaatgtgaa 720
caatttgtag gaccactcac agtcaatgag aaaagaagac tgcaattgat tatgcctgct 780
aggttttatc caaatgttac caaatatttg ccattggata agggtattaa accttattat 840
ccagaacatc tagttaatca ttacttccaa accagacatt atttacacac tctatggaag 900
gcaggtatat tatataagag agaaacaaca catagtgcct cattttgtgg gtcaccatat 960
tcttgggaac aaaagctaca gcatggagca gaatctttcc accagcaatc ctctgggatt 1020
ctttcccgac caccagttgg atccagcctt cagagcaaac accgcaaatc cagattggga 1080
cttcaatccc aacaaggaca cctggccaga cgccaacaag gtaggagctg gagcattcga 1140
gctgggattc accccaccgc acggaggtct tttggggtgg agccctcagg ctcagggcat 1200
tctacaaacc ttgccagcaa atcagcctcc tgcctctacc aatcgccagt caggaaggca 1260
gcctaccctg ctgtctccac ctttgagaaa cactcatcct caggccatgc agtggaactc 1320
cacaaccttc caccaaactc tgcaagatcc cagagtgaga ggcctgtatt tccctgctgg 1380
tggctccagt tcaggaacag taaaccctgt tccgactact gtctctccca tatcgtcaat 1440
cttctcgagg attggggacc ctgcgctgaa cacggtgagc accatattcg catcccgaga 1500
acgccagcac gcgtgaccgg tggcgtgttc ctggtggata agaacccaca taacacggct 1560
gaaagccgtc tggttgttga ctttagccag ttcagccgtg gcaattatcg cgttagctgg 1620
cctaagtttg cggtgccgaa tctgcagagc ctgacgaatc tgttaagcag caatttaagc 1680
tggctgagct tagacgttag cgcagccttc taccacctgc cactgcaccc agcagcgatg 1740
ccacacctgc tggtgggcag cagcggtctg agccgttacg tggcacgcct gagcagcaac 1800
agccgtatat ttaattatca acatggcacg atgcaaaatt tacatgatag ctgtagccgt 1860
aatctgtacg tgagcctgtt actgttatat cagacgtttg gtcgcaagct gcatttatac 1920
agccacccga ttattttagg gttccgcaag atcccgatgg gtgttggtct gtctccattc 1980
ctgttagcgc aattcaccag cgcaatctgc agcgttgtgc gcagagcgtt tccgcattgc 2040
ctggcgttta gcgtcctgca agcaggcttc ttcctgctga cccgtattct gaccattcca 2100
caaagcctgg atagctggtg gaccagcctg aacttcctgg gtggcaccac ggtttgcctg 2160
ggtcagggtg cgaaaagcgt gcaacacctg gaaagcctgt tcacggcagt gacgaacttc 2220
ctgctgagcc tgggcattca cctgaaccct aacaaaacaa agagatgggg ttactcttta 2280
catttcatgg gctatgtcat tggatgttat gggtcattgc cacaagatca catcatacaa 2340
aagatcaaag aatgttttcg aaaacttcct gttaacagac ctattgattg gaaagtctgt 2400
caacgtattg tgggtctttt gggttttgct gctcctttta cacaatgtgg ttatcctgct 2460
ttaatgcctt tgtatgcatg tattcagtcg aagcaggctt ttactttctc gccaacttac 2520
aaggcctttc tgtgtaaaca atacctgaac ctttaccctg ttgctcggca aagaccaggt 2580
ctgtgccaag tgtttgctca cgcaacccct actggctggg gattggtcat gggacatcag 2640
cgcatgcgtg gaacctttct gtgggcaagc gcacgcttta gctggctgag cctgctggtt 2700
ccgttcgtgc aatggtttgt gggtctgagc ccaaccgtgt ggctgagcgt gtccagaaaa 2760
tatacatcgt ttccatggct gctaggctgt gctgccaact ggatactgag aggcaccagc 2820
ttcgtgtatt atcccagcgc tctcaaccct taccatgatc cttctcgagg tagactgggc 2880
ctgagcagac ctctgctgag actccccttc cgacccacaa ccggaagaac aagcctgtat 2940
gccgatagcc ctagcgtccc cagccacctc cctgatagag tccattttgc cagcccactc 3000
catgtggcct ggaggcctcc ctaa 3024

<210> SEQ ID NO 16
<211> LENGTH: 3723
<212> TYPE: DNA
<213> ORGANISM: artificial sequence
<220> FEATURE:
<223> OTHER INFORMATION: nucleotide sequence encoding core (1-183) IRES and fusion between mutated Y07587 polymerase-env1-env2

<400> SEQUENCE: 16
atggatatcg atccctacaa ggagttcggt gccaccgtcg aactgctgag cttcctgccc 60
agcgatttct tcccaagcgt acgtgacctt ctagatacag cctcagctct gtatcgggaa 120
gccttagagt ctcctgagca ttgttcacct caccatactg ctctcaggca agcaattctg 180
tgctggggag aactaatgac tctagctacc tgggtgggtg gtaatttgga agatccaata 240
tccagggacc tagtagtcag ttatgtcaac actaatatgg gactaaagtt ccgacaacta 300
ttgtggtttc acatttcttg tctcactttt ggaagagaaa cagttataga atatttggtg 360
tctttcggag tgtggattcg cactcctcca gcttatagac caccaaacgc accgatactg 420
agcaccctgc cagaaaccac cgtggtgcgt cgtcgtggtc gcagcccacg caggcgtacc 480
ccaagcccac gtcgtcgcag aagccagagc ccacgacgtc gcaggagcca gagccgtgag 540
agccagtgct aaaagcttga tatcgaattc acgcgtcccc cccctaacgt tactggccga 600
agccgcttgg aataaggccg gtgtgcgttt gtctatatgt tattttccac catattgccg 660 tctttttggca atgtgagggc ccggaaacct ggccctgtct tcttgacgag cattcctagg 720
ggtctttccc ctctcgccaa aggaatgcaa ggtctgttga atgtcgtgaa ggaagcagtt 780

-continued

```
cctctggaag cttcttgaag acaaacaacg tctgtagcga ccctttgcag gcagcggaac    840
cccccacctg gcgacaggtg cctctgcggc caaaagccac gtgtataaga tacacctgca    900
aaggcggcac aaccccagtg ccacgttgtg agttggatag ttgtggaaag agtcaaatgg    960
ctctcctcaa gcgtattcaa caaggggctg aaggatgccc agaaggtacc ccattgtatg   1020
ggatctgatc tggggcctcg gtgcacatgc tttacatgtg tttagtcgag gttaaaaaac   1080
gtctaggccc cccgaaccac ggggacgtgg ttttcctttg aaaaacacga tgataatacc   1140
atgccactga gctaccagca ctttcgcagg ctgttactgc tggatgatga agctggaccg   1200
ctggaggagg agctgccacg tctggctgat gagggactga accgtcgtgt ggctgaggac   1260
ctgaacctgg gcaacctgaa cgtgagcatt ccttggactc ataaggtggg aaactttacg   1320
ggactttatt cttctactgt acctgtcttt aaccctcatt ggaaaaacacc ctcttttcct   1380
aatatacatt tacaccaaga cattatcaag aaatgtgaac aatttgtagg accactcaca   1440
gtcaatgaga aaagaagact gcaattgatt atgcctgcta ggttttatcc aaatgttacc   1500
aaatatttgc cattggataa gggtattaaa ccttattatc cagaacatct agttaatcat   1560
tacttccaaa ccagacatta tttacacact ctatggaagg caggtatatt atataagaga   1620
gaaacaacac atagtgcctc attttgtggg tcaccatatt cttgggaaca aaagctacag   1680
catggagcag aatctttcca ccagcaatcc tctgggattc tttcccgacc accagttgga   1740
tccagccttc agagcaaaca ccgcaaatcc agattgggac ttcaatccca acaaggacac   1800
ctggccagac gccaacaagg taggagctgg agcattcgag ctgggattca ccccaccgca   1860
cggaggtctt ttggggtgga gccctcaggc tcagggcatt ctacaaacct tgccagcaaa   1920
tcagcctcct gcctctacca atcgccagtc aggaaggcag cctaccctgc tgtctccacc   1980
tttgagaaac actcatcctc aggccatgca gtggaactcc acaaccttcc accaaactct   2040
gcaagatccc agagtgagag gcctgtattt ccctgctggt ggctccagtt caggaacagt   2100
aaaccctgtt ccgactactg tctctcccat atcgtcaatc ttctcgagga ttggggaccc   2160
tgcgctgaac acggtgagca ccatattcgc atcccgagaa cgccagcacg cgtgaccggt   2220
ggcgtgttcc tggtggataa gaacccacat aacacggctg aaagccgtct ggttgttgac   2280
tttagccagt tcagccgtgg caattatcgc gttagctggc ctaagtttgc ggtgccgaat   2340
ctgcagagcc tgacgaatct gttaagcagc aatttaagct ggctgagctt agacgttagc   2400
gcagccttct accacctgcc actgcaccca gcagcgatgc cacacctgct ggtgggcagc   2460
agcggtctga gccgttacgt ggcacgcctg agcagcaaca gccgtatatt taattatcaa   2520
catggcacga tgcaaaattt acatgatagc tgtagccgta atctgtacgt gagcctgtta   2580
ctgttatatc agacgtttgg tcgcaagctg catttataca gccacccgat tattttaggg   2640
ttccgcaaga tcccgatggg tgttggtctg tctccattcc tgttagcgca attcaccagc   2700
gcaatctgca gcgttgtgcg cagagcgttt ccgcattgcc tggcgtttag cgtcctgcaa   2760
gcaggcttct tcctgctgac ccgtattctg accattccac aaagcctgga tagctggtgg   2820
accagcctga acttcctggg tggcaccacg gtttgcctgg gtcagggtgc gaaaagcgtg   2880
caacacctgg aaagcctgtt cacggcagtg acgaacttcc tgctgagcct gggcattcac   2940
ctgaacccta acaaaacaaa gagatggggt tactctttac atttcatggg ctatgtcatt   3000
ggatgttatg ggtcattgcc acaagatcac atcatacaaa agatcaaaga atgttttcga   3060
aaacttcctg ttaacagacc tattgattgg aaagtctgtc aacgtattgt gggtcttttg   3120
```

-continued

```
ggttttgctg ctccttttac acaatgtggt tatcctgctt taatgccttt gtatgcatgt   3180

attcagtcga agcaggcttt tactttctcg ccaacttaca aggcctttct gtgtaaacaa   3240

tacctgaacc tttaccctgt tgctcggcaa agaccaggtc tgtgccaagt gtttgctcac   3300

gcaaccccta ctggctgggg attggtcatg ggacatcagc gcatgcgtgg aacctttctg   3360

tgggcaagcg cacgctttag ctggctgagc ctgctggttc cgttcgtgca atggtttgtg   3420

ggtctgagcc caaccgtgtg gctgagcgtg tccagaaaat atacatcgtt tccatggctg   3480

ctaggctgtg ctgccaactg gatactgaga ggcaccagct tcgtgtatta tcccagcgct   3540

ctcaaccctt accatgatcc ttctcgaggt agactgggcc tgagcagacc tctgctgaga   3600

ctccccttcc gacccacaac cggaagaaca agcctgtatg ccgatagccc tagcgtcccc   3660

agccacctcc ctgatagagt ccattttgcc agcccactcc atgtggcctg gaggcctccc   3720

taa                                                                 3723
```

<210> SEQ ID NO 17
<211> LENGTH: 3723
<212> TYPE: DNA
<213> ORGANISM: artificial sequence
<220> FEATURE:
<223> OTHER INFORMATION: nucleotide sequence encoding fusion mutated Y07587 polymerase-env1-env2 IRES core (1-183)

<400> SEQUENCE: 17

```
atgccactga gctaccagca ctttcgcagg ctgttactgc tggatgatga agctggaccg     60

ctggaggagg agctgccacg tctggctgat gagggactga accgtcgtgt ggctgaggac    120

ctgaacctgg gcaacctgaa cgtgagcatt ccttggactc ataaggtggg aaactttacg    180

ggactttatt cttctactgt acctgtcttt aaccctcatt ggaaaacacc ctcttttcct    240

aatatacatt tacaccaaga cattatcaag aaatgtgaac aatttgtagg accactcaca    300

gtcaatgaga aaagaagact gcaattgatt atgcctgcta ggttttatcc aaatgttacc    360

aaatatttgc cattggataa gggtattaaa ccttattatc cagaacatct agttaatcat    420

tacttccaaa ccagacatta tttacacact ctatggaagg caggtatatt atataagaga    480

gaaacaacac atagtgcctc attttgtggg tcaccatatt cttgggaaca aaagctacag    540

catggagcag aatctttcca ccagcaatcc tctgggattc tttcccgacc accagttgga    600

tccagccttc agagcaaaca ccgcaaatcc agattgggac ttcaatccca acaaggacac    660

ctggccagac gccaacaagg taggagctgg agcattcgag ctgggattca ccccaccgca    720

cggaggtctt ttggggtgga gccctcaggc tcagggcatt ctacaaacct tgccagcaaa    780

tcagcctcct gcctctacca atcgccagtc aggaaggcag cctaccctgc tgtctccacc    840

tttgagaaac actcatcctc aggccatgca gtggaactcc acaaccttcc accaaactct    900

gcaagatccc agagtgagag gcctgtattt ccctgctggt ggctccagtt caggaacagt    960

aaaccctgtt ccgactactg tctctcccat atcgtcaatc ttctcgagga ttggggaccc   1020

tgcgctgaac acggtgagca ccatattcgc atcccgagaa cgccagcacg cgtgaccggt   1080

ggcgtgttcc tggtggataa gaacccacat aacacggctg aaagccgtct ggttgttgac   1140

tttagccagt tcagccgtgg caattatcgc gttagctggc ctaagtttgc ggtgccgaat   1200

ctgcagagcc tgacgaatct gttaagcagc aatttaagct ggctgagctt agacgttagc   1260

gcagccttct accacctgcc actgcaccca gcagcgatgc cacacctgct ggtgggcagc   1320

agcggtctga gccgttacgt ggcacgcctg agcagcaaca gccgtatatt taattatcaa   1380
```

-continued

```
catggcacga tgcaaaattt acatgatagc tgtagccgta atctgtacgt gagcctgtta   1440
ctgttatatc agacgtttgg tcgcaagctg catttataca gccacccgat tattttaggg   1500
ttccgcaaga tcccgatggg tgttggtctg tctccattcc tgttagcgca attcaccagc   1560
gcaatctgca gcgttgtgcg cagagcgttt ccgcattgcc tggcgtttag cgtcctgcaa   1620
gcaggcttct tcctgctgac ccgtattctg accattccac aaagcctgga tagctggtgg   1680
accagcctga acttcctggg tggcaccacg gtttgcctgg gtcagggtgc gaaaagcgtg   1740
caacacctgg aaagcctgtt cacggcagtg acgaacttcc tgctgagcct gggcattcac   1800
ctgaacccta acaaaacaaa gagatggggt tactctttac atttcatggg ctatgtcatt   1860
ggatgttatg ggtcattgcc acaagatcac atcatacaaa agatcaaaga atgttttcga   1920
aaacttcctg ttaacagacc tattgattgg aaagtctgtc aacgtattgt gggtcttttg   1980
ggttttgctg ctccttttac acaatgtggt tatcctgctt taatgccttt gtatgcatgt   2040
attcagtcga agcaggcttt tactttctcg ccaacttaca aggcctttct gtgtaaacaa   2100
tacctgaacc tttaccctgt tgctcggcaa agaccaggtc tgtgccaagt gtttgctcac   2160
gcaaccccta ctggctgggg attggtcatg ggacatcagc gcatgcgtgg aacctttctg   2220
tgggcaagcg cacgctttag ctggctgagc ctgctggttc cgttcgtgca atggtttgtg   2280
ggtctgagcc caaccgtgtg gctgagcgtg tccagaaaat atacatcgtt tccatggctg   2340
ctaggctgtg ctgccaactg gatactgaga ggcaccagct tcgtgtatta tcccagcgct   2400
ctcaaccctt accatgatcc ttctcgaggt agactgggcc tgagcagacc tctgctgaga   2460
ctccccttcc gacccacaac cggaagaaca agcctgtatg ccgatagccc tagcgtcccc   2520
agccacctcc ctgatagagt ccattttgcc agcccactcc atgtggcctg gaggcctccc   2580
taaaagcttg atatcgaatt cacgcgtccc ccccctaacg ttactggccg aagccgcttg   2640
gaataaggcc ggtgtgcgtt tgtctatatg ttattttcca ccatattgcc gtcttttggc   2700
aatgtgaggg cccggaaacc tggccctgtc ttcttgacga gcattcctag gggtctttcc   2760
cctctcgcca aaggaatgca aggtctgttg aatgtcgtga aggaagcagt tcctctggaa   2820
gcttcttgaa gacaaacaac gtctgtagcg accctttgca ggcagcggaa ccccccacct   2880
ggcgacaggt gcctctgcgg ccaaaagcca cgtgtataag atacacctgc aaaggcggca   2940
caaccccagt gccacgttgt gagttggata gttgtggaaa gagtcaaatg gctctcctca   3000
agcgtattca acaaggggct gaaggatgcc cagaaggtac cccattgtat gggatctgat   3060
ctggggcctc ggtgcacatg ctttacatgt gtttagtcga ggttaaaaaa cgtctaggcc   3120
ccccgaacca cggggacgtg gttttccttt gaaaaacacg atgataatac catggatatc   3180
gatccctaca aggagttcgg tgccaccgtc gaactgctga gcttcctgcc cagcgatttc   3240
ttcccaagcg tacgtgacct tctagataca gcctcagctc tgtatcggga agccttagag   3300
tctcctgagc attgttcacc tcaccatact gctctcaggc aagcaattct gtgctgggga   3360
gaactaatga ctctagctac ctgggtgggt ggtaatttgg aagatccaat atccagggac   3420
ctagtagtca gttatgtcaa cactaatatg ggactaaagt tccgacaact attgtggttt   3480
cacatttctt gtctcacttt tggaagagaa acagttatag aatatttggt gtctttcgga   3540
gtgtggattc gcactcctcc agcttataga ccaccaaacg caccgatact gagcaccctg   3600
ccagaaacca ccgtggtgcg tcgtcgtggt cgcagcccac gcaggcgtac cccaagccca   3660
cgtcgtcgca gaagccagag cccacgacgt cgcaggagcc agagccgtga gagccagtgc   3720
taa                                                                  3723
```

<210> SEQ ID NO 18
<211> LENGTH: 10
<212> TYPE: PRT
<213> ORGANISM: artificial sequence
<220> FEATURE:
<223> OTHER INFORMATION: FLP peptide (core 18-27)

<400> SEQUENCE: 18

Phe Leu Pro Ser Asp Phe Phe Pro Ser Val
1 5 10

<210> SEQ ID NO 19
<211> LENGTH: 9
<212> TYPE: PRT
<213> ORGANISM: artificial sequence
<220> FEATURE:
<223> OTHER INFORMATION: ILC peptide (core 99-108)

<400> SEQUENCE: 19

Ile Leu Cys Trp Gly Glu Leu Met Thr
1 5

<210> SEQ ID NO 20
<211> LENGTH: 9
<212> TYPE: PRT
<213> ORGANISM: artificial sequence
<220> FEATURE:
<223> OTHER INFORMATION: VLQ peptide (env1)

<400> SEQUENCE: 20

Val Leu Gln Ala Gly Phe Phe Leu Leu
1 5

<210> SEQ ID NO 21
<211> LENGTH: 9
<212> TYPE: PRT
<213> ORGANISM: artificial sequence
<220> FEATURE:
<223> OTHER INFORMATION: FLG peptide (env1 41-49)

<400> SEQUENCE: 21

Phe Leu Gly Gly Thr Thr Val Cys Leu
1 5

<210> SEQ ID NO 22
<211> LENGTH: 10
<212> TYPE: PRT
<213> ORGANISM: artificial sequence
<220> FEATURE:
<223> OTHER INFORMATION: GLS peptide (env2)

<400> SEQUENCE: 22

Gly Leu Ser Pro Thr Val Trp Leu Ser Val
1 5 10

<210> SEQ ID NO 23
<211> LENGTH: 9
<212> TYPE: PRT
<213> ORGANISM: artificial sequence
<220> FEATURE:
<223> OTHER INFORMATION: SLY peptide (polymerase 816-824)

<400> SEQUENCE: 23

Ser Leu Tyr Ala Asp Ser Pro Ser Val
1 5

-continued

```
<210> SEQ ID NO 24
<211> LENGTH: 10
<212> TYPE: PRT
<213> ORGANISM: artificial sequence
<220> FEATURE:
<223> OTHER INFORMATION: VSA peptide (polymerase)

<400> SEQUENCE: 24

Val Ser Ala Ala Phe Tyr His Leu Pro Leu
1               5                   10


<210> SEQ ID NO 25
<211> LENGTH: 15
<212> TYPE: PRT
<213> ORGANISM: artificial sequence
<220> FEATURE:
<223> OTHER INFORMATION: N13F peptide (polymerase)

<400> SEQUENCE: 25

Asn Leu Asn Val Ser Ile Pro Trp Thr His Lys Val Gly Asn Phe
1               5                   10                  15


<210> SEQ ID NO 26
<211> LENGTH: 15
<212> TYPE: PRT
<213> ORGANISM: artificial sequence
<220> FEATURE:
<223> OTHER INFORMATION: F13L peptide (env)

<400> SEQUENCE: 26

Phe Leu Trp Glu Trp Ala Ser Ala Arg Phe Ser Trp Leu Ser Leu
1               5                   10                  15
```

METHODS FOR TREATING OR PREVENTING HBV INFECTION OR HBV RELATED DISEASES

CROSS-REFERENCE TO RELATED APPLICATIONS

This application is a Continuation Application of U.S. patent application Ser. No. 15/369,118, filed on Dec. 5, 2016, now U.S. Pat. No. 10,190,105, issued on Jan. 29, 2019, which is a Divisional Application of U.S. patent application Ser. No. 14/232,082, filed on Jan. 10, 2014, now U.S. Pat. No. 9,512,412, issued on Dec. 6, 2016, which is a U.S. National Stage patent application pursuant to 35 U.S.C. § 371 of International Patent Application PCT/EP2012/063640, filed on Jul. 12, 2012, and published as WO 2013/007772 on Jan. 17, 2013, which Claims priority to European Patent Application 12305450.4 filed on Apr. 18, 2012, and European Patent Application 11305909.1 filed on Jul. 12, 2011, the content of each is hereby expressly incorporated by reference in their entireties for all purposes.

FIELD OF THE INVENTION

The present invention relates to polymerase HBV mutant polypeptides comprising a mutated polymerase domain which is functionally disrupted for polymerase activity and fusion proteins comprising such polymerase mutant polypeptide. The present invention also relates to a nucleic acid molecule and an expression vector for expressing said polymerase mutant polypeptide as well as a composition which can be used for eliciting an immune response to HBV with the goal of providing a protective or therapeutic effect against HBV infection. The invention is of very special interest in the field of immunotherapy, and more particular for treating patients infected with HBV, especially those chronically infected.

BACKGROUND OF THE INVENTION

Hepatitis B is a major public health problem with more than 350 million persons chronically infected worldwide, 20 to 40% of them being at risk of developing chronic liver disease, cirrhosis and hepatocellular carcinoma. Despite the existence of effective preventive vaccines, the hepatitis B virus (HBV) infection is still rampant in many countries, even developed ones, with an estimation of 4.5 millions of new cases of infection per year worldwide. Unlike the WHO recommendation which is to implement universal vaccination, the coverage of full course preventive vaccination varies from 25% in Asia to 75-90% in Europe. Currently hepatitis B is the $10^{th}$ cause of mortality (around 1 million of deaths/year) and HBV related liver carcinoma, the $5^{th}$ most frequent cancer. Geographic repartition of HBV infection is uneven with prevalence lower than 1% in Western countries to more than 10% in South Eastern countries, most part of Africa and Equatorial South America.

Hepatitis B virus is a member of the hepadnaviridae and primarily infects the liver, replicating in hepatocytes. The infectious particles are the so called 42-45 nm "Dane particles" which consist of an outer lipoprotein envelope with three different surface proteins (HBs) and an inner nucleocapsid, the major structural protein of which is the core protein (HBcAg). Within the nucleocapsid is a single copy of the HBV genome linked to the viral polymerase protein (P). In addition to 42-45 nm virions, the blood of HBV-infected patients contains 20-nm spheres made of HBsAg and host-derived lipids which are released from infected cells. These spheres outnumber the virions by a factor of $10^4$-$10^6$.

After virions enter hepatocytes, by an as-yet-unknown receptor, nucleocapsids transport the genomic HBV DNA to the nucleus, where the relaxed circular DNA is converted to covalently closed circular DNA (cccDNA). The cccDNA functions as the template for the transcription of four viral RNAs, which are exported to the cytoplasm and used as mRNAs for translation of the HBV proteins. The longest (pre-genomic) RNA also functions as the template for HBV replication, which occurs in nucleocapsids in the cytoplasm. Some of the HBV DNA and polymerase-containing capsids are then transported back to the nucleus, where they release the newly generated relaxed circular DNA to form additional cccDNA. With a half-life longer than the one of hepatocytes, the cccDNA is responsible for the persistence of HBV. Other capsids are enveloped by budding into the endoplasmic reticulum and secreted after passing through the Golgi complex.

Structural and functional organization of the HBV genome has been investigated for more than 30 years. The HBV genome is a relaxed circular partially double-stranded DNA of approximately 3,200 nucleotides consisting of a full-length negative strand and a shorter positive strand. It contains 4 overlapping open reading frames (ORFs), C, S, P and X. The C ORF encodes the core protein (or HBcAg), a 183 amino acid-long protein constitutive of the nucleocapsid and a second protein found in the serum of patients during virus replication known as HBeAg which contains a precore N-terminal extension and a part of HBcAg. The C-terminus of the core protein is very basic and contains 4 Arg-rich domains which are predicted to bind nucleic acids as well as numerous phosphorylation sites. The S ORF encodes three surface proteins all of which have the same C terminus but differ at their N-termini due to the presence of three in-frame ATG start codons that divide the S ORF into three regions, S (226 amino acids), pre-S2 (55 amino acids) and pre-S1 (108 amino acids), respectively. The large-surface antigen protein (L) is produced following translation initiation at the first ATG start codon and comprises 389 amino acid residues (preS1-preS2-S). The middle surface antigen protein (M) results from translation of the S region and the pre-S2 region starting at the second start ATG whereas the small surface antigen protein of 226 amino acids (S, also designated HBsAg) results from translation of the S region initiated at the third start ATG codon. The HBV surface proteins are glycoproteins with carbohydrate side chains (glycans) attached by N-glycosidic linkages. The P ORF encodes the viral polymerase and the X ORF a protein known as the X protein which is thought to be a transcriptional activator.

The viral polymerase is about 832-845 amino acid residues long according to the HBV genotype and it is encoded in a long open reading frame ("P") that overlaps the 3'end of the core gene and all the surface protein genes. The viral polymerase is a multifunctional protein composed of four domains, including three functional domains, respectively the terminal protein, polymerase and RNase H domains that catalyse the major steps in HBV replication (priming, DNA synthesis and removal of RNA templates) as well as a non-essential spacer domain present between the terminal protein and polymerase domains (see for example Radziwill et al., 1990, J. Virol. 64:613; Bartenschlager et al., 1990, J. Virol. 64, 5324). The catalytic sites responsible for enzymatic activities have been characterized. In this regard, four residues forming the conserved YMDD motif (residues 538 to 541 numbered with respect to the 832 residue long polymerase) have been shown essential to the DNA- and RNA-dependent DNA polymerase activity whereas RNase H activity is based on a DEDD motif involving four non-consecutive amino acid residues, respectively Asp (D) in position 689, Glu (E) in position 718, Asp (D) in position 737 and Asp (D) in position 777 as well as few other amino acid residues including Val (V) in position 769 and Thr (T) in position 776. Different mutations have been described in the art that abolish the RT polymerase and RNase H activities (Chang et al., 1990, J. Virol. 64: 5553; Bartenschlager et al., 1990, J. Virol. 64, 5324, Radziwill et al., 1990, J. Virol. 64:613 and Chen et al., 1996, J. Virol. 70:6151). Several groups have succeeded in expressing HBV polymerase protein in various host system, but its expression has been reported toxic for the expressing cells, requiring the use of inducible promoters (Choi et al., 2002, Antiviral Res. 55:279; Karimi et al., 2002, J. Virol. 76:8609).

A number of preclinical and clinical studies have emphasized the importance of CD4+ and CD8+ T cell immune responses for effective anti-viral response. It was indeed observed that patients naturally having recovered from hepatitis B mounted multi-specific and sustained responses mediated by T helper ($T_H$) and cytotoxic T (CTL) lymphocytes which are readily detectable in peripheral blood. Appearance of anti-HBe and anti-HBs antibodies indicates a favorable outcome of infection. HBsAg-specific antibodies are neutralizing, mediate protective immunity and persist for life after clinical recovery.

Chronic HBV infection is, however, only rarely resolved by the immune system. The vast majority of chronically infected patients show weak and temporary CD4 and CD8 T cell immune responses that are antigenically restricted and ineffective to clear viral infection. The reason for this alteration of the effector functions of the cellular immune response in chronic hepatitis B is currently not well-understood even if the involvement of different inhibitory molecules that are up-regulated in HBV chronically infected patients, such PD-1, CTLA4 . . . etc, has been observed. Therefore, there is a need for immunomodulatory strategies capable of inducing an effective T-cell response.

Conventional treatment of chronic hepatitis B includes pegylated interferon-alpha (IFNa) and nucleoside/nucleotide analogues (NUCs) such as lamivudine, and more recently entecavir, telbivudine, adefovir and tenofovir. IFNa is a potent antiviral molecule, whereby inhibiting viral replication, which however, causes serious side effects in merely 25-30% of patients. NUCs act as competitive inhibitors of HBV polymerase aimed to inhibit the reverse transcription of the pre-genomic RNA into the negative DNA strand and then the double stranded viral DNA. They limit the formation of new virions, but are ineffective to eliminate the supercoiled cccDNA hidden in the nucleus of infected hepatocytes which constitutes a source of new progeny viruses. This can explain why NUC efficacy is temporary and viral rebound occurs immediately after cessation of treatment, requiring patients to stay lifelong under treatment. In addition, long-term efficacy is also limited due to emergence of resistant HBV mutants (more than 24% after one year and approximately 66% after four years of lamivudine treatment as reported in some studies although newer NUCs showed much fewer occurrences of drug-resistant HBV mutants). A number of HBV strains exhibiting a decreased sensitivity to anti-viral agents have now been isolated and genome sequencing revealed high spot of substitution mutations in the polymerase domain, including in the YMDD motif (US2008-0233557; Zoulim and Locarnini, 2009, Gastroenterology, 137:1593).

Besides antiviral therapies, efforts are currently made to develop supplemental therapies aiming at improved host's immune responses, specifically those mediated by cytotoxic T and helper T lymphocytes. Several encouraging vaccine strategies have focused on HBV surface proteins S, preS1 and/or preS2 (Zanetti et al., 2008, Vaccine 26: 6266; Mancini-Bourguine et al., 2006, Vaccine 24:4482) as well as on multivalent immunotherapy approaches aimed to simultaneously target multiple HBV antigens. For example, immunization with a polyepitope DNA vaccine encoding multiple envelope, core and polymerase epitopes was shown to elicit CTL and $T_H$ responses in preclinical mouse models (Depla et al., 2008, J. Virol. 82: 435). An approach based on a mixture of DNA plasmids encoding HBsAg, HBcAg and HBV polymerase (WO2005/056051; WO2008/020656) demonstrated specific anti-HBV cellular and humoral responses in transgenic mouse model of chronic hepatitis B (Chae Young Kim et al., 2008, Exp. Mol. Medicine 40: 669). Phase I clinical trials were initiated in South Korea in HBV carriers in combination with lamivudine treatment (Yang et al., 2006, Gene Ther. 13: 1110). Another approach recently investigated involves the use of a vectored therapeutic vaccine encoding a combination of HBc and HBV polymerase together with Hbs immunogenic domains (WO2011/01565). Mice immunized with Ad-vectorized vaccine showed T cell response against all expressed HBV antigens, especially against polymerase.

One may expect that HBV will continue to be a serious global health threat for many years due to the chronic and persistent nature of the infection, its high prevalence, the continuing transmission of HBV and the significant morbidity of the associated diseases. Thus, there is an important need to develop more effective approaches for improving prevention and treatment of HBV infections or HBV-associated diseases or disorders. In particular, there still exists a need for approaches that conciliate T cell-mediated immunity against the targeted HBV antigen(s), especially against core, and low potential toxicity. Such approaches are especially useful for treating subjects chronically infected with HBV.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

SUMMARY OF THE INVENTION

In one aspect, the present invention concerns a mutant polymerase polypeptide which comprises at least 500 amino acid residues of a native HBV polymerase wherein said mutant polymerase polypeptide comprises a polymerase domain with an internal deletion that functionally disrupts the polymerase activity and wherein said internal deletion includes at least the YMDD motif naturally present in the polymerase domain of a native polymerase.

The present invention also concerns a nucleic acid molecule encoding said mutant polymerase polypeptide, a vector comprising said nucleic acid molecule, or a composition comprising or encoding said mutant polymerase polypeptide.

The present invention also relates to the use of this mutant polymerase polypeptide, nucleic acid molecule, vector or composition, preferably in combination with additional polypeptides (e.g. with one or more HBV polypeptide(s)) for the purpose of treating, preventing or inhibiting an HBV infection or ameliorating a condition associated with an HBV infection.

Still a further aspect of the present invention includes a method of treating, preventing or inhibiting HBV infection or ameliorating a condition associated with HBV infection in a subject in need thereof, comprising providing or administering this mutant polymerase polypeptide, nucleic acid molecule, vector or composition, eventually in combination with additional polypeptides (e.g. with one or more HBV polypeptide(s)) and/or with the standard of care.

Still yet a further aspect of the present invention concerns a method of eliciting an immune response in a subject in need thereof, comprising providing or administering this mutant polymerase polypeptide, nucleic acid molecule, vector or composition, eventually in combination with additional polypeptides (e.g. with one or more HBV polypeptide(s)) and/or with the standard of care, for the purpose of inducing or stimulating an immune response in this subject or for treating an HBV infection or ameliorating a condition or symptom associated with HBV infection.

Still more aspect of the present invention provides a kit of parts comprising a plurality of containers and instructions for providing or administering to a subject this mutant polymerase polypeptide, nucleic acid molecule, vector or composition, eventually in combination with additional polypeptides (e.g. with one or more HBV polypeptide(s)), in accordance with the compositions and methods described herein.

DETAILED DESCRIPTION OF THE INVENTION

The present invention provides a mutant polymerase polypeptide which comprises a mutated polymerase domain with an internal deletion that functionally disrupts the polymerase activity, wherein said internal deletion comprises at least the YMDD motif naturally present in the polymerase domain of a native HBV polymerase. Such a mutant polymerase polypeptide or vector encoding it can be used in compositions and methods for the treatment or prevention of an HBV infection or a condition associated with an HBV infection, eventually in combination with other HBV polypeptides and/or standard of care. This invention permits to envisage expression and production of the mutant polymerase polypeptide in various vector systems due to the disruption of the associated enzymatic activities. The invention is also particularly adapted for human use and may be used to reinforce standard therapies (e.g. SOC). Immunization of animal models with a vector encoding this mutant polymerase polypeptide in fusion with HBc and Hbs immunogenic domains, elicited HBV specific T cell responses, and surprisingly a strong immunity against both HBc and Polymerase was observed The following section provides a greater explanation of the meaning of some of the terms used herein.

Definitions

As used herein throughout the entire application, the terms "a" and "an" are used in the sense that they mean "at least one", "at least a first", "one or more" or "a plurality" of the referenced compounds or steps, unless the context dictates otherwise.

The term "and/or" wherever used herein includes the meaning of "and", "or" and "all or any other combination of the elements connected by said term".

The term "about" or "approximately" as used herein means within 10%, preferably within 8%, and more preferably within 5% of a given value or range.

The terms "amino acids", "residues" and "amino acid residues" are synonyms and encompass natural amino acids as well as amino acid analogs (e.g. non-natural, synthetic and modified amino acids, including D or L optical isomers).

The terms "polypeptide", "peptide" and "protein" refer to polymers of amino acid residues which comprise at least nine or more amino acids bonded via peptide bonds. The polymer can be linear, branched or cyclic and may comprise naturally occurring and/or amino acid analogs and it may be interrupted by non-amino acids. As a general indication, if the amino acid polymer is more than 50 amino acid residues, it is preferably referred to as a polypeptide or a protein whereas if it is 50 amino acids long or less, it is referred to as a "peptide".

As used herein, when used to define products, compositions and methods, the term "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are open-ended and do not exclude additional, unrecited elements or method steps. Thus, a polypeptide "comprises" an amino acid sequence when the amino acid sequence might be part of the final amino acid sequence of the polypeptide. Such a polypeptide can have up to several hundred additional amino acids residues. "Consisting essentially of" means excluding other components or steps of any essential significance. Thus, a composition consisting essentially of the recited components would not exclude trace contaminants and pharmaceutically acceptable carriers. A polypeptide "consists essentially of" an amino acid sequence when such an amino acid sequence is present with eventually only a few additional amino acid residues. "Consisting of" means excluding more than trace elements of other components or steps. For example, a polypeptide "consists of" an amino acid sequence when the polypeptide does not contain any amino acids but the recited amino acid sequence.

As used herein, "HBV" and "hepatitis B virus" are used interchangeably and refer to any member of the hepadnaviridae (see e.g. Ganem and Schneider in Hepadnaviridae (2001) "The viruses and their replication", pp 2923-2969, Knipe D M et al., eds. Fields Virology, 4th ed. Philadelphia, Lippincott Williams & Wilkins or subsequent edition). Amino acid sequences of the various HBV polypeptides and the encoding nucleotide sequences can be found in specialized data banks (e.g. those mentioned above) and in the literature (see e.g. Valenzuela et al., 1980, The nucleotide sequence of the hepatitis B viral genome and the identification of the major viral genes (pp 57-70) in "Animal Virus Genetics"; eds B. Fields, et al.; Academic Press Inc., New York and Vaudin et al., 1988, J. Gen. Virol. 69: 1383).

As used herein, the term "HBV polymerase" refers to a polypeptide that retains at least 500 amino acid residues comprised in a native HBV polymerase protein. Desirably, such at least 500 amino acid residues are spread over the three functional domains and preferably over the four domains normally present in a native HBV polymerase. This term encompasses native (i.e. naturally-occurring) polymerase polypeptides of any HBV strain, isolate or genotype that can be found, isolated, obtained from a source of HBV in nature such as those cited above in connection with the term "HBV" as well as modified polymerase (i.e. mutant polymerase polypeptide) and fragments thereof. For purpose of illustration, the amino acid residues for HBV polymerase described herein are numbered by reference to a 832 amino acids long polymerase with the residue Tyr in the motif Tyr Met Asp Asp (YMDD) being residue number 538. It is within the reach of the skilled person to adapt the numeration of the amino acid residues to other polymerases (e.g. 843 or 845 amino acid long).

As used herein, the term "native" or "naturally-occurring" when used in connection with any amino acid sequence (e.g. peptide, polypeptide, protein, etc) or nucleotide sequence (e.g. gene, nucleic acid molecule, polynucleotide, etc) refers to an amino acid sequence or to a nucleotide sequence that can be found, isolated, obtained from a source in nature as distinct from one being artificially modified or mutated by man in the laboratory (i.e. mutant). Such sources in nature include biological samples (e.g. blood, plasma, sera, semen, saliva, tissue sections, biopsy specimen etc.) collected from an organism infected or that has been exposed to HBV, cultured cells (such as HepG2.2.15, HuH6-C15 (Sureau et al., 1986, Cell 47:37; Sells et al., 1987, Proc. Natl. Acad. Sci. 84(4):1005); HuH7.TA61 or HuH7.TA62 (Sun et al., 2006, J Hepatol. 45(5):636), tissue cultures as well as recombinant materials. Recombinant materials include without limitation HBV isolates (e.g. available in depositary institutions), HBV genome, genomic RNA or cDNA libraries, vectors containing HBV genome or fragment(s) thereof or any prior art vector known to include such elements).

For purpose of illustration, a "native HBV polymerase" means a HBV polymerase encoded by the ORF P of any naturally-occurring HBV genotype, strain or isolate described in the art (e.g. a polypeptide of 832 to 845 amino acids depending of the genotype) or fragment thereof. The term "native" also encompasses HBV polymerase polypeptide/peptides that are representative of a specific genotype, and thus comprise an amino acid sequence corresponding to a consensus or near consensus sequence which is typically determined after sequence alignment of various HBV polymerases of a particular genotype.

The term "mutant" as used herein refers to a polypeptide exhibiting one or more mutation(s) with respect to the native counterpart. For illustrative purposes, a "mutant polymerase polypeptide" refers to a polymerase polypeptide that originates from a native polymerase after being artificially mutated or altered by man in the laboratory as described herein. Any mutation(s) can be envisaged, including substitution, insertion and/or deletion of one or more nucleotide/amino acid residue(s), non-natural arrangements (e.g. fusion with foreign polypeptides/peptides) as well as any combination of these possibilities. When several mutations are contemplated, they can concern consecutive residues and/or non-consecutive residues. Mutation(s) can be generated by a number of ways known to those skilled in the art, such as site-directed mutagenesis (e.g. using the Sculptor™ in vitro mutagenesis system of Amersham, Les Ullis, France), PCR mutagenesis, DNA shuffling and by chemical synthetic techniques (e.g. resulting in a synthetic nucleic acid molecule). According to preferred embodiments, the mutation(s) contemplated by the present invention encompass deletion(s) and/or substitution(s) of one or more amino acid residue(s) (consecutive or not) involved directly or indirectly in at least one enzymatic activity exhibited by a native HBV polymerase, with the aim of disrupting said at least one enzymatic activity such as the polymerase activity and/or the RNaseH activity. In the context of the invention, the resulting mutant polymerase polypeptide globally retains a high degree of identity (e.g. at least 80%) with the corresponding native HBV polymerase in the non-mutated portions.

The term "disrupt" as used herein in connection with a given enzymatic activity or any derivative such as "disrupting" means "abolish" (no residual activity at all) or "significantly reduce" (residual activity of less than 20% of the activity exhibited by the native polymerase).

The term "identity" refers to an exact amino acid to amino acid or nucleotide to nucleotide correspondence between two polypeptide or nucleotide sequences. The percentage of identity between two sequences is a function of the number of identical positions shared by the sequences, taking into account the number of gaps which need to be introduced for optimal alignment and the length of each gap. Various computer programs and mathematical algorithms are available in the art to determine the percentage of identity between amino acid sequences, such as for example the Blast program available at NCBI or ALIGN in Atlas of Protein Sequence and Structure (Dayhoff ed., 1981, Suppl., 3 482-489). Programs for determining homology between nucleotide sequences are also available in specialized data base (e.g. Genbank, the Wisconsin Sequence Analysis Package, BESTFIT, FASTA and GAP programs). For illustrative purposes, "at least 80% sequence identity" as used herein means 80%, 81%, 82%, 83%, 84%, 85%, 86%, 87%, 88%, 89%, 90%, 91%, 92%, 93%, 94%, 95%, 96%, 97%, 98%, 99% or 100%.

As used herein, the term "isolated" refers to a protein, polypeptide, peptide, polynucleotide, plasmid vector, viral vector, or host cell that is removed from its natural environment (i.e. separated from at least one other component(s) with which it is naturally associated).

HBV Sequence

A number of HBV sequences are suitable for use in the embodiments described herein including such sequences that are readily available to investigators in the field, including, but not limited to, HBV sequences described in Genbank and PubMed. For illustrative purposes, extensive phylogenetic analyses have led to the classification of hepatitis B viruses into 8 major genotypes (A to H) which show distinct geographic distribution and clinical outcome although exhibiting high degree of sequence conservation. The various HBV were also classified in nine different subtypes (ayw1, ayw2, ayw3, ayw4, ayr, adw2, adw4, adrq+ and adqr−) in connection with HBsAg-associated serology (see review by Mamum-Al Mahtab et al., 2008, Hepatobiliary Pancrease Dis Int 5: 457; Schaeffer, 2007, World Gastroenterol. 7: 14). Each genotype and serotype encompasses different HBV strains and isolates. An isolate corresponds to a specific virus isolated from a particular source of HBV (e.g. a patient sample or other biological HBV reservoir) whereas a strain encompasses various isolates which are very close each other in terms of genomic sequences.

Exemplary HBV of genotype A include without limitation isolate HB-JI444AF and strain HB-JI444A (accession number AP007263). Exemplary HBV of genotype B include without limitation clone pJDW233 (accession number D00329), isolate HBV/14611 (accession number AF121243), HBV-B1 (GenBank accession number AF282917.1), HBV strain Whutj-37 (GenBank accession number AY2933309.1), the Chinese HBV strain GDH1 (GenBank accession number AY766463.1) and HBV isolate 57-1 subtype adw (GenBank accession number AY518556.1). Exemplary HBV of genotype C include without limitation isolate AH-1-ON980424 (accession number AB13879), strain HCC-3-TT (accession number AB113877), HBV isolate SWT3.3 (GenBank accession number EU916241.1), HBV isolate H85 (GenBank accession number AY306136.1), HBV strain C1248 (GenBank accession number DQ975272.1), HBV isolate CHN-H155 (GenBank accession number DQ478901.1) and HBV isolate GZ28-1 (GenBank accession number EF688062). Exemplary HBV of genotype D include without limitation isolates KAMCHATKA27 (accession number AB188243), ALTAY136 (accession number AB188245) and Y07587 (Genbank accession number Y07587 and Stoll-Becker et al., 1997, J. Virol. 71: 5399) as well as the HBV isolate described under accession number AB267090. Exemplary HBV of genotype E include without limitation isolate HB-JI411F and strain HB-JI411 (accession number AP007262). Exemplary HBV of genotype F include without limitation isolates HBV-BL597 (accession number AB214516) and HBV-BL592 (accession number AB166850). Exemplary HBV of genotype G include without limitation isolate HB-JI444GF and strain HB-JI444G (accession number AP007264). Exemplary HBV of genotype H include without limitation isolate HBV ST0404 (accession number AB298362) and isolate HB-JI260F and strain HB-JI260 (accession number AP007261).

It is intended that the present invention is not limited to these exemplary HBV sequences. Indeed the nucleotide and amino acid sequences of any or all of the HBV polypeptides/peptides used in accordance with the present invention can vary between different HBV isolates and genotypes and this natural genetic variation is included within the scope of the invention. Moreover, the HBV polypeptides/peptides in use in the invention can be representative of a specific genotype, and thus comprise an amino acid sequence corresponding to a consensus or near consensus sequence.

In addition, each of HBV polypeptides/peptides may originate independently from any HBV genotype, strain or isolate identified at present time, such as any of those described above in connection with the term "HBV". Such a configuration may permit to provide protection against a broader range of HBV genotypes or adaptation to a specific geographic region by using HBV genotype(s) that is/are endemic in this region or to a specific population of patients. In this regard, genotypes A and C are the most prevalent in the United States, genotypes A and D in Western European countries and genotype D in the Mediterranean basin whereas genotypes B and C are the most common in China. Limited data from India suggest that genotypes A and D are most prevalent in India. It is within the reach of the skilled person to choose appropriate HBV genotypes, serotypes, strains and/or isolates according to the population and/or geographic region to be treated by.

According to a preferred embodiment, the HBV polypeptides/peptides in use in the invention originate from a genotype D virus, with a specific preference for HBV isolate Y07587.

Mutant HBV Polymerase

The mutant polymerase polypeptide of the description comprises a mutated polymerase domain with an internal deletion that functionally disrupts the polymerase activity and includes at least the YMDD motif naturally present in the polymerase domain of a native polymerase. The disruption of the polymerase activity exhibited by the resulting mutant polymerase polypeptide can be evaluated using assays well known in the art (e.g. the endogenous polymerase assays described in Radziwill et al., 1990, J Virol. 64:613).

A generic amino acid sequence encompassing the polymerase domain of native HBV polymerases of genotypes B, C and D is provided in SEQ ID NO: 1, with the residue Xaa in position 7 being Thr (T) or Ala (A); the residue Xaa in position 13 being Asn (N), Arg (R) or His (H); the residue Xaa in position 16 being Ile (I) or Thr (T); the residue Xaa in position 38 being Thr (T) or Ala (A); the residue Xaa in position 53 being Ser (S) or Asn (N); the residue Xaa in position 54 being Thr (T) or Tyr (Y); the residue Xaa in position 55 being His (H) or Arg (R); the residue Xaa in position 91 being Ile (I) or Leu (L); the residue Xaa in position 109 being Pro (P) or Ser (S); the residue Xaa in position 118 being Thr (T) or Asn (N); the residue Xaa in position 121 being Asn (N) or Ile (I); the residue Xaa in position 122 being Ile (I) or Phe (F); the residue Xaa in position 124 being Tyr (Y) or Asn (N); the residue Xaa in position 127 being Gly (G) or Arg (R); the residue Xaa in position 131 being Asp (D) or Asn (N); the residue Xaa in position 134 being Asp (D) or Asn (N); the residue Xaa in position 145 being Leu (L) or Met (M); the residue Xaa in position 149 being Lys (K) or Gln (Q); the residue Xaa in position 151 being Phe (F) or Tyr (Y); the residue Xaa in position 221 being Phe (F) or Tyr (Y); the residue Xaa in position 222 being Thr (T) or Ala (A); the residue Xaa in position 223 being Ser (S) or Ala (A); the residue Xaa in position 224 being Ile (I) or Val (V); the residue Xaa in position 238 being Asn (N) or His (H); the residue Xaa in position 248 being Asn (N) or His (H); the residue Xaa in position 256 being Ser (S) or Cys (C); the residue Xaa in position 257 being Trp (W) or Tyr (Y); the residue Xaa in position 259 being Thr (T) or Ser (S); the residue Xaa in position 263 being Glu (E) or Asp (D); the residue Xaa in position 266 being Val (V) or Ile (I); the residue Xaa in position 267 being Leu (L) or Gln (Q); the residue Xaa in position 271 being Gln (Q), Met (M) or Glu (E); the residue Xaa in position 317 being Ser (S) or Ala (A); and the residue Xaa in position 332 being Cys (T) or Ser (S).

In accordance with the present invention, the mutated polymerase domain comprised in the mutant polymerase polypeptide of the invention lacks at least the YMDD motif present from position 203 to position 206 of such generic polymerase domain of SEQ ID NO: 1.

The present invention also encompasses any other internal deletion of at least 4 amino acid residues and at most 30 amino acid residues which comprises at least this YMDD motif.

A representative mutant polymerase polypeptide according to the invention comprises a mutated polymerase domain comprising the amino acid sequence shown in SEQ ID NO:1 but lacking at least the Tyr residue in position 203, the Met residue in position 204, the Asp residue in position 205 and the Asp residue in position 206.

Further to the YMDD motif, it is preferred that the internal deletion also encompasses all or parts of the neighboring VVL motif present at the C terminus of the YMDD motif in a native HBV polymerase domain (corresponding to residues in positions 207-209 of SEQ ID NO: 1 and to residues in position 542-544 of a native polymerase of 832 amino acids). Such VVL motif can indeed contribute to the formation of "junctional" epitopes (e.g. colinearly synthesized new epitopes) which are at risk of reducing or silencing the host's immune response directed against one or more of the HBV polymerase-associated epitopes.

Preferably, the mutant polymerase polypeptide of the invention comprises a mutated polymerase domain having the amino acid sequence shown in SEQ ID NO: 1 but lacking at least the Tyr residue in position 203, the Met residue in position 204, the Asp residue in position 205, the Asp residue in position 206, the Val residue in position 207, the Val residue in position 208 and the Leu residue in position 209.

More preferably, the mutant polymerase polypeptide of the invention comprises a polymerase domain comprising, alternatively essentially consisting of, or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 2. Even more preferably, the mutated polymerase domain comprises the amino acid sequence shown in SEQ ID NO: 2.

Alternatively or in combination, the mutant polymerase polypeptide of the invention also comprises a mutated RNaseH domain comprising mutation(s) of one or more amino acid residue(s) that functionally disrupt the RNaseH activity normally exhibited by a native HBV polymerase.

As discussed above, the functional domain involved in RNase H activity has been mapped within the C-terminal portion, more particularly from position 680 to the C-terminus of a native 832 amino acid long HBV polymerase (or from position 693 to the C-terminus of a native 845 amino acid long HBV polymerase) and the present invention encompasses any mutation(s) in this domain that correlate with disruption of the RNase H activity (i.e. eventually leading to a weak residual activity less than 20% of the native RNaseH activity). Disruption of the RNase H activity exhibited by the mutant polymerase polypeptide can be evaluated using assays well known in the art (e.g. in vitro RNaseH activity assays or DNA-RNA tandem molecule analysis described in Radziwill et al., 1990, J Virol. 64:613 or in Lee et al., 1997, Biochem. Bioph. Res. Commun. 233(2):401).

A generic amino acid sequence encompassing the RNaseH domain of native HBV polymerases of genotypes B, C and D is provided in SEQ ID NO: 3, with the residue Xaa in position 2 being Ser (S) or Pro (P); the residue Xaa in position 19 being Ala (A) or Val (V); the residue Xaa in position 20 being Ile (I) or Met (M); the residue Xaa in position 30 being Val (V) or Leu (L); the residue Xaa in position 31 being Ala (A) or Ser (S); the residue Xaa in position 53 being Lys (K) or Asn (N); the residue Xaa in position 54 being Leu (L) or Ile (I); the residue Xaa in position 55 being Leu (L) or Ile (I); the residue Xaa in position 97 being Ala (A) or Thr (T); the residue Xaa in position 108 being Tyr (Y) or Ser (S); the residue Xaa in position 115 being Pro (P) or Leu (L); the residue Xaa in position 116 being Phe (F) or Tyr (Y); the residue Xaa in position 128 being Val (V) or Asp (D).

Advantageously, the one or more mutation(s) comprised in the RNaseH domain of the mutant polymerase polypeptide of the invention are selected from the group consisting of:

- a deletion of at least 8 amino acids and at most 60 amino acids including at least the portion of SEQ ID NO: 3 extending from approximately the Glu residue (E) in position 39 to approximately the Ala (A) residue in position 46 (del ELLAACFA);
- the substitution of the Asp (D) residue in position 10 of SEQ ID NO: 3 with an amino acid residue other than D;
- the substitution of the Val (V) residue in position 90 of SEQ ID NO: 3 with an amino acid residue other than V;
- the substitution of the Thr (T) or Ala (A) residue in position 97 of SEQ ID NO: 3 with an amino acid residue other than T or A;
- the substitution of the Asp (D) residue in position 98 of SEQ ID NO: 3 with an amino acid residue other than D; and any combination thereof.

Representative examples of appropriate combinations include without limitation (a) the substitutions of amino acid residues in position 10, 90, 97 and 98; (b) the deletion of 8 to 60 amino acid residues including the GLLAACFA motif and the substitutions of amino acid residues at any of the cited positions; or (c) the combination of all listed mutations.

Suitably, the substituted residue(s) in position 10, 90, 97 or 98 of SEQ ID NO: 3 are individually replaced with a His (H) residue or with a Tyr (Y) residue, with a specific preference for the residue in position 10 of SEQ ID NO: 3 substituted with a His (H) residue (D689H), the residue in position 90 of SEQ ID NO: 3 substituted with a Tyr (Y) residue (V769Y), the residue in position 97 of SEQ ID NO: 3 substituted with a Tyr (Y) residue (T776Y or A776Y) and/or the residue in position 98 of SEQ ID NO: 3 substituted with a His (H) residue (D777H).

Suitably, the deletion comprised in the mutated RNase H domain includes a portion of at least 19 amino acid residues extending from approximately the Glu residue (E) in position 39 to approximately the Thr (T) residue in position 57 of SEQ ID NO: 3, preferably a portion of at least 25 amino acids extending from approximately the Glu residue (E) in position 39 to approximately the Leu (L) residue in position 63 of SEQ ID NO: 3, and more preferably a portion of at least 33 amino acids extending from approximately the residue Xaa (A or S) in position 31 to approximately the Leu (L) residue in position 63 of SEQ ID NO: 3.

Preferably, the mutant polymerase polypeptide of the invention comprises a mutated RNaseH domain comprising the amino acid sequence shown in SEQ ID NO: 3 but (a) lacking the portion of 33 amino acid residues extending from the residue Xaa (X) in position 31 to approximately the Leu (L) residue in position 63 and comprising (b) the substitution of the Asp (D) residue in position 10 with a His (H) residue (D689H); (c) the substitution of the Val (V) residue in position 90 with a Tyr (Y) residue (V769Y); (d) the substitution of the residue in position 97 with a Tyr (Y) residue (T/A776Y) and (e) the substitution of the Asp (D) residue in position 98 with a His (H) residue (D777H).

More preferably, the mutant polymerase polypeptide of the invention comprises a mutated RNaseH domain comprising, alternatively essentially consisting of, or alternatively consisting of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 4.

In an even more preferred embodiment, the mutant polymerase polypeptide of the invention comprises, alternatively essentially consists of, or alternatively consists of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 5. Still even more preferred is a mutant polymerase polypeptide comprising the amino acid sequence shown in SEQ ID NO: 5.

In the context of the invention, the mutant polymerase polypeptide of the invention can comprise additional mutation(s). However, it is preferred to avoid modification(s) that can be detrimental to the immunogenic activity, especially in portions rich in B, CTL and/or $T_H$ epitopes.

Exemplary additional modifications include N-terminal truncation. Particularly appropriate is truncation of at least 20 amino acid residues and at most 100 amino acid residues normally present at the N-terminus of a native HBV polymerase or of SEQ ID NO: 5, with a specific preference for a truncation extending from position 1 (Met initiator) or 2 to approximately position 47 of SEQ ID NO: 5. This modification is particularly relevant for mutant polymerase polypeptide used in combination with a native HBV core polypeptide due to the fact that such a N-terminal truncation contributes to reduce or delete the overlapping portions between these two polypeptides. However, the same can be achieved by using a non-truncated mutant polymerase polypeptide in combination with a C-terminal truncated HBV core polypeptide as described below.

Desirably, the resulting mutant polymerase polypeptide retains immunogenic properties, in particular a capacity to stimulate a cell-mediated immune response, within the same range as or alternatively higher than the native polymerase.

Combination/Fusion with Other Polypeptide(s)

In another embodiment the mutant polymerase polypeptide of the invention can be used in combination with one or more additional polypeptide(s) or peptide(s).

The term "combination" and variation such as "combined use" refers to the action of administering in the same host organism two or more entities, one of which being an object of the invention. Typically, the at least two entities can be administered by different routes and according to different time schedule. A suitable combination includes without limitation the combination of the mutant polymerase polypeptide described herein (or a vector encoding it) with antiviral(s) (SOC) and/or with additional polypeptide(s) or vector(s) encoding such additional polypeptide(s). Such a combination can be in the form of (a) a mixture (e.g. mixture of two or more polypeptides or vectors), (b) a fusion between the two or more entities or (c) through specific expression design (e.g. bicistronic or independent expression). For example, the two or more entities may be expressed independently in the same vector using distinct regulatory elements (e.g. distinct promoter and termination sequences). The independent expression design is particularly adapted for expression from plasmid or measle vectors. Alternatively, the two or more entities may be expressed in a bicistronic manner under the control of the same promoter and termination sequences but requiring the use of additional regulatory elements such as IRES (for internal ribosome entry site) permitting translation of two or more cistrons from the same mRNA. A large choice of IRES is available in the art such as those originating from the poliovirus, hepatitis C virus and encephalomyocarditis (EMCV) viruses (e.g. see WO95/24485). The bicistronic design is particularly adapted for expression from vectors with more limited cloning capacity such as adenovirus vector.

The term "fusion" or "fusion protein" as used herein refers to the combination with two or more polypeptides/peptides in a single polypeptide chain. Preferably, the fusion is performed by genetic means, i.e. by fusing in frame the nucleotide sequences encoding each of said polypeptides/peptides. By "fused in frame", it is meant that the expression of the fused coding sequences results in a single protein without any translational terminator between each of the fused polypeptides/peptides. The fusion can be direct (i.e. without any additional amino acid residues in between) or through a linker (e.g. 3 to 30 amino acids long peptide composed of repeats of amino acid residues such as glycine, serine, threonine, asparagine, alanine and/or proline).

Additional polypeptide(s) or peptide(s) for use in combination with the mutant polymerase polypeptide of the invention is/are preferably a polypeptide or peptide encoded by an HBV genome, such as any native HBV polypeptide(s), modified derivative(s) and/or fragment(s) thereof. Representative examples of such HBV polypeptides or peptides include without limitation HBc (core), HBs, X protein and any immunogenic fragment thereof.

In accordance with the invention, as mentioned above, any of the additional HBV polypeptide(s) or peptide(s) in use in the invention can originate from different or from the same HBV genotype, strain or isolate as the HBV genotype, strain or isolate from which originates the mutant polymerase polypeptide of the invention. Preferably, such additional HBV polypeptide(s) originate(s) from a genotype D HBV, and especially from the Y07587 isolate.

A preferred combination is in the form of a fusion protein between the mutant polymerase polypeptide described herein and the additional polypeptide(s). Such a fusion is preferably direct without any linker between the fused entities.

Combination with Core

As used herein, the term "core polypeptide" refers to a polypeptide that retains at least 100 amino acid residues comprised in a native HBV core (HBc) protein. This term encompasses native (i.e. naturally-occurring) core polypeptides of any HBV strain, isolate or genotype that can be found, isolated, obtained from a source of HBV in nature such as those cited above in connection with the term "HBV" as well as modified core and fragments thereof.

The HBV core polypeptide in use in the invention can originate from an HBV virus having the same as or a different genotype than the one from which originates the mutant polymerase polypeptide. Preferably, they both originate from a genotype D virus and more particularly from the Y07587 isolate. Core polypeptides and their encoding sequences can be generated by a number of ways known to those skilled in the art, such as by chemical synthesis of the encoding sequence (e.g. resulting in a synthetic nucleic acid molecule) or by recombinant means (e.g. site-directed mutagenesis of the corresponding nucleotide sequence, PCR mutagenesis, DNA shuffling).

Any modification(s) can be envisaged, provided that the resulting core retains a significant immunogenic activity when combined or fused with the mutant polymerase polypeptide described herein, preferably in the same range as or higher than the native core counterpart.

Suitable modifications include truncation of at least 10 amino acid residues and at most 41 amino acid residues normally present at the C-terminus of a native core polypeptide or within the C-terminal part thereof, with a special preference for a truncation extending from residue 143, 144, 145, 146, 147, 148 or residue 149 to the C-terminus (residue 183) of the native core polypeptide. Other suitable modifications include internal deletion of one or more amino acid residues, especially in the surface-exposed region(s) such as the region located in the vicinity of residue 80 that is predicted to form an outer loop (Argos et al. 1988, EMBO J. 7: 819; Borisova et al., 1993, J. Virol. 67: 3696; Schodel et al., 1992, J. Virol. 66: 106; Yon et al., 1992, J. Gen Virol. 73: 2569; and Pumpens et al., 1995, Intervirology 38: 63).

In a preferred embodiment, the combination is in the form of a fusion. Accordingly, the invention relates to a fusion protein comprising the mutant polymerase polypeptide described herein and a fusion partner. Preferably, the fusion partner is an HBV core polypeptide, with a specific preference for a core polypeptide which is C-terminally truncated and especially truncated at residue 148.

Preferably, the HBV core polypeptide is fused in frame to the N-terminus of the mutant polymerase polypeptide described herein, resulting in a fusion protein starting with an initiator Met, the core polypeptide (modified or native) without any stop codon, the mutant polymerase polypeptide (without any Met initiator) and a stop codon.

A preferred fusion protein comprises, alternatively essentially consists of, or alternatively consists of an amino acid sequence which exhibits at least 80% of identity, advantageously at least 85% of identity, preferably at least 90% of identity, more preferably at least 95% of identity, and even more preferably 100% identity with the amino acid sequence shown in SEQ ID NO: 6. More preferably, the fusion protein of the invention comprises the amino acid sequence shown in SEQ ID NO: 6.

Combination with Immunogenic HbsAg Domains

Alternatively or in combination with the previous embodiment (combination with a core polypeptide), the mutant polymerase polypeptide of the invention can be used in combination with an HbsAg or immunogenic fragment(s)/domain(s) thereof.

As used herein, the term "immunogenic domain" refers to a polypeptide having from approximately 15 to approximately 100 amino acid residues, and preferably at least 20 and at most 60 consecutive amino acids comprising at least one B and/or T cell epitope specific for T helper ($T_H$) cells and/or for cytotoxic T (CTL) cells normally present in a native HBsAg protein. Moreover such epitope(s) can be restricted to various MHC class I and/or class II antigens (e.g. A2, A24, DR, DP, etc). Preferably, the one or more HBsAg immunogenic domains used in the invention do not include any portions of HBV preS1 and preS2 polypeptides.

Each of the one or more immunogenic domain(s) can independently originate from the same or different HBV virus(es) which can be the same or different with respect to HBV virus from which originates the mutant polymerase polypeptide described herein (and eventually the core polypeptide). Preferably, the one or more immunogenic domains originate from a genotype D HBV, and especially from the Y07587 isolate.

Exemplary immunogenic domains that can be used in the invention are described in the art (e.g. WO93/03764; WO94/19011; Desombere et al., 2000, Clin. Exp. Immunol 122: 390; Loirat et al., 2000, J. Immunol. 165: 4748; Schirmbeck et al., 2002, J. Immunol 168: 6253; Depla et al., 2008, J. Virol. 82: 435 and WO2011/015656). Particularly preferred immunogenic domains include the env1 and env2 domains described in WO2011/015656. "Env1" corresponds to the portion of a native HBsAg from approximately position 14 to approximately position 51 and env2 to the HBsAg portion from approximately position 165 to approximately position 194.

In a preferred embodiment, the combination is in the form of a fusion and the invention relates to a fusion protein comprising the mutant polymerase polypeptide described herein and one or more HBsAg immunogenic domain(s) or to the fusion protein defined above (comprising at least the mutant polymerase polypeptide described herein and an Hbc polypeptide) further comprising one or more HBsAg immunogenic domain(s). The one or more immunogenic domains can be positioned in the fusion protein at the N-terminus, at the C-terminus and/or internally, e.g. within the mutant polymerase polypeptide (for example in place of the portion lacking in the mutated polymerase and/or RNaseH domains) or in between the core and the mutant polymerase polypeptide. It is within the reach of the skilled person to define accordingly the need and location of the translation-mediating regulatory elements (e.g. the initiator Met and codon STOP at the N- and C-termini of the fusion protein).

Fusion proteins of particular interest comprise the mutant polymerase polypeptide described herein, the core polypeptide and two HBsAg immunogenic domains, with a specific preference for a fusion comprising at its N-terminus a core polypeptide (e.g. native 183 residues or truncated with 148 residues with an initiator Met) fused to the mutant polymerase polypeptide (without initiator Met) comprising one or two HbsAg immunogenic domains fused in place of the internal deletion in the mutated polymerase domain (e.g. env1) and/or in place of the deletion in the mutated RNaseH domain (e.g. env2).

In a preferred aspect of this embodiment, the fusion protein of the invention comprises, alternatively essentially consists of, or alternatively consists of an amino acid sequence which exhibits at least 80% of identity, advantageously at least 85% of identity, preferably at least 90% of identity, more preferably at least 95% of identity, and even more preferably 100% identity with any of the amino acid sequence shown in SEQ ID NO: 7-9. A particularly preferred embodiment is directed to a fusion protein comprising the amino acid sequence shown in SEQ ID NO: 8.

In the context of the invention, the mutant polymerase polypeptide of the invention or the fusion protein of the invention may further comprise additional structural features.

In one embodiment, it can comprise additional compound(s) (e.g. peptide or polypeptide) aimed to improve its immunogenic activity in a host organism. Such compounds capable of enhancing immunogenicity have been described in the literature and include, without limitation, calreticulin (Cheng et al., 2001, J. Clin. Invest. 108: 669), *Mycobacterium tuberculosis* heat shock protein 70 (HSP70) (Chen et al., 2000, Cancer Res. 60: 1035), ubiquitin (Rodriguez et al., 1997, J. Virol. 71: 8497), bacterial toxin such as the translocation domain of *Pseudomonas aeruginosa* exotoxin A (ETA(dIII)) (Hung et al., 2001 Cancer Res. 61: 3698) as well as T helper epitope(s) such as Pan-Dr peptide (Sidney et al., 1994, Immunity 1: 751), pstS1 GCG epitope (Vordermeier et al., 1992, Eur. J. Immunol. 22: 2631), tetanus toxoid peptides P2TT (Panina-Bordignon et al., 1989, Eur. J. Immunol. 19: 2237) and P30TT (Demotz et al., 1993, Eur. J. Immunol. 23: 425), influenza epitope (Lamb et al., 1982, Nature 300: 66) and hemaglutinin epitope (Rothbard et al., 1989, Int. Immunol. 1: 479).

Other suitable structural features are those which are beneficial to the synthesis, processing, stability and solubility of the mutant polymerase polypeptide or fusion protein of the invention (e.g. those aimed to modify potential cleavage sites, potential glycosylation sites and/or membrane anchorage so as to improve presentation to the cell membrane).

It could be beneficial for immune response to direct the synthesis of the mutant polymerase polypeptide or fusion protein described herein at the cell surface by using appropriate sequences well known in the art such as signal and/or trans-membrane peptides. Briefly, signal peptides are generally present at the N-terminus of membrane-presented or secreted polypeptides and initiate their passage into the endoplasmic reticulum (ER). They usually comprise 15 to 35 essentially hydrophobic amino acids which are then removed by a specific ER-located endopeptidase to give the mature polypeptide. Trans-membrane peptides are also highly hydrophobic in nature and serve to anchor the polypeptides within cell membrane. The choice of the trans-membrane and/or signal peptides which can be used in the context of the present invention is vast. They may be obtained from any membrane-anchored and/or secreted polypeptide (e.g. cellular or viral polypeptides) such as those of immunoglobulins, tissue plasminogen activator, insulin, rabies glycoprotein, the HIV virus envelope glycoprotein or the measles virus F protein or may be synthetic.

In one embodiment, the mutant polymerase polypeptide or fusion protein of the invention is fused in frame to a signal peptide which is inserted at the N-terminus downstream of the codon for initiation of translation. In another embodiment, the mutant polymerase polypeptide or fusion protein of the invention is fused in frame to a signal peptide (e.g. inserted at its N-terminus) and to a trans-membrane peptide (e.g. inserted at the C-terminus, for example immediately upstream of the stop codon). Preferably, the signal and trans-membrane peptides employed in the context of the invention originate from the rabies glycoprotein (see e.g; WO99/03885 or WO2008/138649). Preferred embodiments are directed to a HBV polymerase mutant polypeptide and a fusion protein comprising, alternatively essentially consist of, or alternatively consists of an amino acid sequence which exhibits at least 80% of identity, advantageously at least 85% of identity, particularly at least 90% of identity, preferably at least 95% of identity and more preferably 100% identity with the amino acid sequence shown in SEQ ID NO: 10, SEQ ID NO: 11 or SEQ ID NO: 12.

Nucleic Acid Molecule

In another aspect, the present invention provides isolated nucleic acid molecules encoding mutant polymerase polypeptides and fusion proteins described herein.

Within the context of the present invention, the terms "nucleic acid", "nucleic acid molecule", "polynucleotide" and "nucleotide sequence" are used interchangeably and define a polymer of any length of either polydeoxyribonucleotides (DNA) (e.g., cDNA, genomic DNA, plasmids, vectors, viral genomes, isolated DNA, probes, primers and any mixture thereof) or polyribonucleotides (RNA) (e.g., mRNA, antisense RNA) or mixed polyribo-polydeoxyribonucleotides. They encompass single or double-stranded, linear or circular, natural or synthetic polynucleotides. Moreover, a polynucleotide may comprise non-naturally occurring nucleotides and may be interrupted by non-nucleotide components.

The nucleic acid molecules of the present invention can be generated from any source using sequence data accessible in the art and the sequence information provided herein. For example, the DNA sequence coding for the HBV polymerase and if needed core polypeptide and HBsAg immunogenic domains can be isolated independently from HBV-containing cells, cDNA and genomic libraries, viral genomes or any prior art vector known to include it, and then suitably linked together by conventional molecular biology or PCR techniques. Alternatively, the nucleic acid molecules of the invention can also be generated by chemical synthesis in automatized process (e.g. assembled from overlapping synthetic oligonucleotides or synthetic gene). Modification(s) can be generated by a number of ways known to those skilled in the art, such as chemical synthesis, site-directed mutagenesis, PCR mutagenesis, DNA shuffling, etc.

Of particular interest is any of a nucleic acid molecule selected from the group consisting of:

A nucleic acid molecule which encodes a mutant polymerase polypeptide comprising a polymerase domain having the amino acid sequence shown in SEQ ID NO: 1 or 2;

A nucleic acid molecule which encodes a mutant polymerase polypeptide comprising a RNaseH domain having the amino acid sequence shown in SEQ ID NO: 3 or 4;

A nucleic acid molecule which encodes a mutant polymerase polypeptide comprising an amino acid sequence which exhibits at least 80% of identity (e.g. 80%, 85%, 90%, 95%, 97%, 100%) with the amino acid sequence shown in SEQ ID NO: 5; or A nucleic acid molecule which encodes a fusion protein comprising an amino acid sequence which exhibits at least 80% of identity (e.g. 80%, 85%, 90%, 95%, 97%, 100%) with the amino acid sequence shown in any of SEQ ID NO: 6-12.

The present invention is not limited to these exemplary nucleotide sequences and encompasses any modifications aimed to improve cloning, expression, stability of the nucleic acid molecules in use in the invention (e.g. introduction of appropriate restriction sites degeneration and/or optimisation of nucleotide sequence to optimize translation in a given host cell and/or suppression of potentially negative elements that may destabilize the nucleic acid molecule or its transcript). When several modifications are contemplated, they can concern consecutive residues and/or non-consecutive residues. The modification(s) contemplated by the present invention encompass silent modifications that do not change the amino acid sequence of the encoded polypeptides and fusion proteins, as well as modifications that are translated into the encoded polypeptides and fusion proteins.

In one embodiment, the nucleic acid molecule of the invention can be degenerated over the full length nucleotide sequence or portion(s) thereof so as to reduce sequence homology between nucleic acid molecule(s) used in the context of the invention or in the host cell. It is indeed advisable to degenerate the portions of nucleic acid sequences that show a high degree of nucleotide sequence identity and the skilled person is capable of identifying such portions by sequence alignment. For example if a vector carries a nucleic acid molecule encoding a mutant polymerase polypeptide as described herein and a nucleic acid molecule encoding another HBV polypeptide encoded by overlapping sequences in the HBV genome, it may be advantageous to degenerate one or both nucleic acid molecule(s) in the overlapping portions so as to avoid homologous recombination problems during production process.

Alternatively or in combination, the nucleic acid molecule of the invention can be optimized for providing high level expression in a particular host cell or organism. It has been indeed observed that, when more than one codon is available to code for a given amino acid, the codon usage patterns of organisms are highly non-random and the utilisation of codons may be markedly different between different hosts. As the nucleotide sequences encompassed by the invention are mostly of viral origin (HBV), they may have an inappropriate codon usage pattern for efficient expression in host cells such as bacterial, lower or higher eukaryotic cells. Typically, codon optimisation can be performed by replacing one or more "native" (e.g. HBV) codon corresponding to a codon infrequently used in the host cell/organism of interest by one or more codon encoding the same amino acid which is more frequently used in the host cell/organism of interest. It is not necessary to replace all native codons corresponding to infrequently used codons since increased expression can be achieved even with partial replacement. Moreover, some deviations from strict adherence to optimised codon usage may be made to accommodate the introduction of restriction site(s) into the resulting nucleic acid molecule.

Further, expression in the host cell or organism can be improved through additional modifications of the nucleotide sequence aimed to prevent clustering of rare, non-optimal codons and/or to suppress or modify at least partially negative sequence elements which are expected to negatively influence expression levels (e.g. AT-rich or GC-rich sequence stretches; unstable direct or inverted repeat sequences; RNA secondary structures; and/or internal cryptic regulatory elements such as internal TATA-boxes, chi-sites, ribosome entry sites, and/or splicing donor/acceptor sites).

A particularly preferred embodiment of the present invention is directed to a nucleic acid molecule comprising, alternatively essentially consisting of or alternatively consisting of a nucleotide sequence which exhibits at least 80% of identity, advantageously at least 85% of identity, preferably at least 90% of identity, more preferably at least 95% of identity, and even more preferably 100% identity with the nucleotide sequence shown in any of SEQ ID NO: 13 to 17.

Another embodiment of the invention pertains to fragments of the nucleic acid molecules of the invention, e.g. restriction endonuclease and PCR-generated fragments. Such fragments can be used as probes, primers or fragments encoding an immunogenic portion of the encoded immunogenic polypeptide.

Vectors

In another aspect, the present invention provides vectors comprising a nucleic acid molecule of the present invention.

The term "vector" as used herein refers to a vehicle, preferably a nucleic acid molecule or a viral particle that contains the elements necessary to allow delivery, propagation and/or expression of one or more nucleic acid molecule(s) within a host cell or organism. This term encompasses vectors for maintenance (cloning vectors) or vectors for expression in various host cells or organisms (expression vectors), extrachromosomal vectors (e.g. multicopy plasmids) or integration vectors (e.g. designed to integrate into the host cell genome and produce additional copies of the nucleic acid molecules when the host cell replicates) as well as shuttle vectors (e.g. functioning in both prokaryotic and/or eukaryotic hosts) and transfer vectors (e.g. for transferring nucleic acid molecule(s) in a viral genome). For the purpose of the invention, the vectors may be of naturally occurring genetic sources, synthetic or artificial, or some combination of natural and artificial genetic elements.

In the context of the invention, the term "vector" has to be understood broadly as including plasmid and viral vectors. A "plasmid vector" as used herein refers to a replicable DNA construct. Usually plasmid vectors contain selectable marker genes that allow host cells carrying the plasmid vector to be selected for or against in the presence of a corresponding selective drug. A variety of positive and negative selectable marker genes are known in the art. By way of illustration, an antibiotic resistance gene can be used as a positive selectable marker gene that allows a host cell to be selected in the presence of the corresponding antibiotic.

The term "viral vector" as used herein refers to a nucleic acid vector that includes at least one element of a virus genome and may be packaged into a viral particle or to a viral particle. The terms "virus", "virions", viral particles" and "viral vector particle" are used interchangeably to refer to viral particles that are formed when the nucleic acid vector is transduced into an appropriate cell or cell line according to suitable conditions allowing the generation of infectious viral particles. In the context of the present invention, the term "viral vector" has to be understood broadly as including nucleic acid vector (e.g. DNA viral vector) as well as viral particles generated thereof. The term "infectious" refers to the ability of a viral vector to infect and enter into a host cell or organism. Viral vectors can be replication-competent or -selective (e.g. engineered to replicate better or selectively in specific host cells), or can be genetically disabled so as to be replication-defective or replication-impaired.

Vectors which are appropriate in the context of the present invention, include, without limitation, bacteriophage, plasmid or cosmid vectors for expression in prokaryotic host cells such as bacteria (e.g. *E. coli, Bacillus subtilis* or *Listeria*); vectors for expression in yeast (e.g. *Saccharomyces cerevisiae, Saccharomyces pombe, Pichia pastoris*); baculovirus vectors for expression in insect cell systems (e.g. Sf 9 cells); viral and plasmid vectors for expression in plant cell systems (e.g. Ti plasmid, cauliflower mosaic virus CaMV; tobacco mosaic virus TMV); as well as viral and plasmid vectors for expression in higher eukaryotic cells or organisms.

Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them.

Representative examples of suitable plasmid vectors include, without limitation, pREP4, pCEP4 (Invitrogen), pCI (Promega), pVAX (Invitrogen) and pgWiz (Gene Therapy System Inc).

Representative examples of suitable viral vectors are generated from a variety of different viruses (e.g. retrovirus, adenovirus, adenovirus-associated virus (AAV), poxvirus, herpes virus, measle virus, foamy virus, alphavirus, vesicular stomatis virus, etc). As described above, the term "viral vector" encompasses vector DNA, genomic DNA as well as viral particles generated thereof.

The present invention also encompasses vectors (e.g. plasmid DNA) complexed to lipids or polymers to form particulate structures such as liposomes, lipoplexes or nanoparticles.

In one embodiment, the vector of the invention is an adenoviral vector. It can be derived from a variety of human or animal adenoviruses (e.g. canine, ovine, simian, etc). Any serotype can be employed. Desirably, the adenoviral vector is replication-defective and originates from a human Ad, and more particularly from a human Ad of a rare serotype, or from a chimpanzee Ad. Representative examples of human adenoviruses include subgenus C Ad2 Ad5 and Ad6, subgenus B Ad11, Ad34 and Ad35 and subgenus D Ad19, Ad24, Ad48 and Ad49. Representative examples of chimp Ad include without limitation AdCh3 (Peruzzi et al., 2009, Vaccine 27: 1293), AdCh63 (Dudareva et al., 2009, vaccine 27: 3501) and any of those described in the art (see for example WO03/000283; WO03/046124; WO2005/071093; WO2009/073103; WO2009/073104; WO2009/105084; WO2009/136977 and WO2010/086189).

Replication-defective adenoviral vectors can be obtained as described in the art, e.g by deletion of at least a region of the adenoviral genome or portion thereof essential to the viral replication, with a specific preference for deletion of E1 region comprising E1 coding sequences (e.g. extending from approximately positions 459 to 3510 by reference to the sequence of the human adenovirus type 5 disclosed in the GeneBank under the accession number M 73260 and in Chroboczek et al., 1992, Virol. 186:280). The present invention also encompasses vectors having additional deletion(s)/modification(s) within the adenoviral genome (all or part of the non-essential E3 region or of other essential E2, E4 regions as described in WO94/28152; Lusky et al., 1998, J. Virol 72: 2022).

The nucleic acid molecule of the present invention can be inserted in any location of the adenoviral genome, and may be positioned in sense or antisense orientation relative to the natural transcriptional direction of the region in question. Preferably, the nucleic acid molecule of the invention is inserted in replacement of the adenoviral E1 region and placed under the control the CMV promoter.

Other viral vectors suitable in the context of the invention are poxviral vectors which can be obtained from any member of the poxviridae with a specific preference for a poxviral vector originating from a canarypox, fowlpox or vaccinia virus, the latter being preferred. Suitable vaccinia viruses include without limitation the Copenhagen strain (Goebel et al., 1990, Virol. 179: 247; Johnson et al., 1993, Virol. 196: 381), the Wyeth strain and particularly the modified Ankara (MVA) strain (Antoine et al., 1998, Virol. 244: 365). The general conditions for constructing recombinant poxvirus are well known in the art. The nucleic acid molecule of the present invention is preferably inserted within the poxviral genome in a non-essential locus. Thymidine kinase gene is particularly appropriate for insertion in Copenhagen vaccinia vectors and deletion II or III for insertion in MVA vector. Preferably, the nucleic acid molecule of the invention is inserted in deletion III of the MVA vector and placed under the control the vaccinia 7.5K or pH5R promoter.

Other viral vectors suitable in the context of the invention are morbillivirus which can be obtained from the paramyxoviridae family, with a specific preference for measles virus. Various attenuated strains are available in the art (Brandler et al, 2008, CIMID, 31: 271; Singh et al., 1999, J. virol. 73(6): 4823), such as and without limitation, the Edmonston A and B strains (Griffin et al., 2001, Field's in Virology, 1401-1441), the Schwartz strain (Schwarz A, 1962, Am J Dis Child, 103: 216), the S-191 or C-47 strains (Zhang et al., 2009, J Med Virol. 81 (8): 1477). Insertion between P and M genes is particularly appropriate.

In accordance with the present invention, the nucleic acid molecule(s) comprised in the vector of the invention is in a form suitable for expression in a host cell or organism, which means that the nucleic acid molecule is placed under the control of appropriate regulatory sequences. As used herein, the term "regulatory elements" refers to any element that allows, contributes or modulates the expression of a nucleic acid molecule in a given host cell or organism, including replication, duplication, transcription, splicing, translation, stability and/or transport of the nucleic acid or its derivative (i.e. mRNA).

It will be appreciated by those skilled in the art that the choice of the regulatory sequences can depend on such factors as the vector itself, the host cell, the level of expression desired, etc. The promoter is of special importance. In the context of the invention, it can be constitutive directing expression of the nucleic acid molecule in many types of host cells or specific to certain host cells (e.g. liver-specific regulatory sequences) or regulated in response to specific events or exogenous factors (e.g. by temperature, nutrient additive, hormone, etc) or according to the phase of a viral cycle (e.g. late or early). One may also use promoters that are repressed during the production step in response to specific events or exogenous factors, in order to optimize vector production and circumvent potential toxicity of the expressed polypeptide(s).

Promoters suitable for constitutive expression in mammalian cells include but are not limited to the cytomegalovirus (CMV) immediate early promoter (Boshart et al., 1985, Cell 41: 521), the RSV promoter, the adenovirus major late promoter, the phosphoglycero kinase (PGK) promoter (Adra et al., 1987, Gene 60: 65), the thymidine kinase (TK) promoter of herpes simplex virus (HSV)-1 and the T7 polymerase promoter. Vaccinia virus promoters are particularly adapted for expression in poxviral vectors. Representative example include without limitation the vaccinia 7.5K, H5R, 11K7.5 (Erbs et al., 2008, Cancer Gene Ther. 15: 18), TK, p28, p11 and K1L promoter, as well as synthetic promoters such as those described in Chakrabarti et al. (1997, Biotechniques 23: 1094), Hammond et al. (1997, J. Virological Methods 66: 135) and Kumar and Boyle (1990, Virology 179: 151) as well as early/late chimeric promoters. Promoters suitable for measle-mediated expression include without limitation any promoter directing expression of measle transcription units (Brandler and Tangy, 2008, CIMID 31: 271). Liver-specific promoters include without limitation those of HMG-CoA reductase (Luskey, 1987, Mol. Cell. Biol. 7: 1881); sterol regulatory element 1 (SRE-1; Smith et al., 1990, J. Biol. Chem. 265: 2306); albumin (Pinkert et al., 1987, Genes Dev. 1: 268); phosphoenol pyruvate carboxy kinase (PEPCK) (Eisenberger et al., 1992, Mol. Cell Biol. 12: 1396); alpha-1 antitrypsin (Ciliberto et al., 1985, Cell 41: 531); human transferrin (Mendelzon et al., 1990, Nucleic Acids Res. 18: 5717); and FIX (U.S. Pat. No. 5,814,716) genes.

Those skilled in the art will appreciate that the regulatory elements controlling the expression of the nucleic acid molecule of the invention may further comprise additional elements for proper initiation, regulation and/or termination of transcription (e.g. polyA transcription termination sequences), mRNA transport (e.g. nuclear localization signal sequences), processing (e.g. splicing signals), and stability (e.g. introns and non-coding 5' and 3' sequences), translation (e.g. an initiator Met, tripartite leader sequences, IRES ribosome binding sites, Shine-Dalgarno sequences, etc.) into the host cell or organism and purification steps (e.g. a tag).

Particularly preferred embodiments of the invention are directed to vectors (or viral particles) selected from the group consisting of:

A defective Ad vector comprising inserted in place of the E1 region a nucleic acid molecule placed under the control of a promoter such as the CMV promoter, and encoding a mutant polymerase polypeptide comprising an amino acid sequence as shown in SEQ ID NO: 5 or a fusion protein comprising an amino acid sequence as shown in SEQ ID NO: 6 or SEQ ID NO: 8;

A defective Ad vector comprising inserted in place of the E1 region a nucleic acid molecule placed under the control of a promoter such as the CMV promoter, and comprising the nucleotide sequence shown in SEQ ID NO: 13, SEQ ID NO: 14 or SEQ ID NO: 15;

A replication-defective Ad vector especially a defective AdCh3 comprising inserted in place of the E1 region a nucleic acid molecule placed under the control of a promoter such as the CMV promoter and comprising the nucleotide sequence shown in SEQ ID NO: 16 or SEQ ID NO: 17;

A MVA vector comprising a nucleic acid molecule placed under the control of a vaccinia promoter such as the 7.5K or pH5R promoter, and encoding a mutant polymerase polypeptide comprising the amino acid sequence shown in SEQ ID NO: 5 or SEQ ID NO: 10 or a fusion protein comprising the amino acid sequence shown in SEQ ID NO: 6, SEQ ID NO: 8 or SEQ ID NO: 12; and A MVA vector comprising a nucleic acid molecule placed under the control of a vaccinia promoter such as the 7.5K or pH5R promoter, and comprising the nucleotide sequence shown in SEQ ID NO: 13, SEQ ID NO: 14 or SEQ ID NO: 15. Preferably, said nucleic acid molecule is inserted in deletion III of the MVA genome.

If needed, the vector of the invention can further comprise one or more transgene(s), e.g. a gene of interest to be expressed together with the nucleic acid molecule of the invention in a host cell or organism aimed to improve therapeutic or protective activity to an HBV infection or any disease or condition caused by or associated with an HBV infection. Suitable transgenes include without limitation immunomodulators such as cytokines and any other antigen originating from a potentially co-infecting organism (e.g. HIV, tuberculosis mycobacterium, etc). If a transgene is used, it can be expressed from the vector of the invention or from an independent vector for use in combination which can be the same or different with respect to the vector of the invention. For example, one may envisage using in combination an adenovirus expressing the mutant polymerase polypeptide or the fusion protein of the invention and an adenovirus expressing an immunomodulator.

According to a preferred embodiment, the vector of the invention is in the form of infectious viral particles. Typically, such viral particles are produced by a process comprising the steps of (a) introducing the viral vector of the invention into a suitable cell line, (b) culturing said cell line under suitable conditions so as to allow the production of said infectious viral particle, (c) recovering the produced viral particle from the culture of said cell line, and (d) optionally purifying said recovered viral particle.

When the viral vector is defective, the particles are usually produced in a complementation cell line or via the use of a helper virus, which supplies in trans the non-functional viral genes. For example, suitable cell lines for complementing E1-deleted adenoviral vectors include the 293 cells (Graham et al., 1997, J. Gen. Virol. 36: 59-72) as well as the HER-96 and PER-C6 cells (e.g. Fallaux et al., 1998, Human Gene Ther. 9: 1909-1917; WO97/00326) or any derivative of these cell lines. But any other cell line described in the art can also be used in the context of the present invention, especially any cell line used for producing product for human use such as Vero cells, HeLa cells and avian cells particularly suitable for propagating poxvirus vectors Suitable avian cells include without limitation primary chicken embryo fibroblasts (CEF) prepared from chicken embryos obtained from fertilized eggs, and duck cell lines (e.g. as described in WO03/076601, WO2009/004016, WO2010/130756 and US2011-008872).

The infectious viral particles may be recovered from the culture supernatant and/or from the cells after lysis. They can be further purified according to standard techniques (chromatography, ultracentrifugation in a cesium chloride gradient as described for example in WO96/27677, WO98/00524, WO98/22588, WO98/26048, WO00/40702, EP1016700 and WO00/50573).

The present invention also encompasses vectors or viral particles that have been modified to allow preferential targeting to a specific host cell. A characteristic feature of targeted vectors is the presence at their surface of a ligand capable of recognizing and binding to a cellular and surface-exposed component such as a cell-specific marker (e.g. an HBV-infected cell), a tissue-specific marker (e.g. a liver-specific marker), as well as a viral (e.g. HBV) antigen. Examples of suitable ligands include antibodies or fragments thereof directed to an HBV antigenic domain. Targeting can be carried out by genetically inserting the ligand into a polypeptide present on the surface of the virus (e.g. adenoviral fiber, penton, pIX or vaccinia p14 gene product).

Host Cells

In another aspect, the invention also relates to host cells which comprise the nucleic acid molecules or vectors (or viral particles) of the invention.

As used herein, the term "host cell" should be understood broadly without any limitation concerning particular organization in tissue, organ, or isolated cells. Such cells may be of a unique type of cells or a group of different types of cells such as cultured cell lines, primary cells and proliferative cells. In the context of the invention, the term "host cells" include prokaryotic cells, lower eukaryotic cells such as yeast, and other eukaryotic cells such as insect cells, plant and mammalian (e.g. human or non-human) cells as well as cells capable of producing the vector of the invention (e.g. 293, HER96, PERC.6 cells, Vero, HeLa, CEF, duck cell lines, etc). This term includes cells which can be or has been the recipient of the vector described herein as well as progeny of such cells. Host cells can be cultured in conventional fermentation bioreactors, flasks, and petri plates. Culturing can be carried out at a temperature, pH and oxygen content appropriate for a given host cell. No attempts will be made here to describe in detail the various prokaryote and eukaryotic host cells and methods known for the production of the polypeptides and vectors in use in the invention.

According to a specific embodiment of the invention, the host cell can be further encapsulated. Cell encapsulation technology is known in the art.

Still a further aspect of the present invention is a method for recombinant production of the mutant polymerase polypeptide or the fusion protein of the invention, employing the vectors (or infectious viral particles) and/or host cells of the invention. Typically, the method comprises (a) introducing a vector into a suitable host cell to produce a transfected or infected host cell, (b) culturing in-vitro said transfected or infected host cell under conditions suitable for growth of the host cell, (c) recovering the cell culture, and (d) optionally, purifying the mutant polymerase polypeptide or the fusion protein from the recovered cell and/or culture supernatant.

It is expected that those skilled in the art are knowledgeable in the numerous expression systems available in the art for expressing the mutant polymerase polypeptide or the fusion protein in appropriate host cells (such as those described above) and of the methods for introducing a vector into a host cell. Such methods include, but are not limited to microinjection, $CaPO_4$-mediated transfection, DEAE-dextran-mediated transfection, electroporation, lipofection/liposome fusion, gene guns, transduction, viral infection as well as direct administration into a host organism via various means. The vector of the invention can be used in association with transfection reagents in order to facilitate introduction in the host cell, such as polycationic polymers (e.g.

chitosan, polymethacrylate, PEI, etc) and cationic lipids (e.g. DC-Chol/DOPE, transfectam lipofectin now available from Promega).

Host cells can be cultured in conventional fermentation bioreactors, flasks, and petri plates. Culturing can be carried out at a temperature, pH and oxygen content appropriate for a given host cell. The mutant polymerase polypeptide or the fusion protein can then be purified by well-known purification methods including ammonium sulfate precipitation, acid extraction, gel electrophoresis; filtration and chromatographic methods (e.g. reverse phase, size exclusion, ion exchange, affinity, hydrophobic-interaction, hydroxylapatite, high performance liquid chromatography, etc). The conditions and technology to be used depend on factors such as net charge, molecular weight, hydrophobicity, hydrophilicity and will be apparent to those having skill in the art. Moreover, the level of purification will depend on the intended use.

Compositions

In another aspect, this invention provides a composition comprising at least the mutant polymerase polypeptide or the fusion protein, the nucleic acid molecule, the vector (e.g. the infectious viral particle), or the host cell described herein (also referred herein to "active agent") or any combination thereof (e.g. combination of different polypeptides or vectors/viral particles as described herein or combination of different genotypes). Preferably, the composition is a pharmaceutical composition which comprises a pharmaceutically acceptable vehicle further to a therapeutically effective amount of the active agent(s).

As used herein, a "pharmaceutically acceptable vehicle" is intended to include any and all carriers, solvents, diluents, excipients, adjuvants, dispersion media, coatings, antibacterial and antifungal agents, and absorption delaying agents, and the like, compatible with administration in a host organism and in particular in human.

As used herein a "therapeutically effective amount" is a dose sufficient for the alleviation of one or more symptoms normally associated with an HBV infection or any disease or condition caused by or associated with an HBV infection. When prophylactic use is concerned, this term means a dose sufficient to prevent or to delay the establishment of an HBV infection. "Therapeutic" compositions are designed and administered to a host organism already infected by an HBV with the goal of reducing or ameliorating at least one disease or condition caused by or associated with said HBV infection, eventually in combination with one or more conventional therapeutic modalities as described herein (e.g. treatment with nucleoside, nucleotide analogs and/or IFN-based therapy). For example, a therapeutically effective amount for inducing an immune response could be that amount necessary to cause activation of the immune system (e.g. resulting in the development of an anti-HBV response).

The term "host organism" generally refers to a vertebrate, particularly a member of the mammalian species and especially domestic animals, farm animals, sport animals, and primates including humans for whom any product and method of the invention is needed or may be beneficial such as organisms who have been diagnosed as being or at risk of being infected with an HBV and thus are susceptible of having or at risk of having a disease or condition caused by or associated with an HBV infection. In preferred embodiments, the host organism is a human patient chronically infected with an HBV virus or alternatively co-infected with an HBV virus and another virus (e.g. the human immunodeficiency virus HIV). The infecting HBV can be from the same genotype, strain or isolate as any HBV from which originates the mutant polymerase polypeptide or any other HBV polypeptide/peptide in use in the present invention (e.g. genotype D) or it can be from a different genotype (e.g. genotype B or C). The cross reactive potential of a genotype D-based vaccine composition was recently investigated by the inventors (see U.S. application Ser. No. 13/423,193). A vast in silico study highlighted that the amino acid sequences of HBV polymerase, core and Env proteins are highly conserved among genotypes B, C and D at the global protein level but also at the T cell epitope level. In vivo immunization in a suitable animal model supported the ability to induce cross reactive T cell responses recognizing genotype B and C epitopes. Even if this study is limited to HLA-A2 epitopes, it provides a proof of concept that a vaccine composition based on genotype D antigens is able to induce T cell responses that are cross reactive with other HBV genotypes.

The composition of the invention is suitably buffered in order to be appropriate for human use at a physiological or slightly basic pH (e.g. from approximately pH 7 to approximately pH 9). Suitable buffers include without limitation phosphate buffer (e.g. PBS), bicarbonate buffer and/or Tris buffer.

The composition of the invention can further comprise a diluent appropriate for human or animal use. It is preferably isotonic, hypotonic or weakly hypertonic and has a relatively low ionic strength. Representative examples include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins).

The pharmaceutically acceptable vehicles included in the composition of the invention must also permit to preserve its stability under the conditions of manufacture and long-term storage (i.e. at least one month with a preference for at least one year) at freezing (e.g. −70° C., −20° C.), refrigerated (e.g. 4° C.) or ambient temperatures. In this respect, formulations which are particularly adapted to the composition of the invention include (a) 1M saccharose, 150 mM NaCl, 1 mM $MgCl_2$, 54 mg/l Tween 80, 10 mM Tris pH 8.5 (especially when the active agent is an adenoviral vector), (b) 10 mg/ml mannitol, 1 mg/ml HSA, 20 mM Tris, pH 7.2, and 150 mM NaCl and (c) physiological saline.

Additional pharmaceutically acceptable excipients may be used for providing desirable pharmaceutical or pharmacodynamic properties, including for example modifying or maintaining the pH, osmolarity, viscosity, clarity, colour, sterility, stability, rate of dissolution of the formulation, modifying or maintaining release or absorption into an the human or animal organism, promoting transport across the blood barrier or penetration in a particular organ (e.g. liver).

In addition, the composition of the invention may comprise one or more adjuvant(s) suitable for systemic or mucosal application in humans. Preferably, the adjuvant is capable of stimulating immunity to the composition of the invention, especially a T cell-mediated immunity e.g. through the toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p407-419), saponins such as QS21 (Sumino et al., 1998, J. Virol. 72: 4931; WO 98/56415), imidazo-quinoline compounds such as Imiquimod (Suader, 2000, J. Am Acad Dermatol. 43: S6), S-27609 (Smorlesi, 2005, Gene Ther. 12: 1324) and related compounds such as those described in WO2007/147529, cytosine phosphate guanosine oligodeoxynucleotides such as CpG (Chu et al., 1997, J. Exp. Med. 186: 1623; Tritel et al., 2003, J. Immunol. 171: 2358) and cationic peptides such as IC-31 (Kritsch et al., 2005, J. Chromatogr Anal. Technol Biomed Life Sci 822: 263).

The composition of the present invention is suitable for a variety of modes of administration.

The term "administration" (and any form of administration such as "administered") as used herein refers to the delivery of a therapeutic agent such as the mutant polymerase polypeptide, the fusion protein, the nucleic acid molecule, the vector described herein into a host cell or organism. A number of methods and means are available in the art such as direct administration to a host organism.

Direct administration can be performed by systemic, topical or mucosal routes Systemic administration includes for example subcutaneous, intradermal, intramuscular, intravenous (e.g. injection into a vein feeding liver such as the portal vein), intraperitoneal, intratumoral, intravascular, intraarterial injection (e.g. by hepatic artery infusion) as well as scarification. Injections can be made with conventional syringes and needles, or any other appropriate devices available in the art (e.g. electroporation). Alternatively the composition of the present invention may be administered via a mucosal route, such as the oral/alimentary, intranasal, intratracheal, intrapulmonary, intravaginal or intra-rectal route. Administration in the respiratory tract can be performed through nebulisation or aerosolization of droplet, spray, or dry powdered compositions using appropriate dispenser. Topical administration can also be performed using transdermal means (e.g. patch and the like).

In the context of the invention, the composition is preferably formulated for intramuscular, subcutaneous, intradermal administration or scarification.

The composition of the invention can be in various forms, e.g. solid, liquid or frozen. Solid (e.g. dry powdered or lyophilized) compositions can be obtained by a process involving vacuum drying and freeze-drying. For mucosal administration, the compositions can be formulated as gastroresistant capsules and granules for oral administration, suppositories for rectal or vaginal administration, eventually in combination with absorption enhancers useful to increase the pore size of the mucosal membranes. Such absorption enhancers are typically substances having structural similarities to the phospholipid domains of the mucosal membranes such as sodium deoxycholate, sodium glycocholate, dimethyl-beta-cyclodextrin, lauryl-1-lysophosphatidylcholine).

The appropriate dosage can be adapted as a function of various parameters, in particular the mode of administration; the composition employed; the age, health, and weight of the host organism; the nature and extent of symptoms; kind of concurrent treatment; the frequency of treatment; and/or the need for prevention or therapy. Further refinement of the calculations necessary to determine the appropriate dosage for treatment is routinely made by a practitioner, in the light of the relevant circumstances.

For general guidance, suitable dosage for a vector-comprising composition varies from about $10^5$ to about $10^{13}$ vp (viral particles), iu (infectious unit) or pfu (plaque-forming units) depending on the vector and the quantitative technique used. Techniques available to evaluate the quantity of vp, iu and pfu present in a sample are conventional in the art. For example, the number of adenoviral particles (vp) is usually determined by measuring the A260 absorbance or HPLC, iu titers by quantitative DBP immunofuorescence and pfu by counting the number of plaques following infection of permissive cells. Preferably the vp/iu ratio is below 100 in accordance with FDA guidelines. Preferred doses contain from about $10^5$ to about $10^{12}$ vp, with a specific preference for doses of about $5\times10^8$, about $10^9$, about $5\times10^9$, about $10^{10}$, about $5\times10^{10}$ vp or about $10^{11}$ vp of an adenoviral vector of the invention. Doses from about $5\times10^5$ to about $10^9$ pfu are preferred for vaccinia (MVA)-based composition with a specific preference for doses of about $5\times10^6$, about $10^7$, about $5\times10^7$, about $10^8$ or about $5\times10^8$ pfu. A composition based on vector plasmids may be administered in doses of between 10 μg and 20 mg, advantageously between 100 μg and 2 mg. A protein composition may be administered in one or more doses of between 10 ng and 20 mg, with a special preference for a dosage from about 0.1 μg to about 2 mg of the immunogenic polypeptide per kg body weight. The administration may take place in a single dose or a dose repeated one or several times after a certain time interval.

In another specific embodiment, the mutant polymerase polypeptide, fusion protein, nucleic acid molecule, vector, host cell or composition of the invention can be used in combination with additional polypeptides or peptides or vector encoding such additional polypeptides or peptides. Preferably, said additional polypeptide or peptide is a HBV antigen with a specific preference for an Hbc polypeptide and/or one or more HBs immunogenic domains as described herein. The HBV polypeptide or peptide can be expressed from a vector, in particular a vector selected from the group consisting of plasmid DNA, adenoviral (e.g. Ad5, AdCh3, AdCh63, etc), poxviral (e.g. vaccinia such as MVA) and measle vectors. Accordingly the invention also relates to a composition comprising a mixture of a vector encoding a mutant polymerase polypeptide or a fusion protein of the invention and a vector encoding at least one additional polypeptide/peptide such as an HBV core and/or HBs immunogenic domain(s) as described herein.

The mutant polymerase polypeptide, fusion protein, nucleic acid molecule, vector, host cell or composition of the invention may be employed in methods for treating a variety of diseases and pathologic conditions, especially those caused by or associated with an HBV infection. Accordingly, the present invention also encompasses the mutant polymerase polypeptide, fusion protein, nucleic acid molecule, vector, host cell or composition of the invention for use for treating or preventing HBV infections, HBV-associated diseases and pathologic conditions, according to the modalities described herein, and particularly chronic HBV infection. The present invention also relates to a method of treatment in an organism in need thereof comprising at least one administration to said organism of at least one of such active agents in an amount sufficient to treat or prevent HBV infections (e.g. particularly chronic HBV infection) or alleviate one or more symptoms related to HBV-associated diseases and pathologic conditions, according to the modalities described herein. In a particular embodiment, the active agent(s) and method(s) of the invention may be employed according to the modalities described herein to break HBV-specific immune tolerance usually encountered in HBV chronic subjects.

The term "treating" (and any form of treating such as "treatment") as used herein refers to prophylaxis (e.g. prevention of a subject at risk of being infected with HBV) and/or therapy (e.g. in a subject diagnosed as being infected with an HBV). It is especially useful for treating HBV chronic infection and/or liver lesions in HBV-infected patients including cirrhosis and liver cancer. Treatment requires administer externally or internally to a host cell or organism a therapeutic agent such as the mutant polymerase polypeptide described herein, eventually in combination with other HBV polypeptide(s) or with the standard of care (SOC) (e.g. treatment with nucleoside or nucleotide analogs).

Typically, upon administration into a host organism according to the modalities described herein, the mutant polymerase polypeptide, fusion protein, nucleic acid molecule, vector, host cell and/or composition of the invention provides a therapeutic benefit to the treated host organism over the baseline status or over the expected status if not treated. The therapeutic benefit can be evidenced by any relevant clinical measurement typically used by physicians or other skilled healthcare staff, including, for instance, a decrease of the HBV viral load quantified in blood, plasma, or sera of a treated organism, and/or a decrease of the level of liver enzyme activity (e.g. alanine aminotransferase (ALT) and/or aspartate aminotransferase (AST)), and/or a stabilized (not worsening) state of disease (e.g. stabilization or decrease of conditions typically associated with HBV infection such as liver inflammation/steatosis/fibrosis), and/or the reduction of the level of sero markers such as HBeAg or HBsAg (e.g. HBe or HBs seroconversion) and/or an improved response of the treated organism to conventional therapies and/or a survival extension as compared to expected survival if not receiving treatment.

In the context of the invention, the therapeutic benefit can be transient (for one or a couple of months after cessation of administration) or sustained (for several months or years). As the natural course of clinical status which may vary considerably from a subject to another, it is not required that the therapeutic benefit be observed in each organism treated but in a significant number of organisms (e.g. statistically significant differences between two groups can be determined by any statistical test known in the art, such as a Tukey parametric test, the Kruskal-Wallis test the U test according to Mann and Whitney, the Student's t-test, the Wilcoxon test, etc).

Such measurements can be performed before the administration of the described herein (baseline) and at various time points during treatment and at least for 12 weeks after cessation of the treatment. For general guidance, the viral load can be determined using a quantitative PCR assay or any other methodology accepted in the art (e.g. Roche Ampli Prep/Cobas taqman assay v2.0, Abbott real-time hepatitis B virus performance assay). In preferred embodiments, the administration of the mutant polymerase polypeptide, fusion protein, nucleic acid molecule, vector, host cell and/or composition of the invention results in a reduction of the viral load whether transient or sustained of at least one $\log_{10}$, preferably at least 1.5 $\log_{10}$ and more preferably at least 2 $\log_{10}$ as compared to the viral load measured at baseline or as compared to the control group (non-treated subjects). The administration of the active agent(s) described herein can result in a at least transient return to normal ALT and/or AST values as compared to baseline or to the control group. The levels of liver enzyme activity can be evaluated routinely in medical laboratories and hospitals. Alternatively, the administration of the active agent(s) described herein results in a at least transient reduction of seromarker HBe and/or HBs of at least one $\log_{10}$, preferably at least 1.5 $\log_{10}$ and more preferably at least 2 $\log_{10}$ as compared to the seromarker level measured at baseline or as compared to the control group (non-treated subjects). The levels of HBV seromarker can be evaluated routinely in medical laboratories and hospitals and a large number of kits are available commercially (e.g. immunoassays developed by Abbott Laboratories, Organon Technika).

Preferably, the mutant polymerase polypeptide, fusion protein, nucleic acid molecule, vector, host cell and/or composition of the invention are/is used or administered for eliciting or stimulating an immune response in the treated organism. Accordingly, the present invention also encompasses a method for eliciting or stimulating an immune response against HBV upon administration in a host organism of the mutant polymerase polypeptide, fusion protein, nucleic acid molecule, vector, host cell and/or composition of the invention.

The elicited or stimulated immune response can be specific (i.e. directed to HBV epitopes/antigen) and/or non-specific (innate), humoral and/or cellular. In the context of the invention, the immune response is preferably a T cell response CD4+ or CD8+-mediated or both, directed to an HBV polypeptide/epitope.

The ability of the active agents(s) described herein to elicit an immune response can be evaluated either in vitro or in vivo using a variety of direct or indirect assays which are standard in the art. Testing and validation are also illustrated in the appended Example section.

For a general description of techniques available to evaluate the onset and activation of an immune response, see for example Coligan et al. (1992 and 1994, Current Protocols in Immunology; ed J Wiley & Sons Inc, National Institute of Health or subsequent editions). The ability to stimulate a humoral response may be determined by antibody binding and/or competition in binding (see for example Harlow, 1989, Antibodies, Cold Spring Harbor Press).

Evaluation of non-specific immunity can be performed by for example measurement of the NK/NKT-cells (e.g. representativity and level of activation), as well as, IFN-related cytokine and/or chemokine producing cascades, activation of TLRs and other markers of innate immunity (Scott-Algara et al., 2010 PLOS One 5(1), e8761; Zhou et al., 2006, Blood 107, 2461-2469; Chan, 2008, Eur. J. Immunol. 38, 2964-2968).

Evaluation of cellular immunity can be performed for example by quantification of cytokine(s) produced by activated T cells including those derived from CD4+ and CD8+ T-cells using routine bioassays (e.g. characterization and/or quantification of T cells by ELISpot, by multiparameters flow cytometry or ICS, by cytokine profile analysis using multiplex technologies or ELISA), by determination of the proliferative capacity of T cells (e.g. T cell proliferation assays by [$^3$H] thymidine incorporation assay), by assaying cytotoxic capacity for antigen-specific T lymphocytes in a sensitized subject or by immunization of appropriate animal models.

The immunogenic capacity of the mutant polymerase polypeptide, fusion protein, nucleic acid molecule, vector, host cell and/or composition of the invention can also be further validated in animal models, which can be challenged with an appropriate infectious or tumor-inducing agent (e.g. a vaccinia virus or a *Listeria monocytogenes* bacteria expressing HBV gene products) or injected by a DNA encoding the full-length HBV genome (such as described in Huan et al., 2010, Proc. Natl. Acad. Sci. 107: 9340 to determine neutralization of the infectious or tumor-inducing agent and eventually partial resistance to the associated symptoms, reflecting an induction or an enhancement of an anti-HBV immune response. Exemplary animal models include without limitation the HLA-A2.1 transgenic mice described in Examples, and HBV transgenic mice such as those described in Chisari et al. (1996, Curr. Top. Microbiol. Immunol., 206: 149) and Halverscheid al. (2008, J. Med. Virol. 80: 583).

Said use or method comprises one or more administration(s) (1, 2, 3, 4, 5, 6, 7, 8, 9, 10, etc) of a therapeutically effective amount of said active agent(s), said administrations being separated from each other by an appropriate period of time and being carried out by the same route of administration or by different routes of administrations at the same site or at different sites. Intramuscular and subcutaneous routes are particularly preferred in the context of the invention. Three subcutaneous administrations separated from each other by approximately one week are particularly suitable for MVA-based compositions and vectors whereas one or two intramuscular or subcutaneous administration(s) are particularly suitable for Ad-based compositions and vectors which can be separated from each other by approximately one month or more. The first series of administrations can be followed by one or more subsequent administration(s) using the same active agent(s) two or several months after so as to recall the anti-HBV immune response.

If desired, the method or use of the invention can be carried out in combination with one or more conventional therapeutic modalities (e.g. radiation, chemotherapy and/or surgery). Preferably, the method or use of the invention is associated with the one or more drugs which are available for treating or preventing HBV infections, HBV-associated diseases and pathologic conditions. Their administration may precede, be concomitant, or subsequent to the administration of the active agent of the invention. Representative examples of suitable drugs include without limitation polymerase inhibitors, RNase H inhibitors, nucleoside analogs, nucleotide analogs, TLR agonists, IFN, N-glycosylation inhibitors, siRNA, antisense oligonucleotides, anti-HBV antibodies, immune modulators, therapeutic vaccines and antitumor agents usually used in the treatment of HBV-associated liver cancers (e.g. adriamycin, adriamicin with lipiodol or sorasenib). Moreover, the active agent(s) may also be used in combination with other therapeutic vaccines such as synthetic peptides, recombinant antigens, VLPs, vectors encoding HBV proteins (Core, preS1, PreS2, S and/or polymerase) which are particularly suited to trigger an anti-HBV humoral response. A particularly suitable method or use according to the invention is in combination with standard of care and especially treatment with cytokines (e.g. IFNalpha, pegylated IFNa2a or 2b such as Pegasys (Roche), Pegintron (Schering Plough) or IntronA (Schering Plough)) and/or with nucleotide or nucleoside analogs (NUCs) such as lamivudine, entecavir, telbivudine, adefovir, dipivoxil or tenofovir. The treatment with NUCs is only partially effective (infection resolution is observed in only 3-5% of subjects after 1 year of treatment) and needs long term therapy (may be life-long). It is expected that the active agents and methods of the invention bring an immune dimension that permits to complement NUC's action on viral replication, thus resulting in an improvement of such treatments (e.g. by decreasing doses of NUCs or length of NUC treatment required to achieve a therapeutic benefit) or an increase of the percentage of infection resolution (greater than 5%).

In a specific embodiment, the method or use of the invention can be carried out according to prime boost modality which comprises sequential administrations of one or more priming composition(s) and one or more boosting composition(s). Typically, the priming and the boosting compositions use different vectors which comprise or encode at least an antigenic domain in common. Moreover, the priming and boosting compositions can be administered at the same site or at alternative sites by the same route or by different routes of administration. For example, compositions based on polypeptide can be administered by a mucosal route whereas compositions based on vectors are preferably injected, e.g. subcutaneous injection for a MVA vector, intramuscular injection for a DNA plasmid and subcutaneous or intramuscular injection for an adenoviral vector.

In one embodiment, the priming is carried out with a MVA vector and the boosting with an Ad vector, with a specific preference for the MVA and/or the Ad vector encoding a mutant polymerase protein or a fusion protein described herein, e.g. the fusion protein shown in SEQ ID NO: 8. The MVA vector is administered to the organism one or more times followed by the administration of the adenoviral vector one or more times with a specific preference for at least 3 subcutaneous administrations of the MVA vector separated by a period of time varying from 3 days to 3 months followed by a intramuscular or subcutaneous boost of the adenovirus vector (e.g. from approximately 1 month to 1 year after the MVA prime).

In another embodiment, the priming is carried out with a plasmid DNA vector and the boosting with a MVA vector, with a specific preference for the plasmid and/or the MVA vector encoding a mutant polymerase protein or a fusion protein described herein, e.g. the fusion protein shown in SEQ ID NO: 8). The DNA vector is administered to the organism one or more times followed by the administration of the MVA vector one or more times with a specific preference for at least 3 intramuscular administrations of the DNA vector separated by a period of time varying from 2 weeks to 3 months and at least one subcutaneous boost of the MVA vector (e.g. from approximately 1 month to 1 year after the DNA prime).

Preferably, the DNA vector is administered through electroporation.

The present invention also relates to a kit of parts for use in the treatment of an HBV infection or an HBV-associated disease or pathologic condition, wherein said kit comprises a plurality of active agents selected from the group consisting of the mutant polymerase polypeptide, fusion protein, nucleic acid molecule, vector, host cell and/or composition of the invention and instructions for administering said plurality of active agents to an organism in need thereof. More preferably, the organism is a patient chronically infected with HBV.

All of the above cited disclosures of patents, publications and database entries are specifically incorporated herein by reference in their entirety to the same extent as if each such individual patent, publication or entry were specifically and individually indicated to be incorporated by reference.

EXAMPLES

1. Material and Methods

Figure 1:
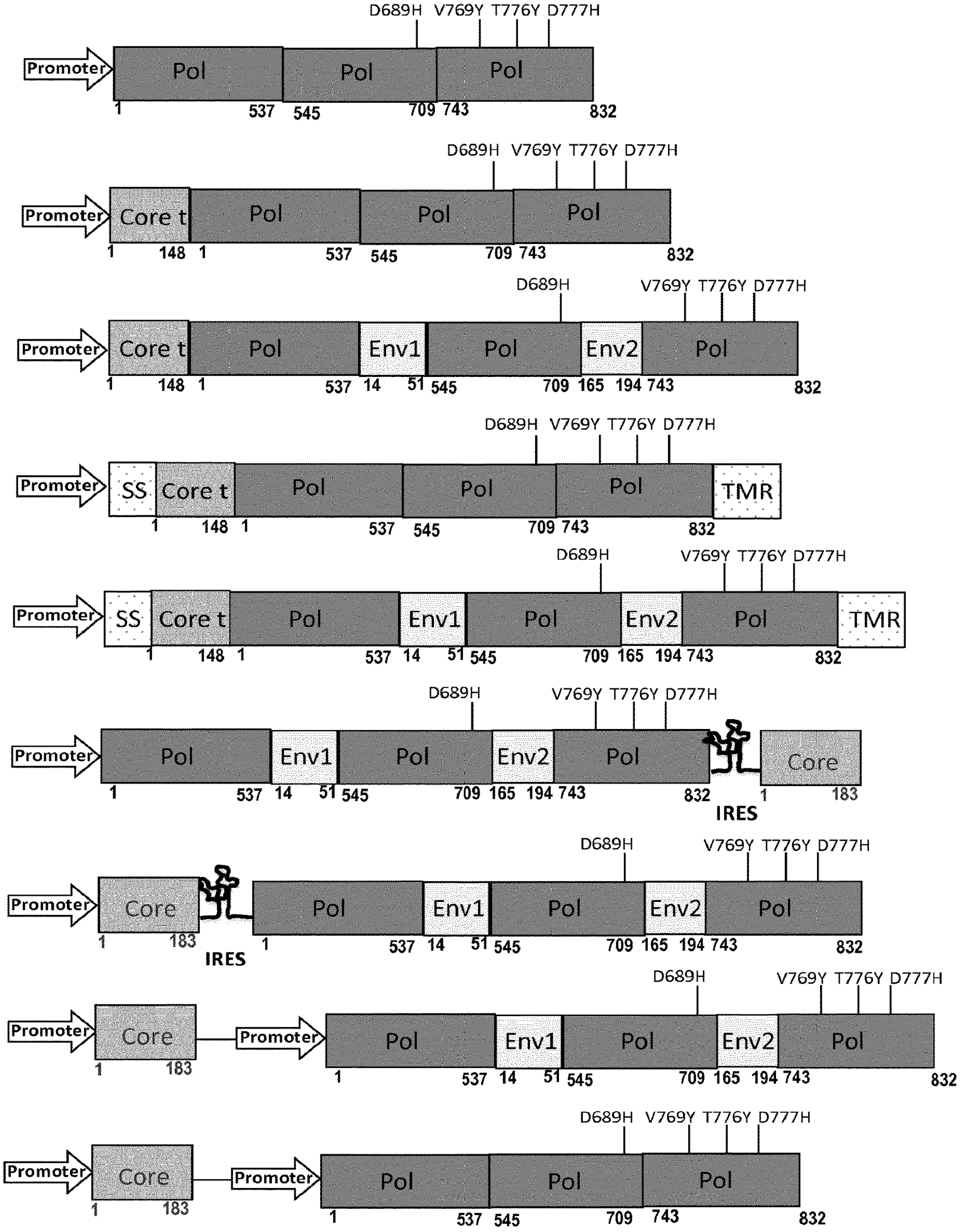
FIG. 1 illustrates the mutant polymerase polypeptides, fusion proteins and antigenic combinations described in the invention.

The constructions described below (see FIG. 1) are carried out according to the general genetic engineered and molecular cloning techniques detailed in Maniatis et al. (1989, Laboratory Manual, Cold Spring Harbor Laboratory Press, Cold Spring Harbor N.Y. or subsequent editions) or according to the manufacturer's recommendations when a commercial kit is used. PCR amplification techniques are known to the person skilled in the art (see for example PCR protocols—A guide to methods and applications, 1990, published by Innis, Gelfand, Sninsky and White, Academic Press). The recombinant plasmids carrying the ampicillin resistance gene are replicated in the *E. coli* C600 (Stratagene) on agar or liquid medium supplemented with 100 g/ml of antibiotic.

MVA vector construction are generated by homologous recombination between a shuttle plasmid and the MVA genome as previously described in Erbs et al. (2008, Cancer gene Ther. 15: 18). The "basic" shuttle plasmid contains a multiple cloning site, a vaccinia virus (VV) promoter surrounded by the flanking sequences of deletion III as well as the *E. Coli* xanthine-guanine phosphoribosyl-transferase (GPT) selection gene under the control of p11K7.5 vaccinia promoter (Falkner and Moss, 1988). Briefly, CEF cells were infected with a genomic MVA without any inserted transgene (MVA-null) and then transfected by $CaCl_2$ precipitation with the shuttle plasmid carrying the gene of interest cloned downstream the VV promoter. Homologous recombination occurred between MVA-null and the shuttle plasmid and recombinant viruses were isolated by multiple steps of mycophenolic acid selection. Recombinant MVA viruses were controlled by PCR, amplified in CEF and virus stocks were titrated on CEF by plaque assay.

For adenoviral vector construction, an adenoviral shuttle plasmid is first constructed by inserting the nucleic acid molecule of interest into the "basic" shuttle plasmid pTG13135. Typically, the nucleic acid molecule is inserted into the NheI and NotI restriction sites of pTG13135 containing a CMV-driven expression cassette surrounded by adenoviral sequences (adenoviral nucleotides 1-454 and nucleotides 3513-5781 respectively) to allow further generation of the vector genome by homologous recombination (Chartier et al., 1996, J. Virol. 70:4805). The adenoviral vector is then obtained by homologous recombination between the recombinant shuttle vector digested by Bst1107I and PacI and pTG15375 (encoding the complete adenoviral genome) linearized by ClaI digestion. The resulting adenoviral vector is E3 (nucleotides 27867-30743) and E1 (nucleotides 455-3512) deleted, with the E1 region replaced by the expression cassette containing, from 5' to 3', the CMV immediate-early enhancer/promoter, a chimeric human β-globin/IgG intron (as found in pCI vector available in Promega), the nucleic acid molecule of interest and the SV40 late polyadenylation signal. Adenoviral particles are then obtained by transfecting the PacI linearized viral genome into an E1 complementation cell line. Virus propagation, purification and titration is made as described previously (Erbs et al., 2000, Cancer Res. 60:3813)

1.1. Vectors Constructions and Production

The vectors illustrated hereinafter have been engineered to express the mutant polymerase polypeptide eventually fused to the Core polypeptide and/or immunogenic domains of the envelope protein. All HBV sequences originate from HBV strain Y07587 which sequence is described in international databases (Genbank Y07587) and in different publications. It is a genotype D virus of serotype ayw.

The following examples illustrate the fusion of a truncated Core polypeptide (aa 1-148) with a mutated polymerase polypeptide (designated Pol*) comprising two internal deletions (from positions 538 to 544 and from positions 710 to 742) and 4 amino acid substitutions (D689H, V769Y, T776Y and D777H respectively) as represented in SEQ ID NO: 6 as well as a longer fusion further comprising two immunogenic Env domains (Env1 and Env2 respectively extending from amino acids 14 to 51 and from amino acids 165 to 194 of the HBs protein) inserted in place of the deleted pol regions as represented in SEQ ID NO: 8.

1.1.1. Construction and Production of Plasmid and Adenovirus Vectors Expressing Truncated Core-Pol*-Env1-Env2 (or Core-Pol-Env1-Pol-Env2-Pol) Fusion A synthetic gene (3024 nucleotides described in SEQ ID NO: 15) encoding the truncated Core-Pol*-Env1-Env2 fusion protein (amino acid sequence is shown in SEQ ID NO: 8) was synthesized by GENEART (Regensburg, Germany). The synthetic fragment was inserted into the NheI and NotI restriction sites of pTG13135 shuttle plasmid, providing pTG18188. An adenoviral vector was then obtained by homologous recombination between pTG18188 digested by Bst1107I and PacI and pTG15375 linearized by ClaI digestion. The resulting adenoviral vector pTG18201 is E3 and E1 deleted, with the E1 region replaced by the expression cassette containing the synthetic sequence encoding the truncated Core-Pol*-Env1-Env2 driven by the CMV promoter. Adenoviral particles (AdTG18201) were obtained by transfecting the Pad linearized viral genome into an E1 complementation cell line.

1.1.2. Construction and Production of Plasmid and Adenovirus Vectors Expressing Truncated Core-Pol*

A synthetic gene (2820 nucleotides described in SEQ ID NO: 14) encoding a truncated Core-Pol* fusion protein was synthesized by GENEART (Regensburg, Germany). The synthetic fragment was inserted into the NheI and NotI restriction sites of pTG13135 shuttle plasmid, providing pTG18194. An adenoviral vector was then obtained by homologous recombination between pTG18194 digested by Bst1107I and PacI and pTG15375 linearized by ClaI digestion. The resulting adenoviral vector pTG18202 is E3 and E1 deleted, with the E1 region replaced by the expression cassette containing the synthetic sequence encoding the truncated Core-Pol* driven by the CMV promoter. Adenoviral particles (AdTG18202) were obtained by transfecting the PacI linearized viral genome into an E1 complementation cell line.

1.1.3. Construction and Production of Plasmid and Adenovirus Vectors Expressing Pol*

A synthetic gene (2379 nucleotides described in SEQ ID NO: 13) encoding the Pol mutant polypeptide was synthesized by GENEART (Regensburg, Germany). The synthetic fragment was inserted into the NheI and NotI restriction sites of pTG13135 shuttle plasmid, providing pTG18195. An adenoviral vector was then obtained by homologous recombination between pTG18195 digested by Bst1107I and PacI and pTG15375 linearized by ClaI digestion. The resulting adenoviral vector pTG18203 is E3 and E1 deleted, with the E1 region replaced by the expression cassette containing the synthetic sequence encoding Pol* driven by the CMV promoter. Adenoviral particles (AdTG18203) were obtained by transfecting the PacI linearized viral genome into an E1 complementation cell line.

1.2. Immunogenicity Evaluation in a Mouse Model

Antigen immunogenicity was evaluated in vivo by Elispot IFNγ assays and Intracellular cytokine staining (ICS) following immunization of HLA transgenic mice.

1.2.1 Mouse Model

The HLA-A2.1 transgenic mice used in the study were described by Pascolo et al. (1997, J. Exp. Med. 185:2043). These mice have the H-$2D^b$ and murine $\beta_2$-microglobulin genes knocked-out and express a transgenic monochain histocompatibility class I molecule (HHD molecule) in which the C-terminus of the human β2m is covalently linked to the N-terminus of a chimeric heavy chain (HLA-A*0201 α1-α2, H-$2D^b$ α3 transmembrane and intracytoplasmic domains). Seven to 10 weeks-old mice (male and female) were immunized. Average weight of the mice is around 25-30 g.

The HBV transgenic mice used in the study were described by Halverscheid et al (2008, J. Med. Virol. 80: 583-590) and kindly provided by Reinhold Schirmbeck. These mice are on a C57Bl/6J genetic background and transgenic for the HBV genome (1.4 copy of the HBV genome with a mutation at position 1438 (T to C) which avoid the expression of the small form of the HBsAg protein and inhibit the formation of HBV infectious particles). Ten to 16 weeks-old mice (male and female) were immunized. Average weight of the mice is around 25-30 g.

1.2.2. Immunization Protocols 1.2.2.1 DNA Immunization Protocols

DNA immunization protocols were run in order to evaluate the immunogenicity of the different fusion proteins encoded by the plasmids illustrated in Example 1.1. The DNA used for immunization was produced in endotoxin-free conditions. Mice were immunized twice at 15-day interval with 100 μg/injection of each tested plasmid via intramuscular route in the tibialis anterior muscle. A cardiotoxin injection was done prior to the 1rst DNA injection in order to favor DNA immunogenicity. Cellular immune response was evaluated 15 days following the last DNA injection.

1.2.2.2 Adenovirus Immunization Protocols

Adenovirus immunization protocols were run in order to compare the immunogenicity of the different fusion proteins encoded by the Ad vectors which were produced as described in Example 1.1. Mice were immunized once with the adenovirus encoding the different fusion proteins ($10^8$ iu/mouse/injection) via sub-cutaneous route at the base of the tail. Cellular immune response was evaluated 15 days following the last adenovirus injection.

Different doses of adenoviruses were also evaluated with the AdTG18201. Mice were immunized once with $10^5$, $10^6$, $10^7$, $10^8$ or $10^9$ iu of AdTG18201 by sub-cutaneous route at the base of the tail.

Different schedules of immunization were also tested with the AdTG18202 and mice were injected one, two, three or 6 times at different time interval. Each injection was performed with $10^8$ iu/mouse via sub-cutaneous route at the base of the tail. One, 3 or 6 injections at 1 week interval were compared side by side. One injection 2 weeks or 20 weeks before the time of monitoring of induced T cell responses, 2 injections at 2 or 4 month interval and 3 injections at 2 month interval were also compared side by side.

1.2.3 Peptides

Peptides used for cells stimulation in vitro are either short peptides of 9 to 10 amino acids which are described or predicted as HLA-A2 restricted epitopes or long peptides of 15 amino acids included in peptide libraries covering all the antigens of interest.

Short peptides corresponding to described or predicted HLA-A2 restricted epitopes of Core protein, Pol protein or Env domains were synthesized by Eurogentec (Belgium) and were dissolved in 100% DMSO (sigma, D2650) at a concentration of 10 mM.

Peptides libraries covering the whole Core, Pol and Envelope domains were synthesized by ProImmune (Oxford, United Kingdom). The Core, Pol and Env libraries were composed of 15 mer peptides overlapping by 11 amino acids. Each crude peptide was dissolved in 100% DMSO (sigma, D2650) at a concentration of 50 mg/ml. For each library, peptides were pooled to a concentration of 2 mg/ml per peptide:

- HBV Core protein was covered by 2 pools of 21 and 22 peptides (Pool 1 (PC1): 22 peptides covering Core residues 1 to 100; Pool 2 (PC2): 21 peptides covering Core residues 89 to 183);
- HBV Pol protein was covered by 8 pools of 24 peptides (Pool 1 (PP1): 24 peptides covering aa 45 to 151; Pool 2 (PP2): 24 peptides covering aa 141 to 251 (peptide from aa 205 to 219 was excluded because of insolubility in 100% DMSO or DMSO+Tris 100 mM pH9; peptide from aa 221 to 235 was dissolved in DMSO+Tris 100 mM pH9 because of insolubility in 100% DMSO); Pool 3 (PP3): 24 peptides covering aa 241 to 347; Pool 4 (PP4): 24 peptides covering aa 337 to 447 (peptide from aa 373 to 387 was excluded because of insolubility in 100% DMSO or DMSO+Tris 100 mM pH9); Pool 5 (PP5): 24 peptides covering aa 437 to 543; Pool 6 (PP6): 24 peptides covering aa 533 to 639; Pool 7 (PP7): 24 peptides covering aa 629 to 735; Pool 8 (PP8): 24 peptides covering aa 725 to 835);

Env domains were covered by 2 pools of 9 and 10 peptides (Pool 1 (PE1): 10 peptides covering HBs residues 9 to 59; Pool 2 (PE2): 9 peptides covering HBs residues 157 to 194).

For experiments performed in HBV transgenic mice, with a C57BL/6J genetic background, HBV peptides described in the literature or identified in previous experiments as being reactive in mice with a C57Bl/6J genetic background were used for cell stimulation in vitro. They are either short peptide (VSAAFYHLPL for polymerase; SEQ ID NO: 24) or long peptides (NLNVSIPWTHKVGNF called N13F for polymerase (SEQ ID NO: 25) and FLWEWASARFSWLSL called F13L for envelope protein (SEQ ID NO: 26)). They were synthesized by Eurogentec (Belgium) or by ProImmune (Oxford, United Kingdom). Each peptide was dissolved in 100% DMSO (sigma D2650) at a concentration of 10 mM. They were used at a concentration of 10 μM during the ICS assays (even when tested as a mix of 2 peptides).

1.2.4. IFNg Elispot Assays

Splenocytes from immunized mice were collected and red blood cells were lysed (Sigma, R7757). $2.10^5$ cells per well were cultured in triplicate for 40 h in Multiscreen plates (Millipore, MSHA S4510) coated with an anti-mouse IFNγ monoclonal antibody (BD Biosciences; 10 μg/ml, 551216) in MEM culture medium (Gibco, 22571) supplemented with 10% FCS (JRH, 12003-100M), 80 U/mL penicillin/80 μg/mL streptomycin (PAN, P06-07-100), 2 mM L-glutamine (Gibco, 25030), lx non-essential amino acids (Gibco, 11140), 10 mM Hepes (Gibco, 15630), 1 mM sodium pyruvate (Gibco, 31350) and 50 μM β-mercaptoethanol (Gibco, 31350) and in presence of 10 units/ml of recombinant murine IL2 (Peprotech, 212-12), alone as negative control, or with:

- 10 μM of a selected HLA-A2 restricted peptide present in HBV antigens encoded by plasmids (FLP, ILC for Core, VLQ, FLG and GLS for Env and SLY for Pol) described in SEQ ID NO: 18-23) or an irrelevant one;
- a pool of peptides at a final concentration of 5 μg/ml per peptide
- 5 μg/ml of Concanavalin A (Sigma, C5275) for positive control.

IFNg-producing T cells were quantified by Elispot (cytokine-specific enzyme linked immunospot) assay as previously described (Himoudi et al., 2002, J. Virol. 76:12735). The number of spots (corresponding to the IFNg-producing T cells) in negative control wells were subtracted from the number of spots detected in experimental wells containing HBV peptides. Results are shown as the mean value obtained for triplicate wells. An experimental threshold of positivity for observed responses (or cut-off) was determined by calculating a threshold value which corresponds to the mean value of spots observed with medium alone+2 standard deviations, reported to $10^6$ cells. A technical cut-off linked to the CTL Elispot reader was also defined as being 50 spots/$10^6$ cells (which is the value above which the CV (coefficient of variation) of the reader was systematically less than 20%). The highest value between the technical cut-off and the experimental threshold calculated for each experiment was taken into account to define the cut-off value of each experiment. Statistical analyses of Elispot responses were conducted by using a Mann-Whitney test. P value equal or inferior to 0.05 will be considered as significant.

1.2.5. Intracellular Cytokine Staining (ICS) Assays

ICS were performed on splenocytes from each animal of each group. Following red blood cells lysis with lysis buffer (Sigma, R7757), $2\times10^6$ cells per well in flat-bottom 96-well plate were incubated in complete alpha MEM culture medium (Gibco BRL, 22571) in the presence of 10 units/ml of murine recombinant IL-2 (Peprotech, 212-12) alone as negative control or with 1 μM of specific HBV peptide or with a pool of peptides at a final concentration of 5 g/ml per peptide or with 1 μM of an irrelevant peptide. The GolgiPlug (BD Biosciences, 555029) was immediately added at a 1 μl/ml final concentration for 5 h. Then, cells were harvested in V-bottom 96-well plates and washed with 1% FCS-PBS. Staining was performed using monoclonal antibodies against CD3 (hamster MAb anti-CD3e-PE, dilution 1/200), CD8 (rat MAb anti CD8a-APC, dilution 1/600) and CD4 (rat MAb anti-CD4-PerCP, dilution 1/600) (all from BD Biosciences, 553063, 553035 and 553052 respectively) in 50 μl of 1% FCS-PBS for 15 min at room temperature. After washing, cells were fixed and permeabilized with Cytofix/Cytoperm and washed with Perm/Wash solution (BD Biosciences, 554714). Then, the anti-mouse IFNg-PE antibodies (BD Biosciences, 554412557724) and anti-mouse TNFa-Alexa488 antibodies (BD Biosciences, 557719) or the anti-mouse IFNg-PE antibodies (BD Biosciences, 554412557724) were added for 15 min at room temperature and after washing with Perm/Wash, cells were resuspended in 1% FCS-PBS and analysed by flow cytometry using a FacsCalibur (Becton Dickinson). CD3e+, CD8a+ cells or CD3e+, CD4+ cells were gated to determine percentages of IFNg+ CD8+ or IFNg+ CD4+ T or TNFa+ CD8+ or TNFa+ CD4+ T or IFNg+ TNFa+ CD8+ or IFNg+ TNFa+ CD4+ T cell population. The percentage obtained in medium only was considered as background.

For experiments performed in HBV transgenic mice, ICS were also performed on liver cells of each animal of each group. After euthanasia of the mouse, the liver was perfused in situ by the hepatic portal vein with cold PBS until the organ becomes pale. The liver was harvested, placed in PBS+FCS 2% solution, cut into small pieces, pressed gently through a 70 m cell-strainer and then suspended in cold PBS+2% FCS solution. After centrifugation, cells were washed again with cold PBS+2% FCS solution. After a new centrifugation, the pellet containing cells was resuspended in 10 mL of Percoll solution, centrifuged for 12 minutes at 700 g at room temperature and washed again with PBS+2% FCS solution. Then red blood cells were lysed as described before for splenocytes and all subsequent steps were performed as described in the previous paragraph for splenocytes. Of note, for the liver, as the quantity of T lymphocytes collected is limited, number of cells per well is variable: all obtained cells were cultured in a way that an equivalent quantity of cells was dispatched in all wells.

1.2.6 In Vivo CTL Assays

In vivo CTL assay was performed as described by Fournillier et al. (2007, Vaccine, 25: 7339-53) in HLA-A2 transgenic mice. Splenocytes suspensions were obtained from syngenic mice spleens and adjusted to $20\times10^6$ cells/mL after lysis of red blood cells. Half of the cells were incubated with the HBV peptide of interest (SLY, FLP or ILC) at 10 μM final concentration for 1 h at 37° C. and half of the cells was left unpulsed. 5(6)-carboxyfluorescein diacetate succinimidyl ester (CFSE) (Molecular probes, C1157) was then added at 10 μM (CFSE-high) to unpulsed cells and 1 μM (CFSE-low) to HBV-peptide pulsed cells for 10 min. After washing with PBS, all populations were mixed and $20\times10^6$ total cells were injected to anaesthetized mice via the retro-orbital sinus, mice being previously immunized (2 weeks earlier) by AdTG18201 or AdTG15149. Thus, CFSE-low population represented specific targets supposed to be lysed by cytotoxic T cells induced by the vaccination and CFSE-high population was an internal reference allowing assay normalization. Splenocytes from recipient mice were analyzed 24 h later by flow cytometer to detect the CFSE-labeled cells. For each animal, ratio between peptide-pulsed targets and unpulsed targets was calculated (R=Number CFSE-low cells/Number CFSE-high cells). The percentage of specific lysis for each animal was determined by the following formula: % lysis=$(1-R_{mouse}/R_{reference})\times 100$ where $R_{reference}$ is the mean R obtained for 2 naïve HLA-A2 mice which were injected with the same suspension of CFSE-labeled targets. A response was considered positive if the percentage of specific lysis was higher than 10%.

1.3 In Vitro Analysis of AdTG18201 by Electron Microscopy

A549 cells (Human lung adenocarcinoma epithelial cell line) were infected in suspension and under reduced medium volume conditions with AdTG18201 at different MOI (25 to 100) and then cultured for 16H, 24H or 48H before being collected for analysis. Cells were collected at these different timepoints and then fixed using glutaraldehyde 2% diluted in sodium cocadylate buffer 0.2M. Cells were then dried, included in blocks of resin and then cut in ultra-thin sections. Obtained grids were then stained using uranyl acetate and lead citrate and observed by electron microscopy.

2. Results 2.1. Immunogenicity of HBV Fusion Proteins Expressed by DNA Plasmids pTG18188 and pTG18194

The immunogenicity of the HBV fusion proteins expressed by DNA plasmids was assessed in HLA-A2 transgenic mice. Following two intramuscular injections of either pTG18188 (tCore-Pol*-Env1-Env2) or pTG18194 (tCore-Pol*) or pTG13135 as negative control (empty plasmid), specific T cell responses were evaluated by Elispot IFNg and ICS (IFNg/TNFa) using known HLA-A2 epitopes present in Polymerase, Core or the envelope domains and/or pools of overlapping peptides covering the HBV antigens of interest.

2.1.1. HBV Specific IFNγ Producing Cell Evaluation by Elispot Assays

Figure 2:
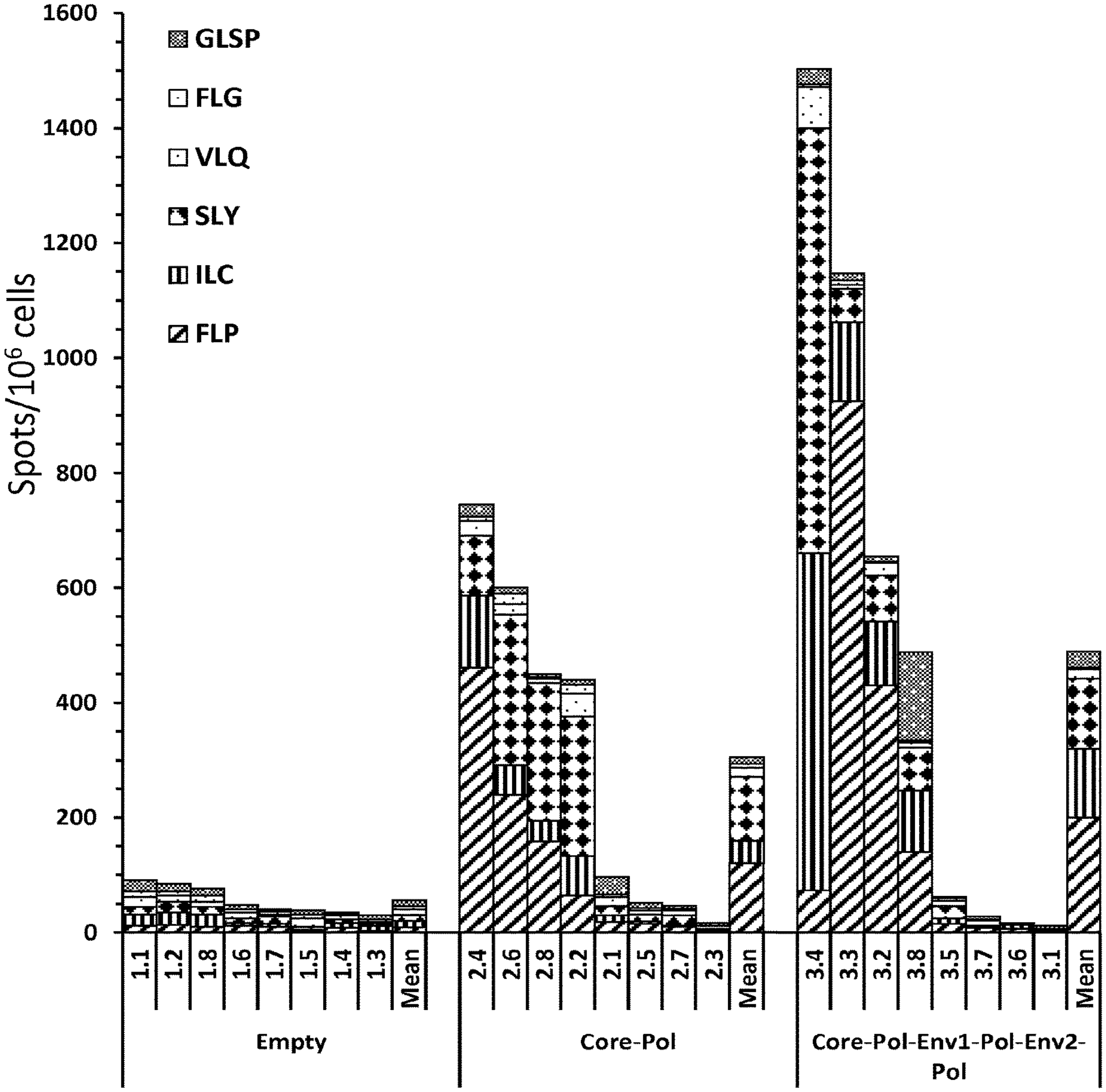
FIG. 2 illustrates Elispot IFNg assays carried out following immunization of HLA-A2 transgenic mice with plasmids pTG18188 (Core-Pol-Env1-Pol-Env2-Pol), pTG18194 (Core-Pol) or pTG13135 (Empty). Results are presented as the number of spots for $10^6$ cells corresponding to the frequency of IFNg producing cells specific of each HBV HLA-A2 peptides evaluated in the experiment for $10^6$ spleen cells of immunized mice. Each bar represent an individual mouse vaccinated by one or the other plasmid and indicated by its reference number (1.1 or 2.3 . . . etc) and the mean of all mice immunized with the same plasmid is also represented for each group (bar indicated as "mean" on the graph). For individual mouse and the means, frequency of IFNg producing cells specific of the different tested peptides are piled. Bars are filled with different symbols, each symbol representing the response against one specific HBV peptide as indicated by the legend on the graph.

As illustrated in FIG. 2, immunization with the plasmid pTG18194 encoding the HBV fusion protein "tCore-Pol*" induced IFNg producing cells specific of the HLA-A2 restricted SLY epitope (SEQ ID NO: 23) located within the HBV polymerase (positions 816-824). Immunization with the plasmid pTG18194 also resulted in the induction of high frequency of IFNg producing cells specific for 2 Core HLA-A2 restricted epitopes FLP (SEQ ID NO: 18, located within the HBV Core protein at position 18-27) and ILC (SEQ ID NO: 19 located within the HBV Core protein at position 99-108). Positive responses were observed in 4 out of the 8 vaccinated mice.

As illustrated in FIG. 2, the plasmid pTG18188 encoding the HBV fusion protein "Core-Pol*-Env1-Env2" also induced IFNg producing cells specific of the pol HLA-A2 epitope SLY and of the 2 Core HLA-A2 restricted epitopes FLP and ILC. Positive responses were observed in 4 out of the 8 vaccinated mice. In addition, IFNg-producing cells specific of HLA-A2 GLS epitope (SEQ ID NO: 22 located within Env2 at positions 185-194 of HBsAg) were also detected although at a weak frequency and in 1 vaccinated mouse.

Figure 3A:
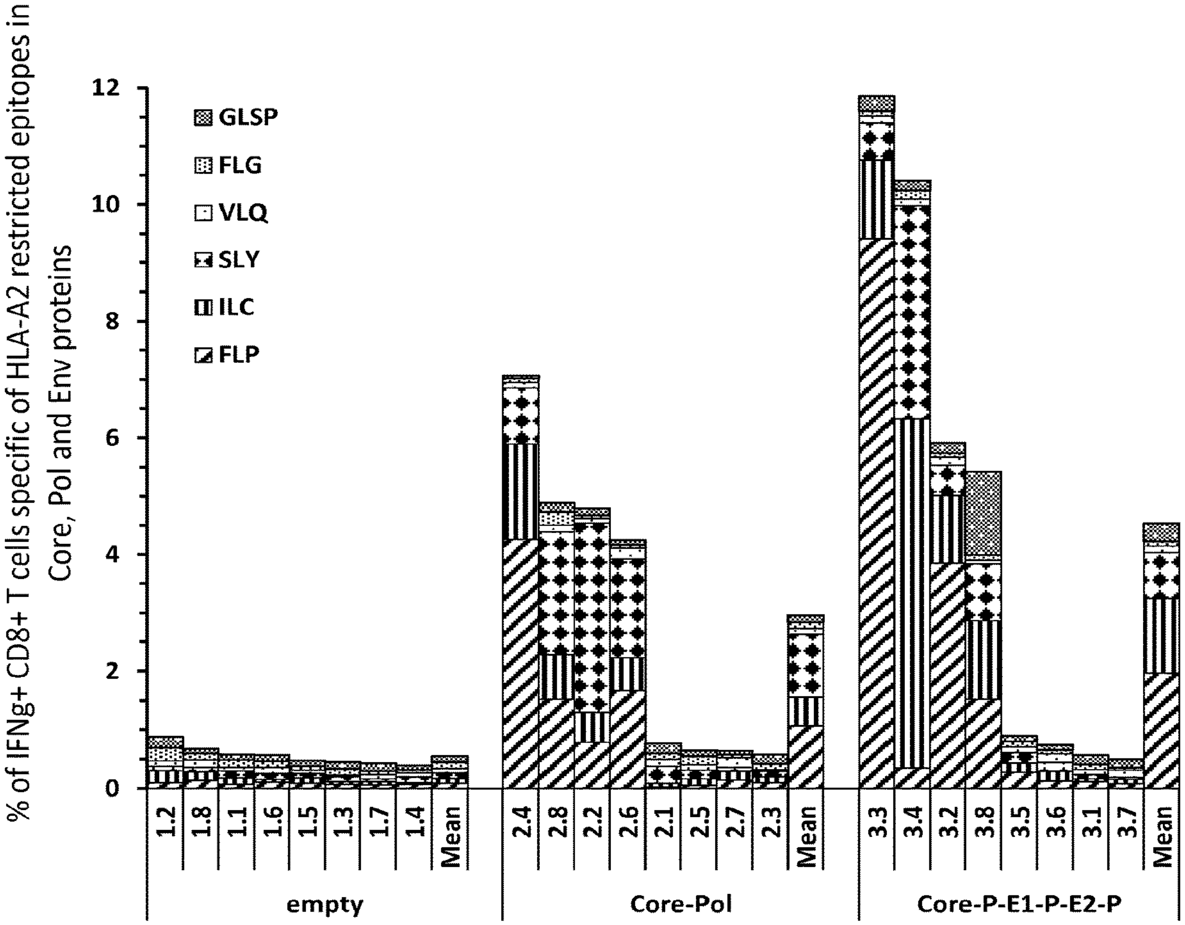
FIGS. 3A-F illustrates ICS assays carried out following immunization of HLA-A2 transgenic mice with plasmids pTG18188 (Core-P-E1-P-E2-P or Core-Pol-Env1-Pol-Env2-Pol), pTG18194 (Core-Pol) or pTG13135 (empty). Results are presented as the percentage of CD8 (FIGS. 3A, 3B, 3D and 3F), or CD4 (FIGS. 3C and 3E) T cells producing IFNg (alone or combined with TNFa) specific of each HBV HLA-A2 peptides (FIG. 3A) or peptide pools covering HBV core (FIGS. 3B and 3C), polymerase (FIGS. 3D and 3E) and env (FIG. 3F) antigens. Each bar represent an individual mouse vaccinated by one or the other plasmid and indicated by its reference number (1.1 or 2.3 . . . etc) and the mean of all mice immunized with the same plasmid is also represented for each group (bar indicated as "mean" on the graph). For individual mouse and the means, frequency of CD8 or CD4 T cells specific of the different tested peptides are piled. Bars are filled with different symbols, each symbol representing the response against one specific HBV peptide as indicated by the legend on the graph.

2.1.2. Evaluation of Induced HBV Specific IFNg Producing T CD8+ and CD4+ Cells by Intracellular Staining Assays 2.1.2.1. CD8 T Cell Response Specific of HLA-A2 Restricted Epitopes The percentage of CD8 T cells producing either IFNg alone or combined with TNFa targeting HLA-A2 restricted epitopes included into polymerase (SLY), Core (FLP and ILC) and envelope domains (VLQ, FLG and GLS) was evaluated by ICS assay. The results are shown in FIG. 3A as percentages of CD8+ T cell specific of these epitopes and producing IFNg (sum of single IFNg producing cells or double IFNg and TNFa producing cells). Four out of 8 animals immunized with pTG18194 (expressing tCore-Pol*) mounted IFNg producing CD8+ T cells specific of FLP, ILC and SLY HLA-A2 restricted epitopes located respectively in Core and Pol antigens. Similarly, 4 out of 8 animals immunized with pTG18188 expressing tCore-Pol*-Env1-Env2) also mounted IFNg producing T CD8+ T cells specific of FLP, ILC and SLY epitopes. In addition as already observed in ELISPOT assay, 1 out of 8 mice immunized with the plasmid pTG18188 displayed a response specific of the GLS HLA-A2 restricted epitope located within the Env2 domain mediated by IFNg producing CD8+ T cells. Immunization with pTG13135 did not induce any specific response as expected.

2.1.2.2 CD8 and CD4 T Cell Response Specific of Pools of Peptides Covering the Core Protein, Polymerase Protein and Env Domains.

Responses Specific of Pools of Peptides Covering the Core Protein

The percentage of CD8 and CD4 T cells able to produce either IFNg alone or combined with TNFa in response to pools of peptides covering the Core protein (PC) was evaluated by ICS assay. The results are expressed as percentages of CD8+ or CD4+ T cell specific of these pools of peptides and producing IFNg (sum of single IFNg producing cells or double IFNg and TNFa producing cells).

Figure 3B:
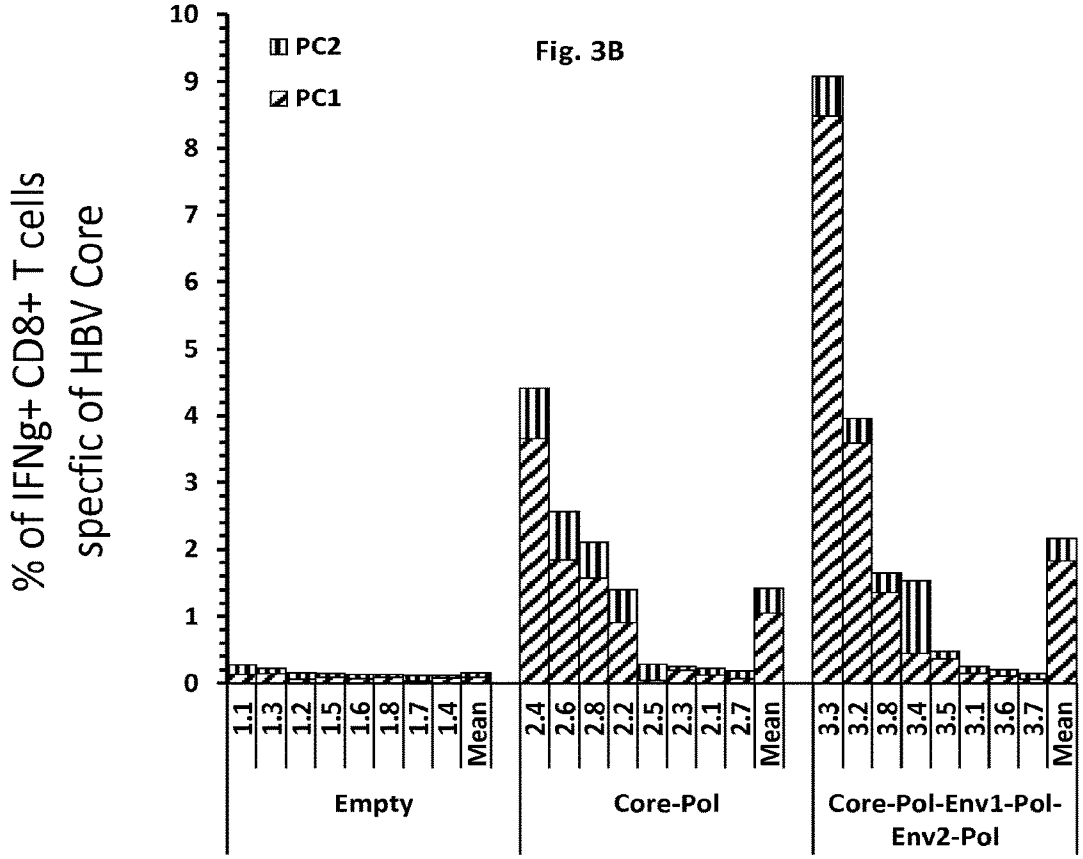

As shown in FIG. 3B, a positive percentage of CD8+ T cells producing IFNg was detected against the 2 pools of peptides covering the Core protein (PC1 and PC2), with a CD8+ T cell response mainly focused on peptides of Pool Core 1. The percentage of reactive CD8+ T cells observed in mice vaccinated by either the pTG18194 or the pTG18188 was significantly different from the percentage that was observed for mice vaccinated with the negative control (pTG13135) ($p<0.05$, Mann Withney test) for both peptide pools (1 and 2).

Figure 3C:
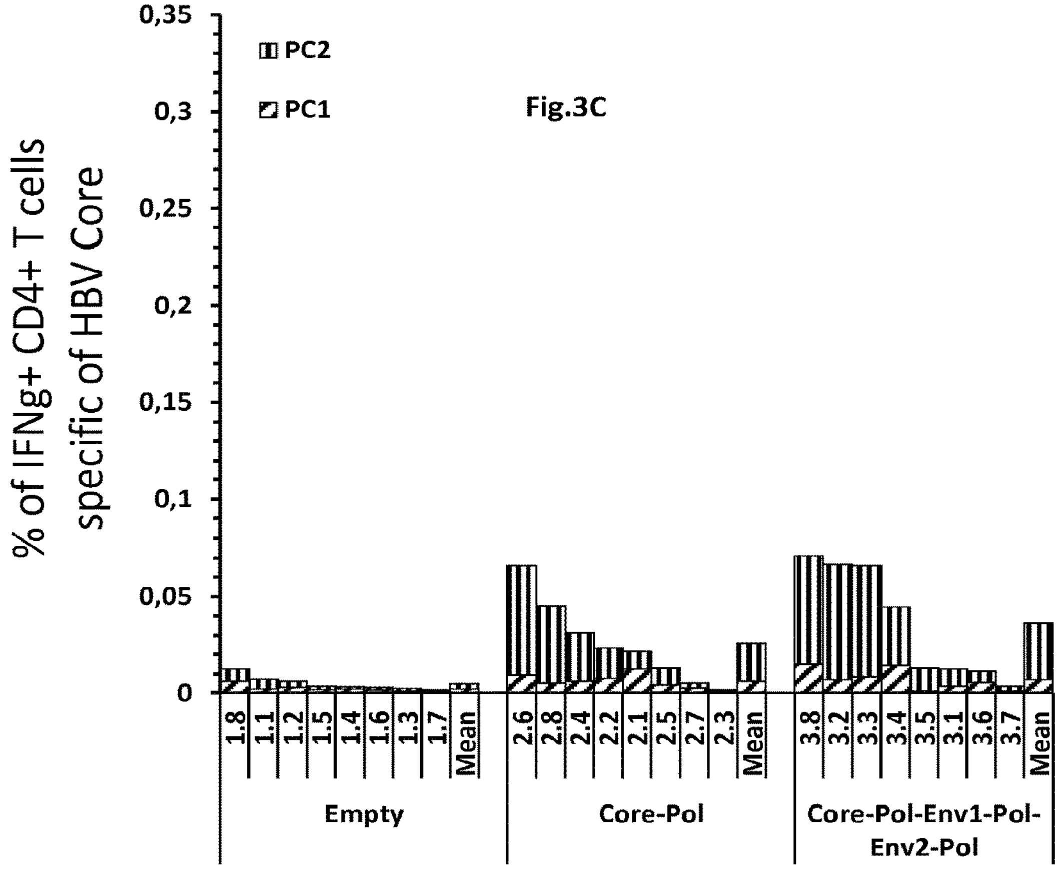

As shown in FIG. 3C, positive percentage of CD4+ T cells producing IFNg was also detected against one pool of peptides covering the Core protein, the pool Core 2 in the two groups of mice vaccinated with pTG18194 or pTG18188. The percentage of reactive CD4+ T cells observed in mice vaccinated by the pTG18188 was significantly different from the percentage that was observed for mice vaccinated with the negative control (pTG13135) ($p<0.05$, Mann Withney test) for pool Core 2.

Responses Specific of Pools of Peptides Covering the Polymerase Protein

The percentage of CD8 and CD4 T cells able to produce either IFNg alone or combined with TNFa in response to pools of peptides covering the polymerase protein was evaluated by ICS assay. The results are expressed as percentages of CD8+ or CD4+ T cell specific of these pools of peptides and producing IFNg (sum of single IFNg producing cells or double IFNg and TNFa producing cells).

Figure 3D:
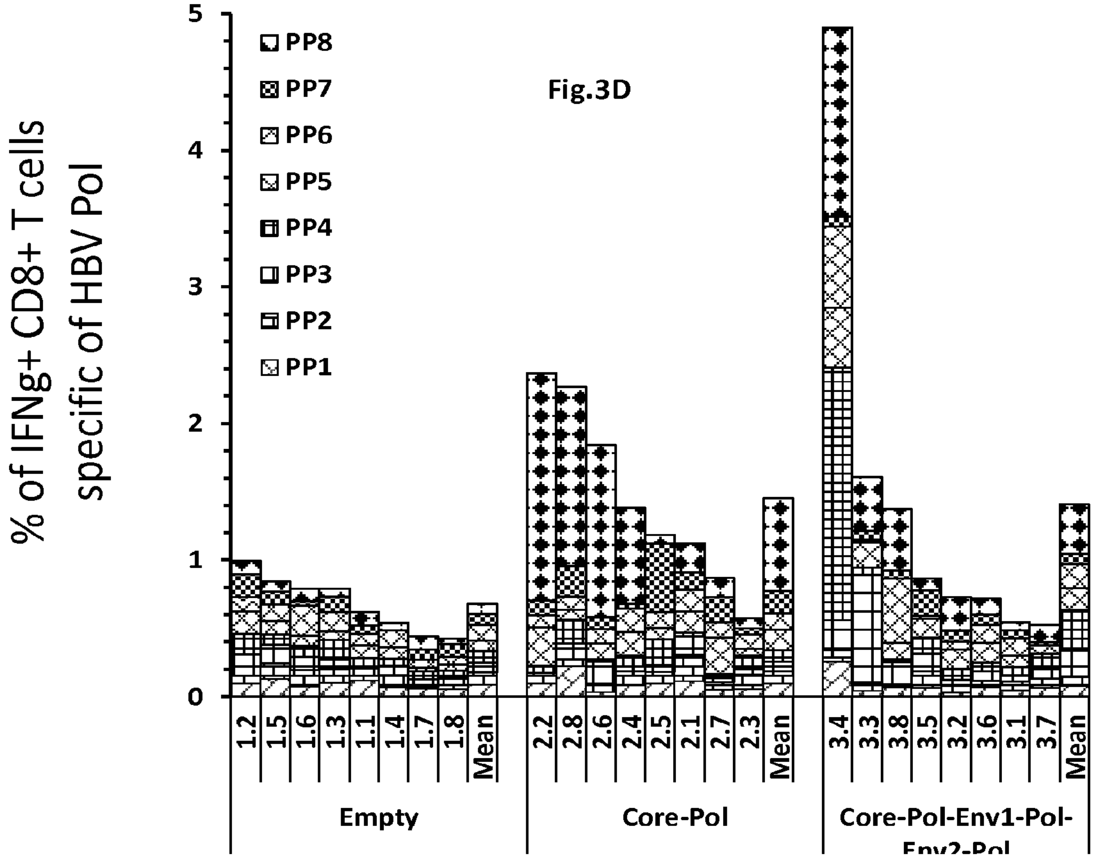

As shown in FIG. 3D, a positive percentage of CD8+ T cells producing IFNg was mainly detected against one pool of peptides, PP8. Specifically for PP8, the percentage of reactive CD8+ T cells observed in mice vaccinated by either the pTG18194 or the pTG18188 was significantly different from the percentage that was observed for mice vaccinated with the negative control (pTG13135) ($p<0.05$, Mann Withney test). Of note, one mouse in the group of mice vaccinated with pTG18188 also displayed positive percentage of IFNg producing CD8+ T cells against pool 4, pool 5 and pool 6.

Figure 3E:
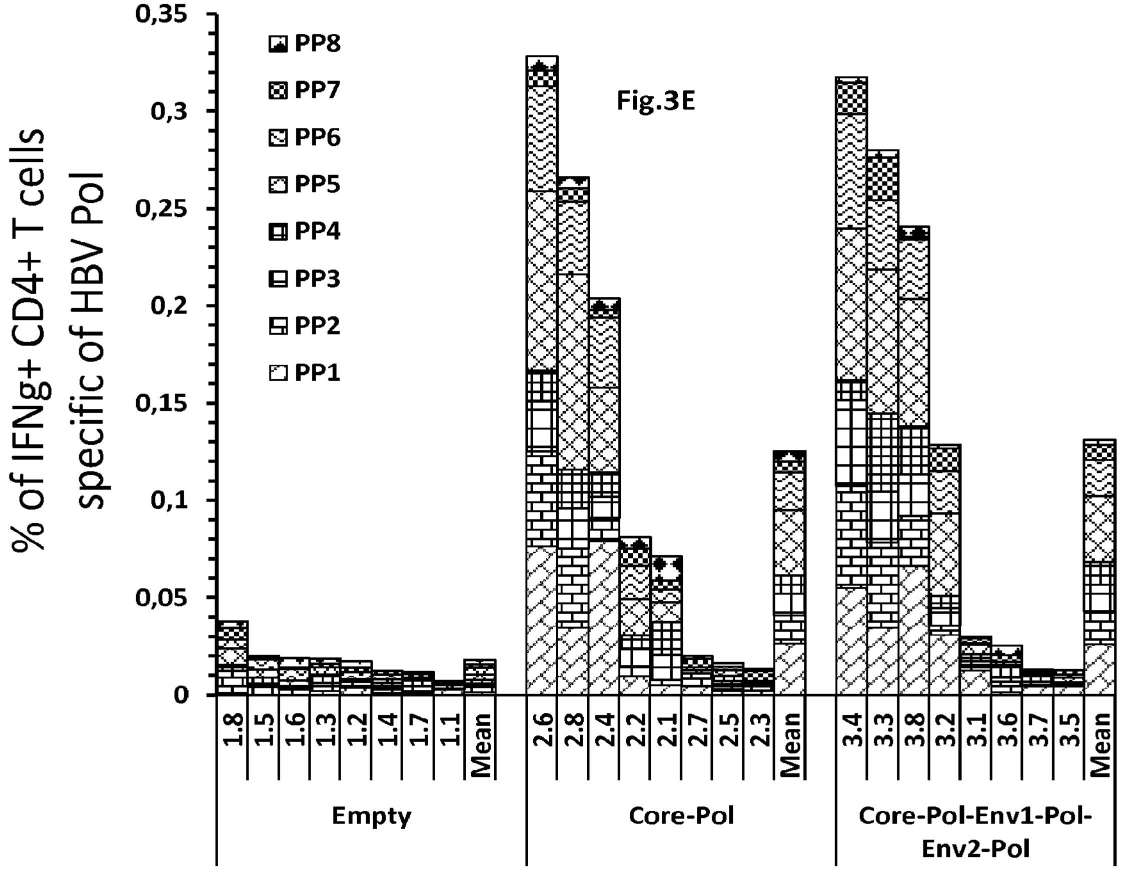

As shown in FIG. 3E, a weak but positive percentage of CD4+ T cells producing IFNg was detected against 4 pools of peptides covering the Pol protein, the pool Pol 1, pool Pol 4, pool Pol 5 and pool Pol 6 in the two groups of mice vaccinated with pTG18194 or pTG18188, with at least 3 out of the 8 tested mice in each group displaying responses.

Responses Specific of Pools of Peptides Covering the Envelope Domains

Figure 3F:
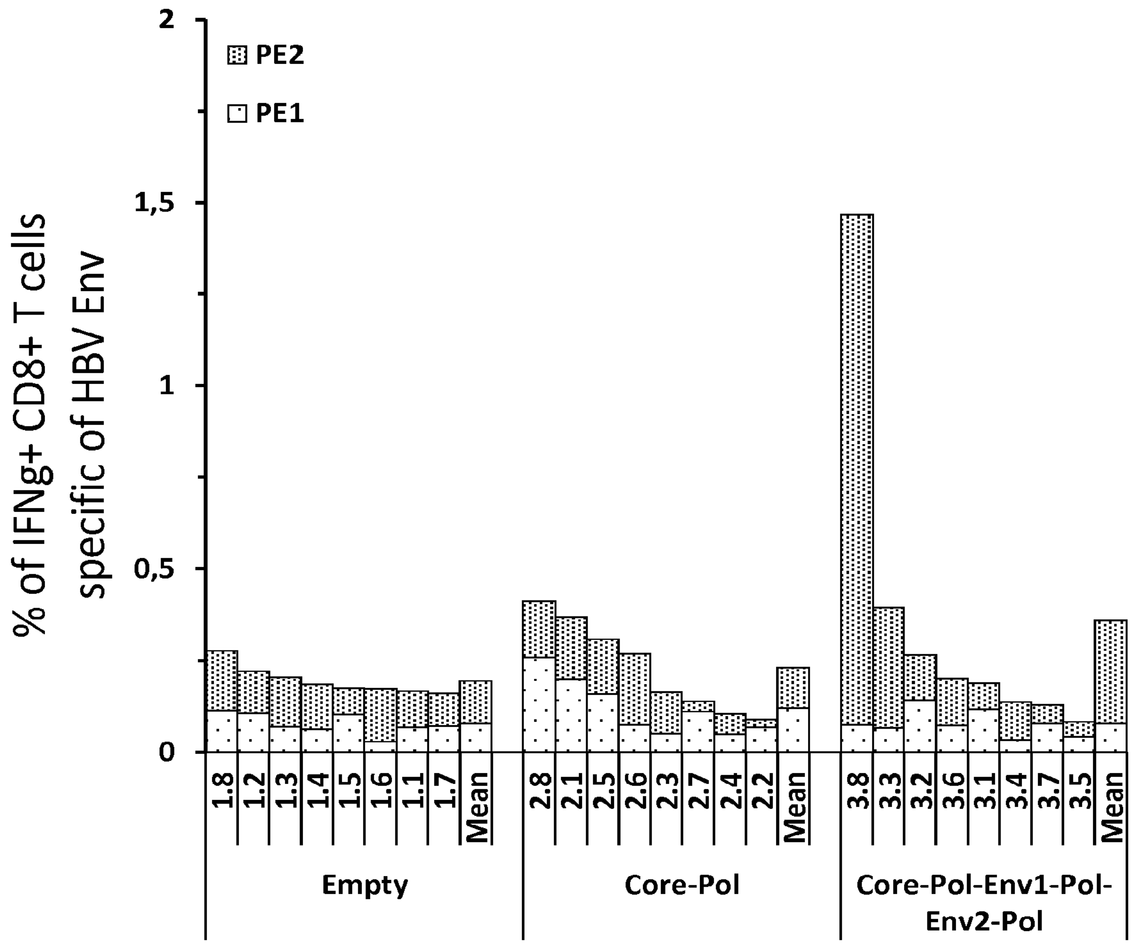

The percentage of CD8 and CD4 T cells able to produce either IFNg alone or combined with TNFa in response to pools of peptides covering the Envelope domains, Env1 and Env2, was evaluated by ICS assay. No specific CD4+ T cell response was detected during this experiment. The results for CD8+ T cell response are shown in FIG. 3F as percentages of CD8+ T cells specific of these pools of peptides and producing IFNg (sum of single IFNg producing cells or double IFNg and TNFa producing cells). Specifically, a weak but positive percentage of CD8+ T cells producing IFNg was detected for 1 mouse vaccinated with the pTG18188 against one pool of peptides, pool Env2.

2.2. Immunogenicity of HBV Fusion Proteins Expressed by Adenovirus AdTG18201, AdTG18202 and AdTG18203

2.2.1. Evaluation of HBV-Specific IFNg Producing T Cells by Elispots IFNg Using Pools of Overlapping Peptides The immunogenicity of the HBV Pol mutant and fusion proteins expressed by human adenovirus 5 was assessed in HLA-A2 transgenic mice immunized with either AdTG18201 or AdTG18202 or AdTG18203 or AdTG15149 (empty adenovirus used as negative control). Specific T cell responses induced following one subcutaneous injection of adenovirus were evaluated by Elispot IFNg using pools of overlapping peptides covering the HBV antigens of interest, Core (PC1-2), Polymerase (PP1-8) and Env (PE1-2) domains.

Figure 4:
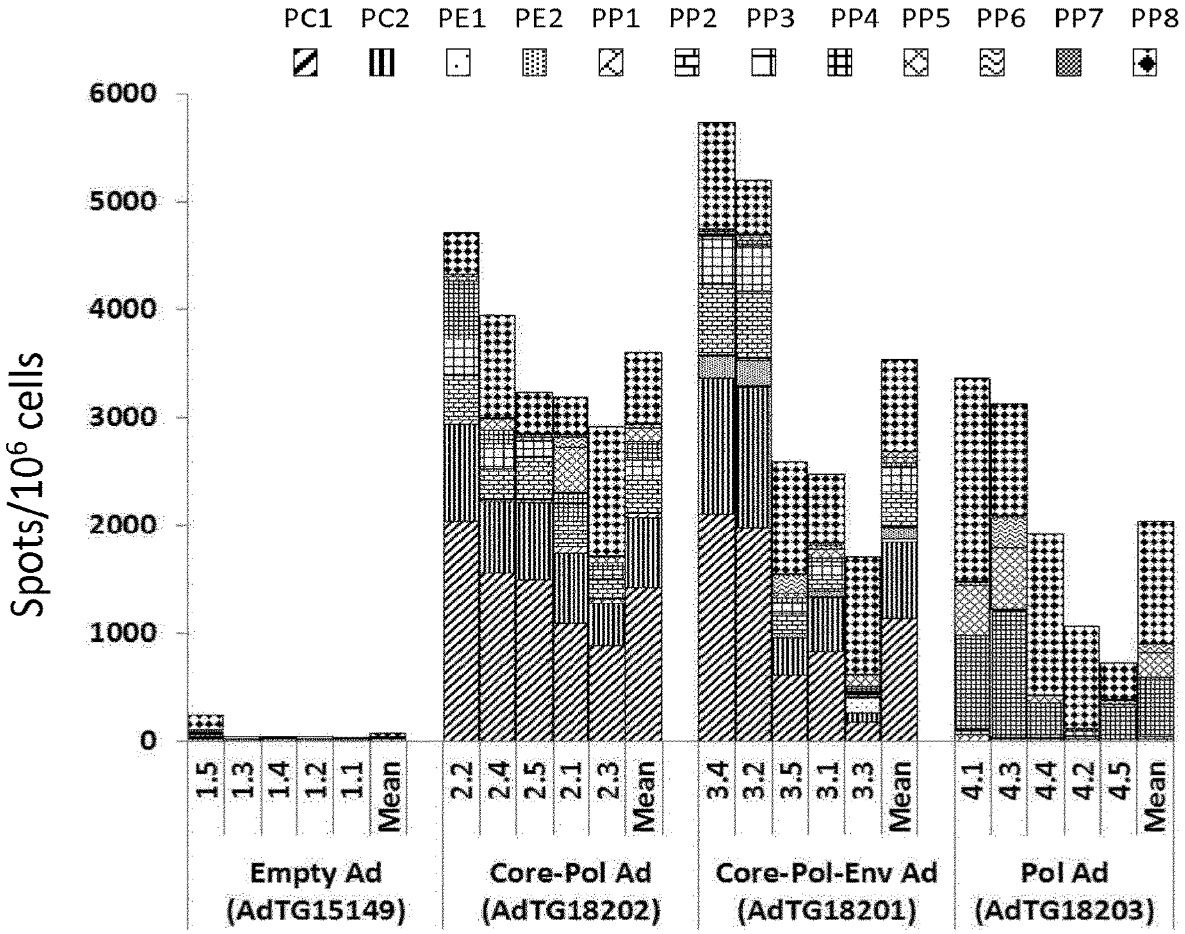
FIG. 4 illustrates Elispot IFNg assays carried out following immunization of HLA-A2 transgenic mice with Adenovirus AdTG18201 (Core-Pol-Env Ad), AdTG18202 (Core-Pol Ad), AdTG18203 (Pol Ad) and AdTG15149 (Empty Ad). Results are presented as the number of spots for $10^6$ cells corresponding to the frequency of IFNg producing cells specific of each peptide pools covering the antigen of interest, evaluated in the experiment for $10^6$ spleen cells of immunized mice. Each bar represent an individual mouse vaccinated by one or the other plasmid and indicated by its reference number (1.1 or 2.3 . . . etc) and the mean of all mice immunized with the same plasmid is also represented for each group (bar indicated as "mean" on the graph). For individual mouse and the means, frequency of IFNg producing cells specific of the different tested peptides are piled. Bars are filled with different symbols, each symbol representing the response against one specific HBV peptide as indicated by the legend on the graph.

As illustrated in FIG. 4, AdTG18203 encoding the HBV mutant polymerase polypeptide alone is able to induce IFNg producing cells specific of polymerase peptide pools 4, 5, 6 and 8. All immunized mice displayed specific T cell responses with a high frequency of IFNg producing cells mainly against the polymerase peptide pools 4 and 8.

As illustrated in FIG. 4, AdTG18202 encoding the HBV fusion protein "tCore-Pol*" induced IFNg producing cells specific of peptide pools PP2, PP3, PP4, PP5 and PP8, the polymerase-specific response being mainly focused on against PP2, PP3 et PP8. Immunization with AdTG18202 also resulted in the induction of high frequency of IFNg producing cells specific for the 2 Core peptide pools PC1 and PC2 with a higher frequency of T cells targeting PC1. Positive responses targeting both the polymerase and core antigens were observed in 5 out of the 5 vaccinated mice.

AdTG18201 encoding the HBV fusion protein "Core-Pol*-Env1-Env2" was also found immunogenic as illustrated in FIG. 4. More specifically, IFNg producing cells specific of polymerase peptide pools PP2, PP3, and PP8 were induced in all vaccinated mice, as well as against PP4 and PP5 although with weaker spots and lower responding mice frequencies. Immunization with AdTG18201 also resulted in the induction of high frequency of IFNg producing cells specific for the 2 Core peptide pools PC1 and PC2, in all vaccinated mice (5/5). Immunisation with AdTG18201 also induced specific T cell responses against the Env domains, even if those responses are weak and sporadic with 1 out of 5 mice displaying responses targeting PE1 and 2 out of 5 mice displaying responses targeting PE2.

2.2.2. Evaluation of HBV Specific IFNg Producing T Cells by Elispots IFNg Using HLA-A2 Peptides Following Immunization with AdTG18201.

The immunogenicity of one of the HBV fusion protein expressed by AdTG18201 was assessed in HLA-A2 transgenic mice. The animals were immunized by one subcutaneous injection of either AdTG18201 or AdTG15149 (empty adenovirus used as negative control). Specific T cell responses were evaluated by Elispot IFNg using HLA-A2 restricted epitopes contained in Polymerase (SLY), Core (FLP and ILC) and Envelope (VLQ and GLS).

Figure 5:
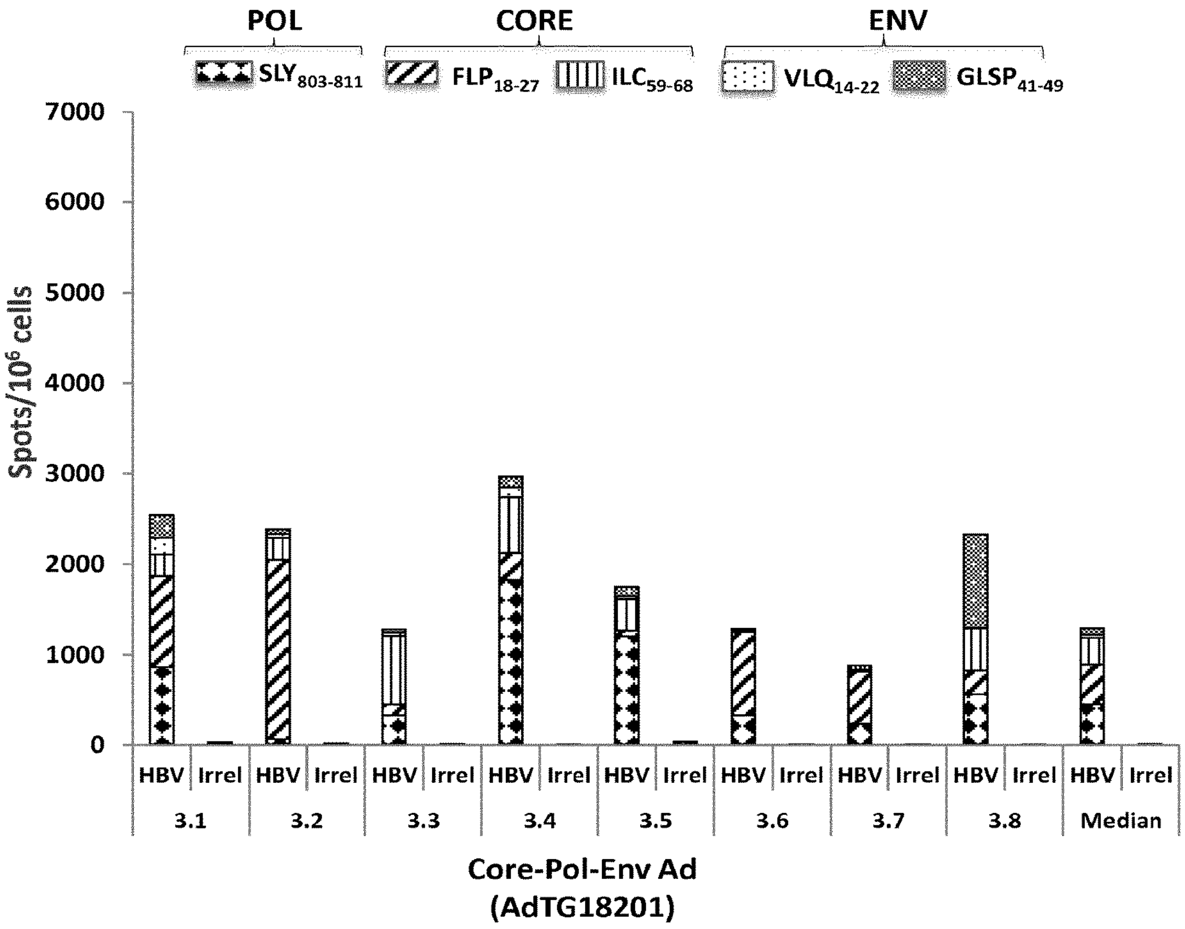
FIG. 5 illustrates Elispots IFNg assays carried out following immunization of HLA-A2 transgenic mice with AdTG18201 (Core-Pol-Env Ad). Results are presented as the number of spots for $10^6$ cells corresponding to the frequency of IFNg producing cells specific of each HBV HLA-A2 epitope, or of an irrelevant peptide, evaluated in the experiment for $10^6$ spleen cells of immunized mice. Each bar represents an individual mouse vaccinated by the AdTG18201 (indicated with its reference number, 3.1 to 3.8) and the median of all these mice immunized with AdTG18201 is also represented (bar indicated as «Median» on the graph). For individual mouse and median, frequency of IFNg producing cells specific of the different HBV HLA-A2 epitopes are piled whereas the frequency of IFNg producing cells observed in presence of an irrelevant peptide is represented on a separate bar (indicated «Irrel» on the graph for each mouse). Bars are filled with different symbols, each symbol representing the response against one specific HBV peptide as indicated by the legend on the graph.

As illustrated in FIG. 5, AdTG18201 encoding the HBV fusion protein «Core-Pol*-Env1-Env2» was found immunogenic. More specifically, IFNg producing cells specific of the polymerase HLA-A2 epitope, SLY, were induced in all AdTG18201-vaccinated mice. At the same time, AdTG18201 also induced IFNg-producing cells specific of the 2 HLA-A2 epitopes of the Core protein, FLP and ILC, with high frequencies. Immunization with AdTG18201 also induced specific T cell responses against the Env domains, although the frequencies and number of responding mice are lower, with 2 out of 8 tested mice displaying positive T cell response against the VLQ peptide and 5 out of 8 tested mice displaying positive T cell response against the GLSP peptide.

2.2.3. Evaluation of HBV Specific IFNg and/or TNFa Producing CD8+ T Cells by Intracellular Staining Assays Following Immunization of HLA-A2 Mice with the AdTG18201 and Using Selected Pools of Peptides.

The percentage of CD8+ T cells able to produce either IFNg alone or combined with TNFa in response to selected pools of peptides, covering a part of the polymerase protein (PP8, amino acids 725 to 835) and a part of the HBV Core protein (PC1, amino acids 1 to 100), was evaluated by ICS assay. The result is expressed as percentage of CD8+ T cells specific of these pools of peptides and producing IFNg alone and IFNg combined with TNFa.

Figure 6:
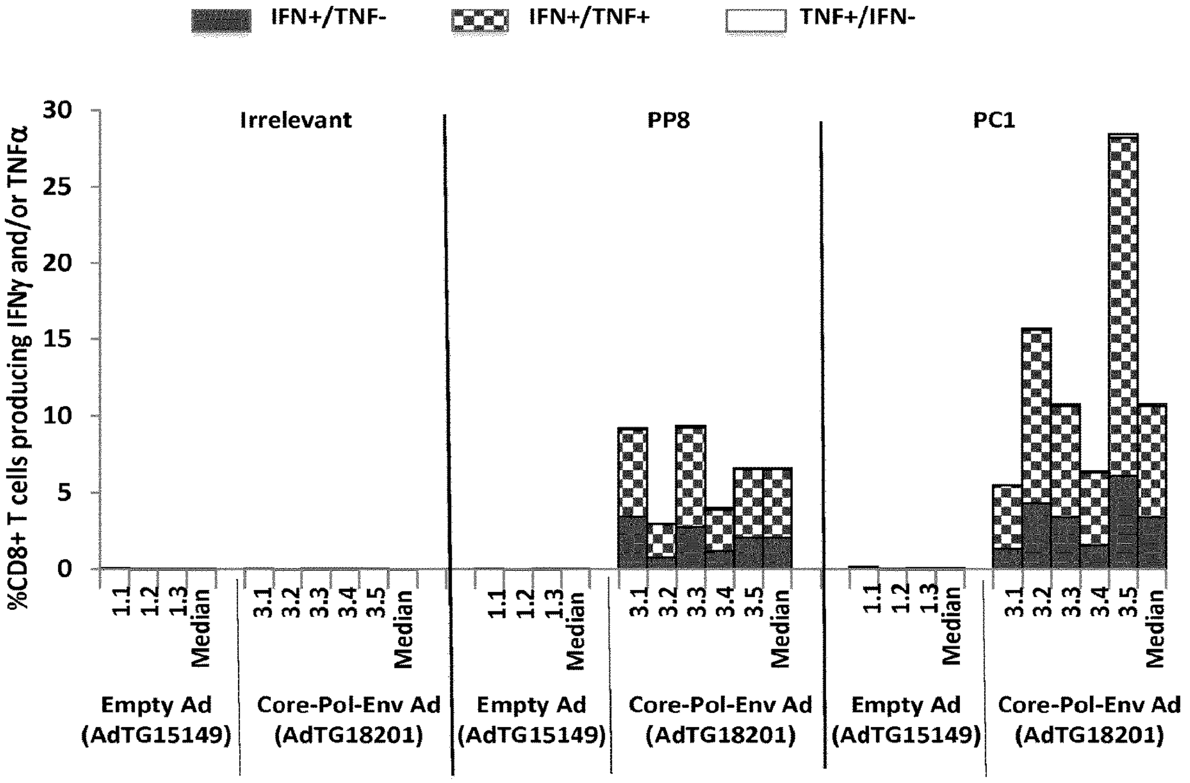
FIG. 6 illustrates ICS assays carried out following immunization of HLA-A2 mice with AdTG18201 (Core-Pol-Env Ad) or AdTG15149 (Empty Ad). Results are presented as the percentage of CD8 T cells producing IFNg alone or in combination with TNFa, specific of two selected peptide pools, called PP8 and PC1, and covering respectively a part of the HBV polymerase (amino acids 725 to 835) and a part of the HBV Core protein (amino acids 1 to 100). Each bar represents an individual mouse vaccinated by one or the other adenovirus and indicated by its reference number (1.1 or 3.2 . . . etc) and the median of all mice immunized with the same adenovirus is also represented for each group (bar indicated as "median" on the graph). Bars are filled with different symbols, each symbol representing the cytokine(s) produced by the detected CD8 T cells as indicated by the legend on the graph.

As shown in FIG. 6, AdTG18201 is specifically capable of inducing high percentages of CD8+ T cells producing both IFNg alone as well as IFNg combined with TNFa recognizing peptides of PP8 and PC1 pools. All vaccinated mice displayed a high percentage of both single producing (IFNg alone) and double producing (IFNg and TNFa) specific CD8+ T cells.

Of note, similar experiments performed in another mouse model, C57B16 mice, displayed similar results of immunogenicity of the AdTG18201 (not shown)

2.2.4. Evaluation of the Induction of In Vivo Functional CD8+ T Cells Using an In Vivo CTL Assays Following Immunization of HLA-A2 Mice with the AdTG18201.

The capacity of AdTG18201 to induce in vivo functional CD8 T cells displaying cytolytic activity was evaluated by in vivo cytolytic (or CTL) assay in HLA-A2 mice following immunization with AdTG18201 or AdTG15149 (as negative control) and using 3 of the HLA-A2 epitopes already shown as being targeted by induced CD8+ T cells producing IFNg (SLY, FLP and ILC).

Figure 7A:
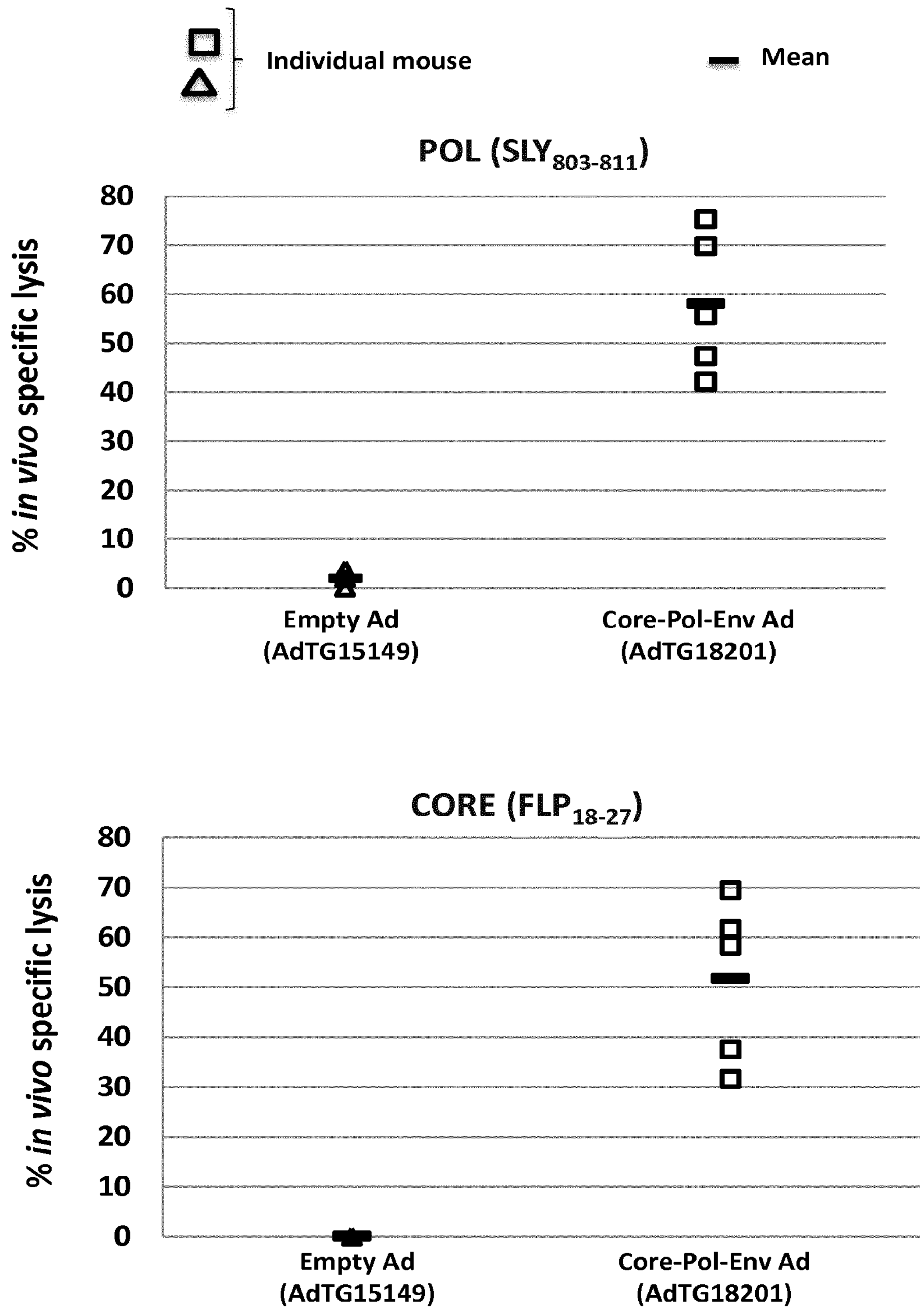
FIGS. 7A-B illustrates in vivo CTL assays carried out following immunization of HLA-A2 mice with AdTG18201 (Core-Pol-Env Ad) or AdTG15149 (Empty Ad). Results are presented as the percentage of in vivo specific lysis, ie lysis specific of the HBV HLA-A2 epitopes that were tested. Each square or triangle symbols represents an individual mouse and the mean of all mice immunized with the same adenovirus is also represented for each group (represented by a thick bar symbol on the graph).
Figure 7B:
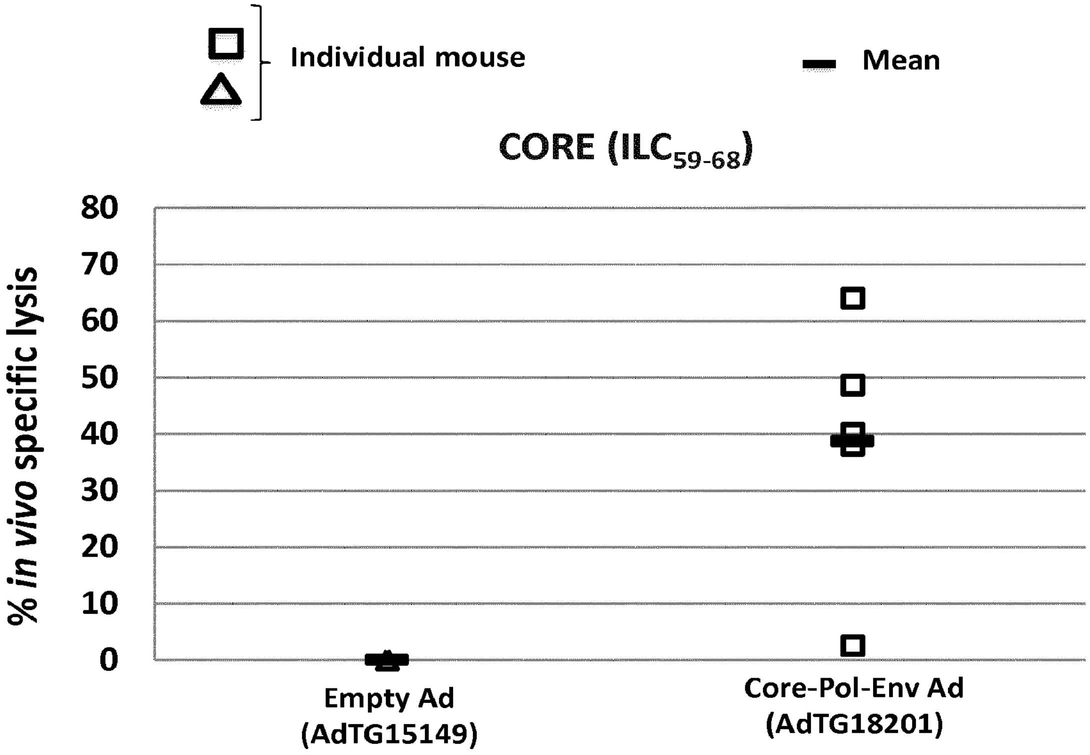

As illustrated by FIG. 7, the AdTG18201 is able to induce high percentage of in vivo specific lysis against the polymerase epitope, SLY, with a specific lysis detected for all immunized mice and a percentage ranging from 42% to 75% (FIG. 7*a*). It was also shown that the AdTG18201 is able to induce high percentage of in vivo specific lysis against the 2 tested HLA-A2 epitopes of the Core protein, FLP (FIG. 7*a*) and ILC (FIG. 7*b*), with percentages ranging from 32% to 69% and 3% to 64% respectively. Response against env epitope was detectable but at low levels.

These data clearly demonstrate the ability of the AdTG18201 to induce in vivo functional CD8+ T cells displaying cytolytic activity and targeting both the HBV polymerase and the HBV core proteins.

2.2.5. Evaluation of the Induction of Functional CD8+ T Cells in HBV Transgenic Mice Following Immunization with AdTG18201 and Using an ICS Assay.

The capacity of AdTG18201 to induce functional T cells in a tolerant mouse model was evaluated in HBV transgenic mice. In fact, these mice are transgenic for the HBV genome and, thus, tolerant to HBV antigens mimicking, to some extent, the tolerance encountered in HBV chronic patients. The HBV transgenic mice were immunized by one subcutaneous injection of AdTG18201 ($10^8$ iu) or AdTG15149 as negative control. Induced T cells were monitored both in spleens and livers of vaccinated mice by ICS (detection of CD8+ T cells producing both IFNg and TNFa). In this specific model, peptides identified to be reactive in C57Bl/6J mice were used to screen the induced T cell response: a pool of the VSA and the N13F peptides for the polymerase and the F13L peptide for the envelope.

Figure 8:
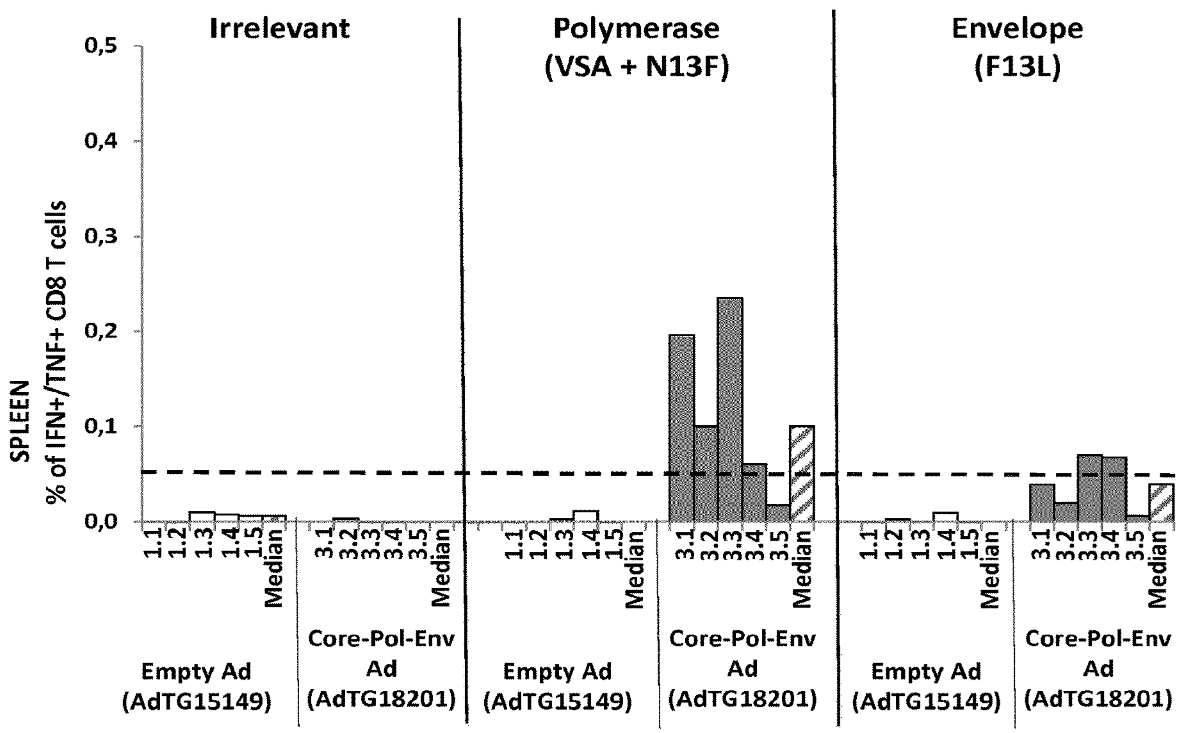
FIG. 8 illustrates ICS assays carried out following immunization of HBV transgenic mice with AdTG18201 (Core-Pol-Env Ad) or AdTG15149 (Empty Ad). Results are presented as the percentage of CD8 T cells producing both IFNg and TNFa specific of epitopes from the HBV polymerase (mix of 2 peptides, called VSA and N13F) or from the HBV envelope (1 peptide called F13L) and found both in spleens and in livers of vaccinated mice. Each bar represents an individual mouse vaccinated by one or the other adenovirus and indicated by its reference number (1.1 or 3.2 . . . etc) and the median of all mice immunized with the same adenovirus is also represented for each group (bar indicated as "median" on the graph). The dotted line represented on graphs corresponds to the cut-off of the experiment, ie the threshold above which observed percentage of CD8 T cells is considered as a positive immune response.
Figure 8:
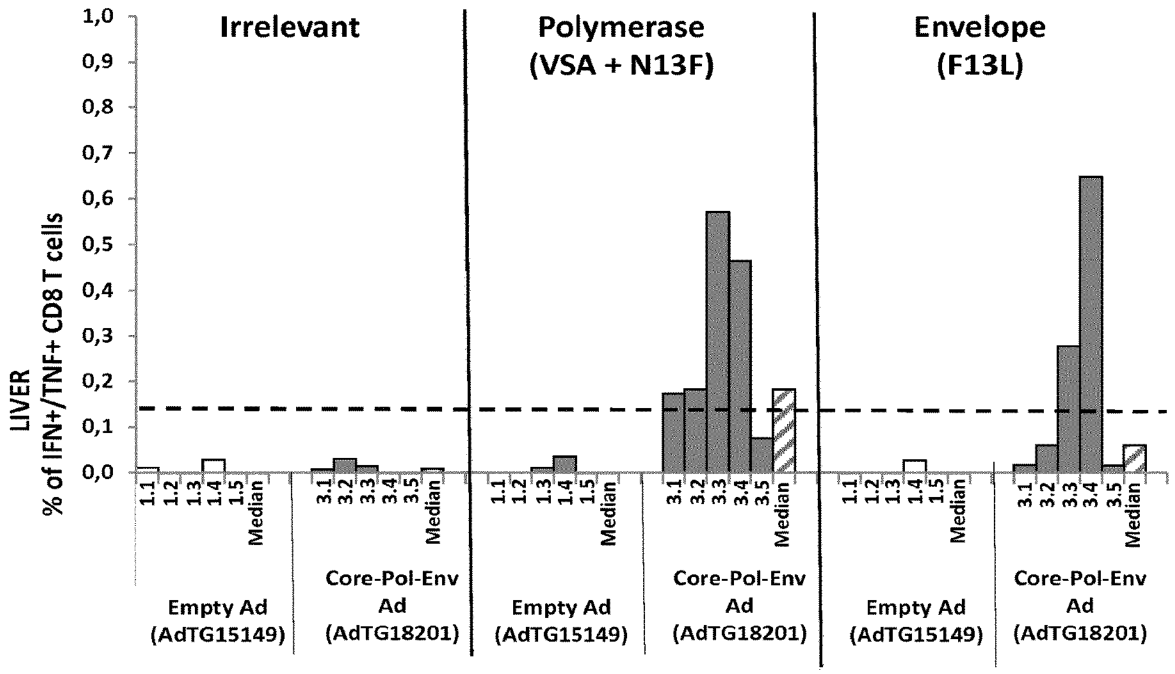

As illustrated in FIG. 8, functional CD8+ T cells producing both IFNg and TNFa were detected in spleens and livers of AdTG18201-vaccinated mice, with 4 out of 5 tested mice displaying functional IFNg/TNFa producing CD8+ T cells specific of polymerase and with 2 out of 5 tested mice displaying functional IFNg/TNFa producing CD8+ T cells specific of Envelope in both organs. As expected, no responses were detected in mice immunized with the empty AdTG15149 or when stimulation is using an irrelevant peptide.

All together, these data demonstrate the ability of the viral vector AdTG18201 expressing a fusion protein containing a RNaseH-defective and YMDD-deleted pol mutant, env domains and core to induce functional CD8+ T cells, producing both IFNg and TNFa, in a HBV tolerant model.

2.3 Evaluation of Different Doses and Schedules of Immunization with the AdTG18201 or the AdTG18202.

2.3.1. Adenovirus Dose Evaluation.

The immunogenicity of the HBV fusion protein expressed by AdTG18201 was assessed in HLA-A2 transgenic mice at different doses. The animals were immunized by one subcutaneous injection of either AdTG18201 at a dose of $10^5$ iu or $10^6$ iu or $10^7$ iu or $10^8$ iu or $10^9$ iu or AdTG15149 at $10^9$ iu (empty adenovirus used as negative control). Specific T cell responses were evaluated by Elispot IFNg using HLA-A2 restricted epitopes contained in Polymerase (SLY), Core (FLP and ILC) and Envelope (VLQ and GLS).

Figure 9:
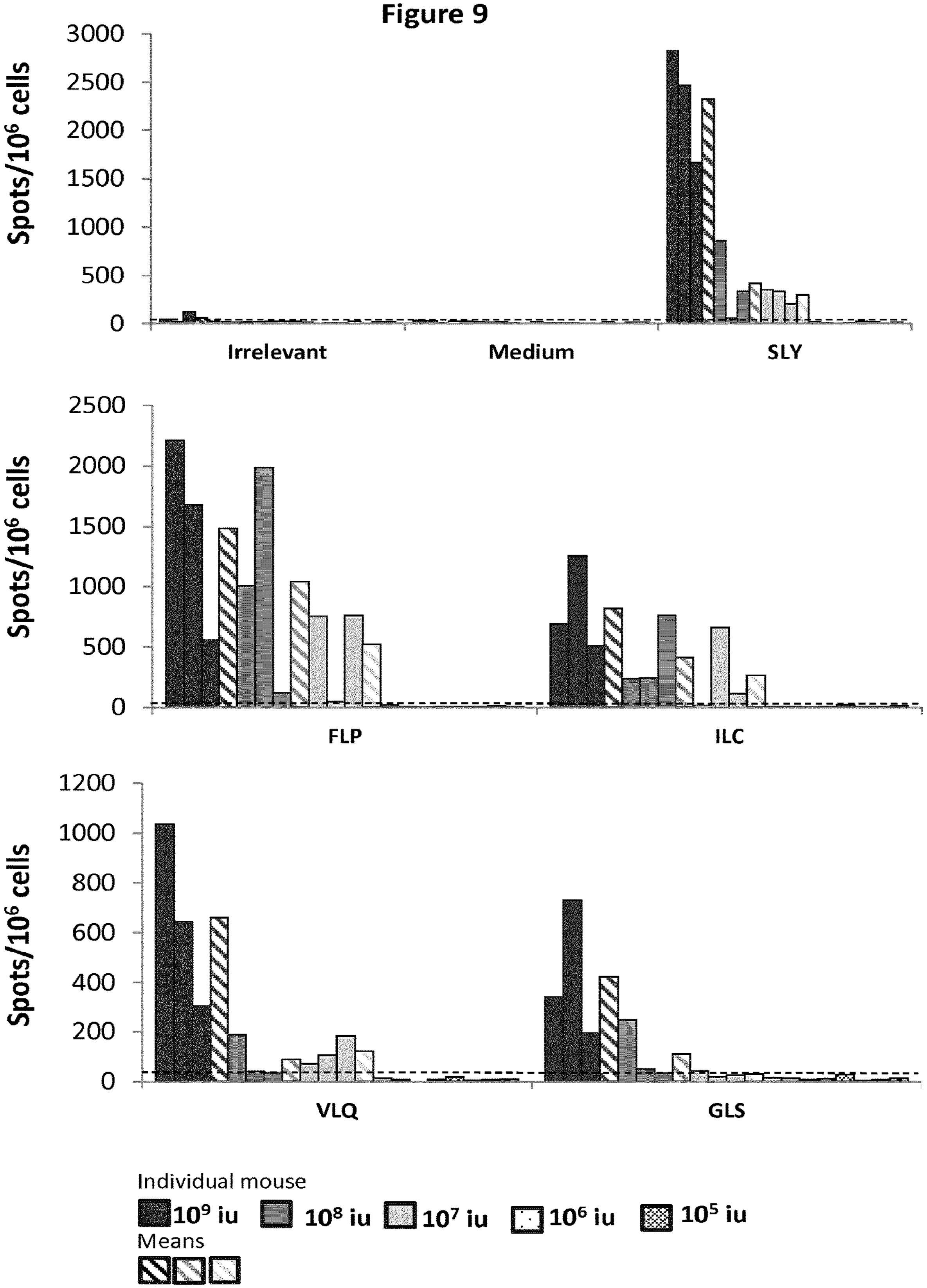
FIG. 9 illustrates Elispots IFNg assays carried out following immunization of HLA-A2 transgenic mice with AdTG18201 (Core-Pol-Env Ad) with different doses, from $10^5$ iu to $10^9$ iu. Results are presented as the number of spots for $10^6$ cells corresponding to the frequency of IFNg producing cells specific of each HBV HLA-A2 epitope, or of an irrelevant peptide, or in presence of medium only, evaluated in the experiment for $10^6$ spleen cells of immunized mice. Each solid or dotted bar represents an individual mouse vaccinated by the AdTG18201 and the mean of all mice immunized with AdTG18201 at one specific dose is also represented (hatched bars). The different doses are represented by different colors or symbols as indicated by the legend on the graph. The dotted-line represents the cut-off value, defined as described in Material and Methods, above which observed T cell responses are considered as positive.

As illustrated in FIG. 9, AdTG18201 encoding the HBV fusion protein «Core-Pol*-Env1-Env2» was found immunogenic when injected at doses of $10^7$ iu, $10^8$ iu and $10^9$ iu. More specifically, no IFNg producing cells specific of the tested HLA-A2 epitopes of Core, Polymerase or Env domains were detected with the doses of $10^5$ and $10^6$ iu. Specific IFNg producing cells targeting the 2 tested core epitopes and the tested epitope of Pol were detected for doses of $10^7$, $10^8$ and $10^9$ iu. A dose effect is observed for the 3 epitopes (SLY, FLP and ILC). For the 2 epitopes of the Env domains (VLQ and GLS), frequencies of IFNg producing cells are low for doses of $10^7$ and $10^8$ whereas frequencies are clearly increased with a dose of $10^9$ iu.

2.3.2. Evaluation of Multiple Immunization Schedule at Short Term Interval.

The immunogenicity of one of the HBV fusion protein expressed by AdTG18202 was assessed in HLA-A2 transgenic mice according to different schedules of immunization. AdTG18202 was either administered once or 3 times (1 injection/week during 3 weeks) or 6 times (1 injection/week during 6 weeks) and the induced immune T cell responses was assessed 2 weeks after the last injection by an Elispots IFNg assay and using HLA-A2 restricted epitopes, SLY (Pol) and FLP and ILC (Core). Some mice were immunized 6 times with an empty adenovirus as a negative control (not shown)

Figure 10:
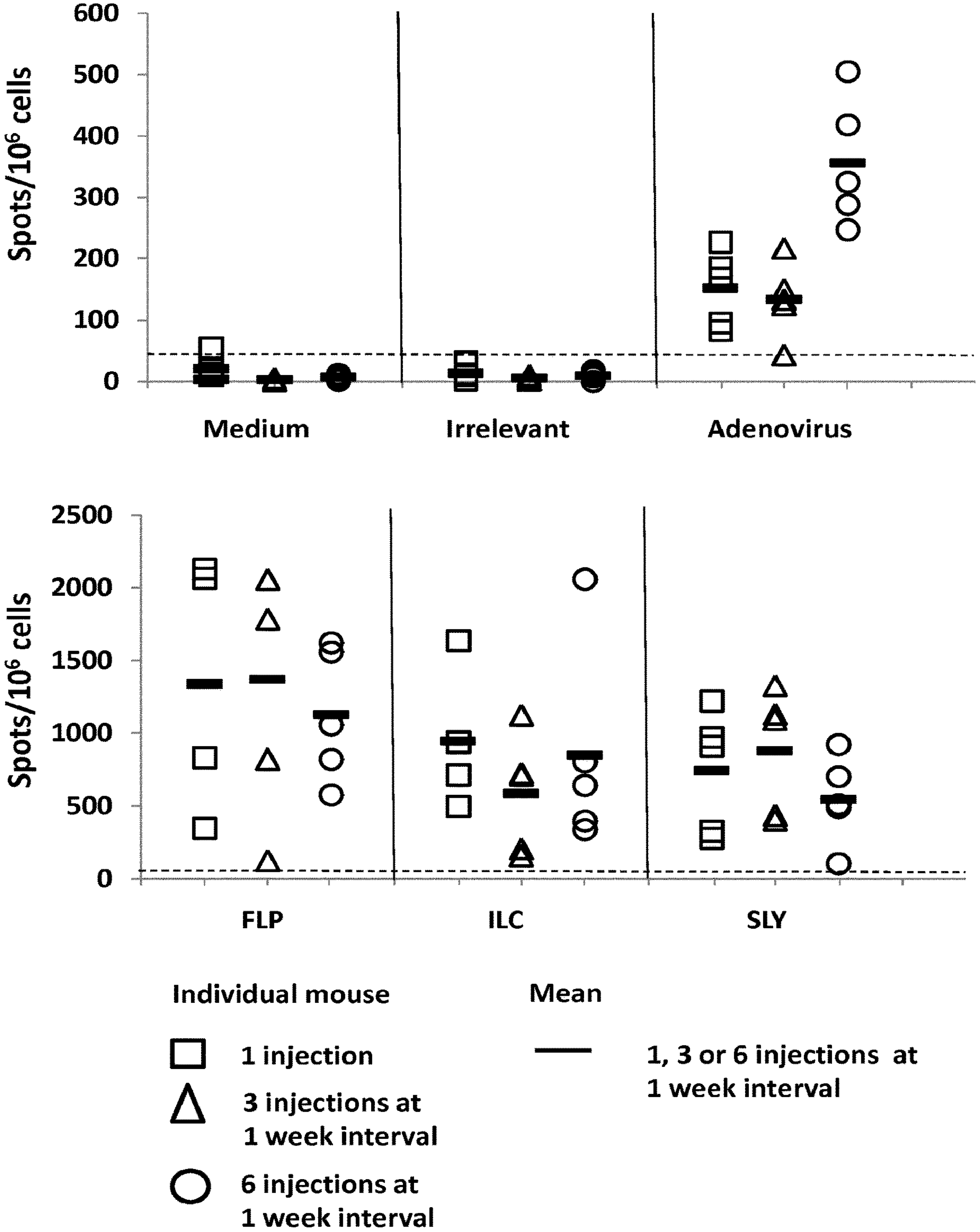
FIG. 10 illustrated Elispots IFNg assays carried out following immunization of HLA-A2 transgenic mice with AdTG18202 (Core-Pol Ad) according to different schedules of injections Mice were immunized either once (squares) or received 3 injections at 1 week interval (triangles) or 6 injections at 1 week interval (circles). Results are presented as the number of spots for $10^6$ cells corresponding to the frequency of IFNg producing cells specific of each HBV HLA-A2 epitope, or of the adenovirus vector or an irrelevant peptide or in presence of medium only evaluated in the experiment for $10^6$ spleen cells of immunized mice. Each symbol (square, triangle or circle) represents an individual mouse vaccinated by the AdTG18202 and the mean of all mice immunized with AdTG18202 with one of the tested schedules is represented by a solid thick line. The dotted-line represents the cut-off value, defined as described in Material and Methods, above which observed T cell responses are considered as positive.

As illustrated in FIG. 10, AdTG18202 encoding for the fusion protein "Core-Pol*" was found immunogenic whatever the tested schedules. More particularly, no specific T cell response was detected with medium alone and irrelevant peptide whereas high and similar frequencies of IFNg producing cells were detected in presence of the 3 tested HBV epitopes, SLY, FLP and ILC. Frequencies of detected IFNg producing T cells appeared comparable between groups of mice injected once, 3 times or 6 times at 1 week interval, without the appearance, at the IFNg production level, of a T cell exhaustion due to a too high number of immunizations in a short time-interval. The adenovirus specific T cell responses appeared higher when mice were injected 6 times than when they were injected once or 3 times. As expected, no HBV-specific T cell responses were observed following immunization with an empty adenovirus.

2.3.3. Evaluation of Multiple Immunization Schedule at Long Term Interval.

The immunogenicity of one of the HBV fusion protein expressed by AdTG18202 was assessed in HLA-A2 transgenic mice according to different schedules of immunization. AdTG18202 was either administered once (2 (group 1) or 20 (group 2) weeks before the monitoring of T cell responses) or twice (2 injections at 2 (group 3) or 4 (group 4) month interval, monitoring of T cell responses 2 weeks after the last immunization) or three times (at 2 month interval (group 5), monitoring of T cell responses 2 weeks after the last injection). Induced T cells were monitored by an Elispots IFNg assay and using HLA-A2 restricted epitopes, SLY (Pol) and FLP and ILC (Core). Some mice were immunized either once or three times at 2 month interval with an empty adenovirus as a negative control (not shown).

Figure 11A:
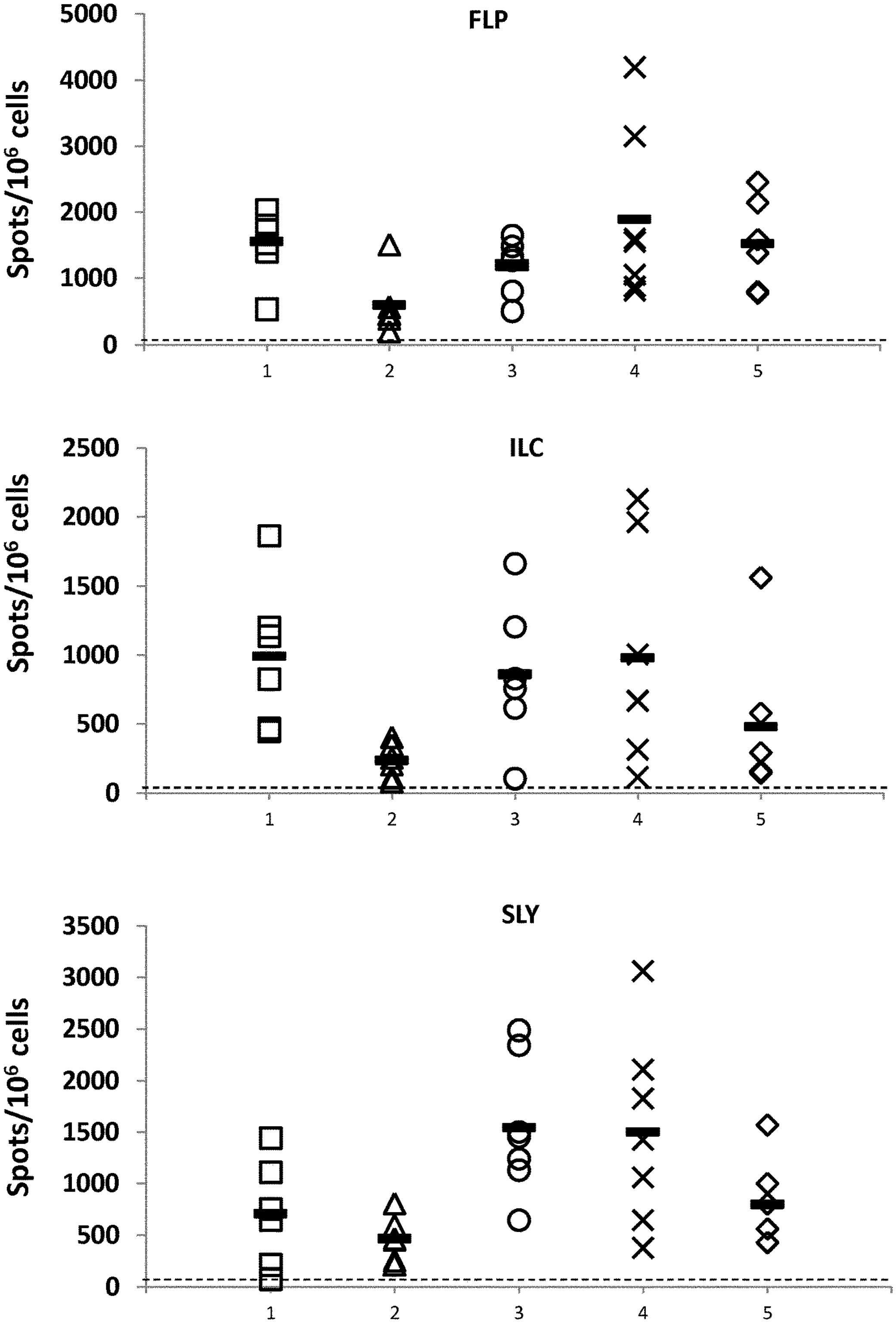
FIGS. 11A-B illustrated Elispots IFNg assays carried out following immunization of HLA-A2 transgenic mice with AdTG18202 (Core-Pol Ad) according to different schedules of injections Mice were immunized either once 2 weeks before the monitoring of T cell responses (group 1 represented by squares) or once 20 weeks before the monitoring of T cell responses (group 2 represented by triangles), or twice at 2 months interval (group 3 represented by circles), or twice at 4 months interval (group 4 represented by crosses) or three times at 2 month interval (group 5 represented by rhombuses). For all groups except group 2, T cell responses were monitored 2 weeks after the last injection. Results are presented as the number of spots for $10^6$ cells corresponding to the frequency of IFNg producing cells specific of each HBV HLA-A2 epitope or an irrelevant peptide or in presence of medium only, evaluated in the experiment for $10^6$ spleen cells of immunized mice. Each symbol (square, triangle, circle, cross, rhombus) represents an individual mouse vaccinated by the AdTG18202 and the mean of all mice immunized with AdTG18202 with one of the tested schedules is represented by a solid thick line. The dotted-line represents the cut-off value, defined as described in Material and Methods, above which observed T cell responses are considered as positive.
Figure 11B:
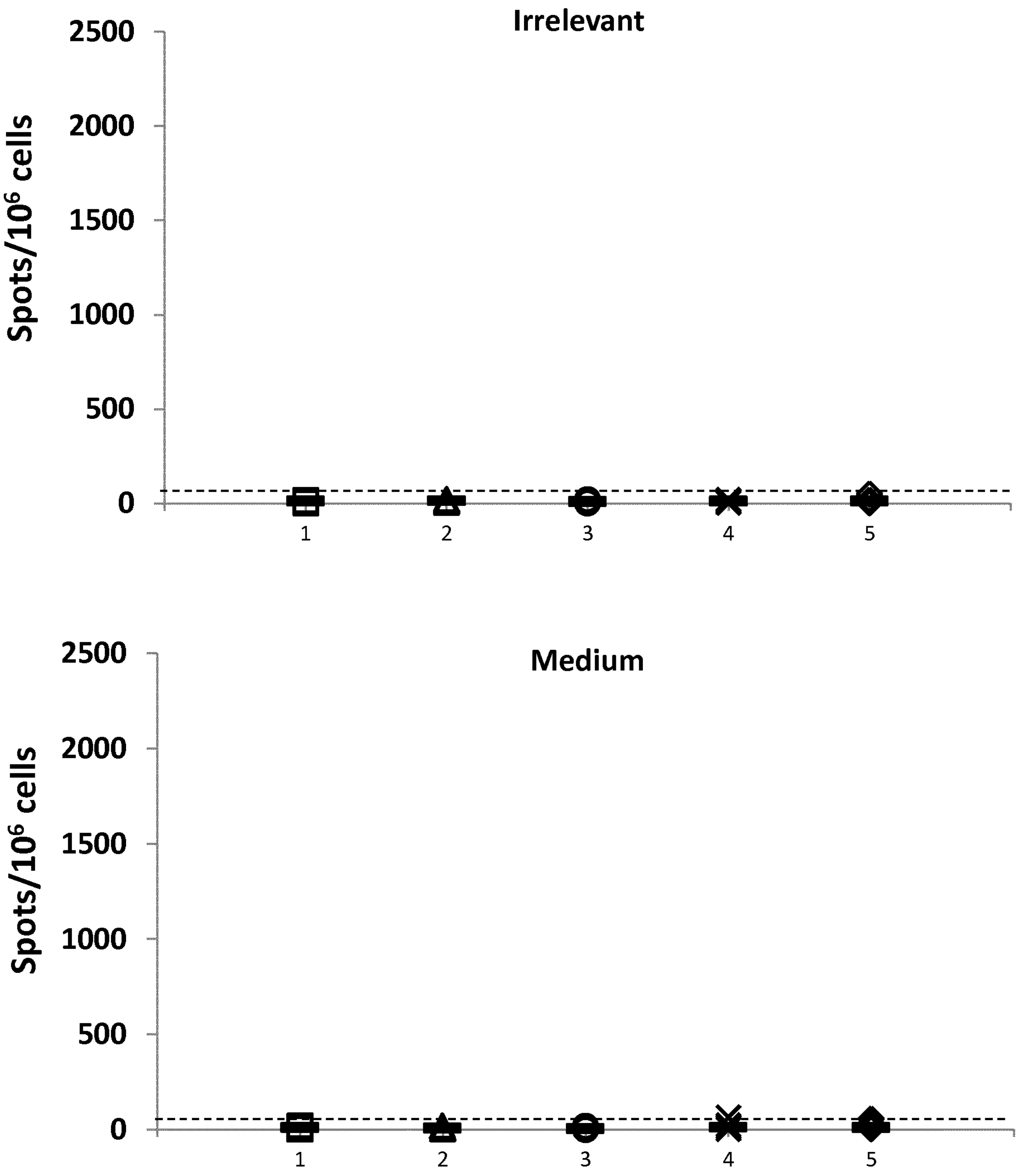

As illustrated by FIGS. 11A-B, AdTG18202 encoding for the fusion protein "Core-Pol*" was found immunogenic whatever the tested schedule whereas no specific T cell response was detected following immunizations with AdTG18202 in presence of medium alone or of an irrelevant peptide. More particularly, observed specific T cell responses in group 2 showed that even if lower than those observed in group 1, 2 weeks after 1 immunization, induced T cell responses after one injection of AdTG18202 still exist 20 weeks after the injection. Observed T cell responses in group 3 and 4 showed that a $2^{nd}$ immunization 2 or 4 months after the first one was able to recall T cell responses specific of HBV epitopes at least at the level of the primary immune response observed in group 1, even slightly higher for the SLY epitope. A similar observation was done with mice immunized three times at 2 month interval (group 5) with a recall of induced T cell responses through the $2^{nd}$ and $3^{rd}$ injections to a level similar to the one observed in group 1. As expected, no HBV-specific T cell responses were observed following immunization with an empty adenovirus 2.4 Electron Microscopy Observation A549 cells were infected in vitro by AdTG18201 at MOI 25, 50 or 100 and cells were collected at either 16 h, 24 h or 48 post-infection. Collected cells were then treated to be observed by electron microscopy.

Some virus-like particles (VLP) were observed in the nucleus and cytoplasm of AdTG18201 infected cells whereas none of these structures were observed in cells infected by an empty adenovirus. These VLP were mainly located within the nucleus. In some cells both protein aggregates and VLP were observed.

The invention claimed is:

1. A method for treating or inhibiting or delaying an HBV infection, a chronic HBV infection or HBV-associated liver lesions, liver cancer, liver inflammation, chronic liver disease, comprising one or more administration(s), to a subject in need thereof, of a therapeutically effective amount of composition comprising a nucleic acid molecule coding for a mutant polypeptide, a vector comprising said nucleic acid molecule, a host cell comprising said nucleic acid molecule or said vector, or any combination thereof, wherein said mutant polypeptide comprises a mutated HBV polymerase domain with an internal deletion that functionally disrupts the polymerase activity, wherein said internal deletion is of at least 4 amino acid residues and at most 30 amino acid residues, said mutated polymerase domain comprising:

the amino acid sequence shown in SEQ ID NO:1 but lacking at least the Tyr residue in position 203, the Met residue in position 204, the Asp residue in position 205, the Asp residue in position 206, the Val residue in position 207, the Val residue in position 208, and the Leu residue in position 209.

2. The method according to claim 1, wherein said nucleic acid molecule encodes a mutant polypeptide which, in addition to the deletion of residues 203 to 209 of SEQ ID NO:1:

comprises a polymerase domain having the amino acid sequence shown in SEQ ID NO:2;

comprises a RNaseH domain having the amino acid sequence shown in SEQ ID NO:3 or SEQ ID NO:4;

comprises an amino acid sequence which exhibits at least 90% of identity with the amino acid sequence shown in SEQ ID NO:5; or comprises an amino acid sequence selected from which exhibits at least 90% of identity with the amino acid sequence shown in any of SEQ ID NOs 6-12.

3. The method according to claim 1, wherein said nucleic acid molecule encodes a mutant polypeptide which, in addition to the deletion of residues 203 to 209 of SEQ ID NO:1, comprises a nucleotide sequence exhibiting at least 90% of identity with the nucleotide sequence shown in any of SEQ ID NOs 13-17.

4. The method according to claim 1, wherein said vector is a plasmid or a viral vector for expression in higher eukaryotic cells or organisms.

5. The method according to claim 4, wherein said vector is a viral vector originating from a retrovirus, adenovirus, adenovirus-associated virus (AAV), poxvirus, herpes virus, measles virus, foamy virus, alphavirus, or vesicular stomatis virus.

6. The method according to claim 5, wherein said vector is a replication-defective adenoviral vector originating from a human or from a chimpanzee adenovirus.

7. The method according to claim 6, wherein the nucleic acid molecule is inserted in the adenoviral E1 region and placed under the control of a CMV promoter.

8. The method according to claim 5, wherein said vector is a poxviral vector originating from a canarypox, a fowlpox, or a vaccinia virus.

9. The method according to claim 1, wherein said vector is selected from the group consisting of:

A defective Ad vector comprising inserted in place of the E1 region a nucleic acid molecule placed under the control of a promoter such as the CMV promoter, and encoding a mutant polypeptide comprising an amino acid sequence as shown in SEQ ID NO:5 or a fusion protein comprising an amino acid sequence as shown in SEQ ID NO:6 or SEQ ID NO:8;

A replication-defective Ad vector comprising inserted in place of the E1 region a nucleic acid molecule placed under the control of a promoter such as the CMV promoter, and comprising the nucleotide sequence shown in SEQ ID NO:13, SEQ ID NO:14 or SEQ ID NO:15;

A replication-defective Ad vector, especially a defective AdCh3 comprising inserted in place of the E1 region a nucleic acid molecule placed under the control of a promoter such as the CMV promoter and comprising the nucleotide sequence shown in SEQ ID NO:16 or SEQ ID NO:17;

A MVA vector comprising a nucleic acid molecule placed under the control of a vaccinia promoter such as the 7.5K or pH5R promoter, and encoding a mutant polypeptide comprising an amino acid sequence as shown in SEQ ID NO:5 or SEQ ID NO:10 or a fusion protein comprising an amino acid sequence as shown in SEQ ID NO:6, SEQ ID NO:8 or SEQ ID NO:12; and A MVA vector comprising a nucleic acid molecule placed under the control of a vaccinia promoter such as the 7.5K or pH5R promoter, and comprising the nucleotide sequence shown in SEQ ID NO:13, SEQ ID NO:14 or SEQ ID NO:15.

10. The method according to claim 1, wherein said vector is in the form of infectious viral particles.

11. The method according to claim 1, wherein the mutant polypeptide encoded by said nucleic acid molecule is fused in frame to a signal peptide and to a trans-membrane peptide.

12. The method according to claim 1, wherein said composition further comprises a pharmaceutically acceptable vehicle.

13. The method according to claim 1, wherein said composition is formulated for intramuscular, subcutaneous, intradermal administration or scarification.

14. The method according to claim 1, wherein said composition comprises doses of about $5\times10^8$, about $10^9$, about $5\times10^9$, about $10^{10}$, about $5\times10^{10}$ vp or about $10^{11}$ vp of an adenoviral vector.

15. The method according to claim 1, wherein said composition comprises doses of about $5\times10^8$, about $10^7$, about $5\times10^7$, about $10^8$, or about $5\times10^8$ pfu of an MVA vector.

16. The method according to claim 1, for treating a chronic HBV infection.

17. The method according to claim 1, for eliciting or stimulating an immune response in the treated organism.

18. The method according to claim 17, wherein said elicited or stimulated immune response is specific and/or non-specific, humoral and/or cellular.

19. The method according to claim 18, wherein said immune response is a T cell response CD4+ or CD8+-mediated or both, directed to an HBV polypeptide/epitope.

20. The method according to claim 1, wherein said vector is an adenoviral vector and said method comprises one or two intramuscular or subcutaneous administrations.

21. The method according to claim 1, which is carried out in combination with the standard of care.

22. The method according to claim 1, which is carried out according to prime boost modality.

23. The method according to claim 22, wherein the priming is carried out with an MVA vector and the boosting with an Ad vector.

24. The method according to claim 23, wherein the MVA and/or the Ad vector encodes the fusion protein shown in SEQ ID NO: 8.

25. The method according to claim 24, comprising at least 3 subcutaneous administrations of the MVA vector separated by a period of time varying from 3 days to 3 months followed by an intramuscular or subcutaneous boost of the adenovirus vector.

26. The method according to claim 1, wherein said HBV-associated liver lesions, liver cancer, liver inflammation, chronic liver disease is selected from the group consisting of: cirrhosis, steatosis, fibrosis, hepatocellular carcinoma and liver carcinoma.

* * * * *